United States Patent
Lloyd et al.

(10) Patent No.: US 6,624,309 B1
(45) Date of Patent: Sep. 23, 2003

(54) BENZOIC ACID DERIVATIVES AND RELATED COMPOUNDS AS ANTIARRHYTHMIC AGENTS

(75) Inventors: John Lloyd, Yardley, PA (US); George C. Rovnyak, Hopewell, NJ (US); Philip D. Stein, Pennington, NJ (US); Saleem Ahmad, Wall, NJ (US); Karnail S. Atwal, Newtown, PA (US); Thomas J. Caulfield, Lawrenceville, NJ (US); Michael A. Poss, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/254,398

(22) Filed: Sep. 25, 2002

Related U.S. Application Data

(63) Continuation of application No. 09/973,826, filed on Oct. 10, 2001, now abandoned, which is a continuation of application No. 09/468,648, filed on Dec. 21, 1999, now abandoned, which is a continuation of application No. 09/008,825, filed on Jan. 20, 1998, now abandoned.
(60) Provisional application No. 60/038,811, filed on Feb. 21, 1997.

(51) Int. Cl.[7] .......................... C07D 27/06; A61K 31/41
(52) U.S. Cl. .................. 548/131; 548/247; 548/253; 548/267.6; 548/309.7; 548/338.1; 548/375.1; 548/491; 546/337; 544/264; 544/301; 514/256; 514/261; 514/357; 514/378; 514/381; 514/383; 514/394; 514/399; 514/403; 514/406; 514/415; 514/438
(58) Field of Search .................. 548/309.7, 338.1, 548/491, 267.6, 247, 253, 375.1, 131; 546/337; 549/77; 544/301, 264; 514/394, 399, 364, 415, 383, 378, 381, 403, 406, 357, 438, 256, 261

(56) References Cited

U.S. PATENT DOCUMENTS

| | | |
|---|---|---|
| 3,915,983 A | 10/1975 | Dransch et al. |
| 4,393,054 A | 7/1983 | Allen |
| 4,503,054 A | 3/1985 | Brown et al. |
| 4,740,453 A | 4/1988 | Nakamura et al. |
| 4,786,643 A | 11/1988 | Sanger et al. |
| 4,804,662 A | 2/1989 | Nickisch et al. |
| 4,898,863 A | 2/1990 | Brown et al. |
| 5,017,211 A | 5/1991 | Wenger et al. |
| 5,236,943 A | 8/1993 | Heitsch et al. |
| 5,322,847 A | 6/1994 | Marfat et al. |
| 5,428,031 A | 6/1995 | Sanguinetti et al. |
| 5,453,421 A | 9/1995 | Atwal et al. |
| 5,596,020 A | 1/1997 | Morris et al. |
| 5,604,185 A | 2/1997 | Hen |
| 5,607,944 A | 3/1997 | Linz et al. |
| 5,661,153 A | 8/1997 | Isobe et al. |

FOREIGN PATENT DOCUMENTS

| | | | |
|---|---|---|---|
| DE | 42 41 632 | * | 6/1994 |
| DE | 4326344 A1 | | 2/1995 |
| DE | 19837386 A1 | | 2/1999 |
| GB | 2276165 A | | 9/1994 |
| JP | 62-275163 | * | 11/1987 |
| JP | 7-188246 | * | 7/1995 |
| WO | WO 93/00313 | | 1/1993 |
| WO | WO93/04061 | | 3/1993 |
| WO | WO 94/14435 | | 7/1994 |
| WO | WO95/14471 | | 6/1995 |
| WO | WO96/05839 | | 2/1996 |
| WO | WO 99/43210 | | 9/1999 |
| WO | WO 00/45799 | | 8/2000 |

OTHER PUBLICATIONS

Selnick, H.G. et al, "Class III Antiarrhythmic Activity in Vivo by Selective Blockade of the Slowly Activating Cardiac Delayed Rectifier Potassium Current $I_{Ks}$ by (R)–2–(2, 4–Trifluoromethyl)–N–[2–oxo–5–phenyl–1–(2,2,2–trifluoroethyl)–2,3–dihydro–1H–benzo[e][1,4]diazepin–3–yl]acetamide", J. Med. Chem., 40 (24), 3865–3868, 1997.

Nair, L.A. et al, "Emerging Class III Antiarrhythmic Agents: Mechanism of Action and Proarrhythmic Potential", Cardiovascular Drugs and Therapy 1997;11:149–167.

* cited by examiner

Primary Examiner—Shailenda Kumar
(74) Attorney, Agent, or Firm—Burton Rodney

(57) ABSTRACT

Benzoic acid derivatives of the formula

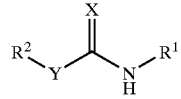

where

X is oxygen, sulfur, —NH, —NR[1], —N—CN, —N—OR[1] or —N—NO$_2$;

Y is a single bond, —C=C—, or —NH;

R[1] is alkyl, alkenyl, alkynyl, aryl, cycloalkyl, heterocyclo, or (heterocyclo)alkyl; and R[2] is aryl or heterocyclo. The compounds of formula I are useful in the treatment of arrhythmia.

6 Claims, No Drawings

BENZOIC ACID DERIVATIVES AND RELATED COMPOUNDS AS ANTIARRHYTHMIC AGENTS

REFERENCE TO OTHER APPLICATIONS

This application is a continuation of application Ser. No. 09/973,826 filed Oct. 10, 2001 now abandoned, which is a continuation of application Ser. No. 09/468,648 filed Dec. 21, 1999, now abandoned, which is a continuation of application Ser. No. 09/008,825 filed Jan. 20, 1998, now abandoned, which takes priority from provisional application No. 60/038,811 filed Feb. 21, 1997.

BRIEF DESCRIPTION OF THE INVENTION

This invention is concerned with compounds of the formula

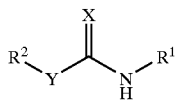

where

X is oxygen, sulfur, —NH, —NR$^1$, —N—CN, —N—OR$^1$ or —N—NO$_2$:

Y is a single bond, —C=C—, or —NH;

R$^1$ is alkyl, alkenyl, alkynyl, aryl, cycloalkyl, heterocyclo, (aryl)alkyl, (cycloalkyl)alkyl, (substituted amino)alkyl, or (heterocyclo)alkyl; and R$^2$ is aryl or heterocyclo.

The compounds of formula I are useful in the treatment of arrhythmia. The invention is also concerned with pharmaceutical compositions comprising one or more of the novel compounds as an active antiarrhythmic agent either alone or in combination with other cardiovascular agents such as a β-blocker or other antiarrhythmic agent; and a method of treating arrhythmia by administration of one of the novel compounds or compositions thereof to a patient in need of such treatment.

DETAILED DESCRIPTION OF THE INVENTION

Definition of Terms

Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 8 carbon atoms, preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like; as well as such groups substituted by, one or more substituents such as halo, alkoxy, amino, substituted amino, aryl, cycloalkyl, hydroxy, alkanoylamino, arylcarbonylamino, nitro, cyano, thiol, alkylthio and the like.

The term "alkoxy" refers to alkyl-O—.

The term "alkylthio" refers alkyl-S—.

The term "alkenyl" refers to any of the above alkyl groups further containing at least one carbon to carbon double bond.

The term "alkynyl" refers to any of the above alkyl groups further containing at least one carbon to carbon triple bond.

The term "alkanoyl" refers to alkyl-C(O)—.

The term "cycloalkyl" refers to saturated cyclic hydrocarbon groups containing 3 to 8 ring carbons optionally substitued with one or more substituents such as alkyl or hydroxy.

The term "halogen" or "halo" refers to chlorine, bromine, iodine and fluorine.

The term "aryl" refers to monocyclic or bicyclic aromatic hydrocarbon groups having 6 to 12 carbon atoms in the ring portion, such as phenyl, 1-naphthyl, 2-naphthyl, phenanthrene or dihydrophenanthrene; or such groups substituted with one or more substituents such as alkyl, alkenyl, alkynyl, alkylthio, alkoxy, halo, nitro, cyano, hydroxy, amino, substituted amino, phenyl, —C(O)-phenyl, substituted phenyl, —C(O)-substituted amino, heterocycle, carboxylic acid or carboxylic ester.

The term "aryl" also includes those groups listed above fused to a five- or six-membered ring which optionally contains an oxygen, sulfur or nitrogen atom. The five- or six-membered ring may further optionally be substituted with for example, alkyl or —phenyl—CF$_3$.

The term "heterocyclo" or "hetero" refers to fully saturated or unsaturated rings of five or six atoms containing one or two oxygen and/or sulfur atoms and/or one to four nitrogen atoms provided that the total number of hetero atoms in the ring is four or less. Exemplary monocyclic heterocyclo groups include 2- and 3-thienyl, 2- and 3-furyl, 2-, 3- and 4-pyridyl and imidazolyl.

The term heterocyclo or hetero also includes bicyclic rings wherein the five- or six-membered ring containing oxygen and/or sulfur and/or nitrogen atoms as defined above is fused to a benzene ring and the bicyclic ring is attached by way of an available atom.

Exemplary bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranyl.

The term heterocyclo or hetero also includes such monocyclic and bicyclic rings wherein an available atom is substituted by one or more substituents such as alkyl, aryl, alkylthio, alkoxy, halo, nitro, keto, cyano, hydroxy, azo, oxo, thiazo, amino, substituted amino, carboxylic acid, carboxylic ester, or alkoxy further substituted with a carboxylic acid or a five- to eight-membered ring optionally containing 1 to 4 heteroatoms selected from oxygen, nitrogen and sulfur, optionally substituted by groups such as alkyl or halogen.

The term "substituted amino" refers to a group of the formula —NZ$^2$Z$^3$ wherein Z$^2$ is hydrogen, alkyl, cycloalkyl, aryl, morpholinylalkyl, heterocyclo or (heterocyclo)alkyl and Z$^3$ is hydrogen, alkyl, cycloalkyl or aryl further substituted with a carboxylic acid or carboxylic ester, provided that when Z$^2$ is hydrogen, then Z$^3$ is other than hydrogen; or Z$^2$ and Z$^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl; or 1-pyrrolidinyl, 1-piperidinyl, or 1-azepinyl, optionally substituted with alkyl, alkoxy, alkylthio, halo, aryl or hydroxy.

Throughout the specification, groups and substituents thereof are chosen to provide stable moieties and compounds.

The compounds of formula I may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compound I with the desired ion in a medium in which the salt precipitates or in an aqueous medium followed by evaporation. Other salts can be formed as known to those having ordinary skill in the art.

The compounds of formula I may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compound I in an equivalent amount of the acid in a medium in which the salt precipitates or in an aqueous medium followed by evaporation.

In addition, zwitterions ("inner salts") may be formed.

A compound of the formula I may also have prodrug forms. Any compound that will be converted in vivo to provide the bioactive agent (i.e., the compound of formula I) is a prodrug within the scope and spirit of the invention.

Various forms of prodrugs are well known in the art. For examples of such prodrug derivatives, see:
a) *Design of Prodrugs*, edited by H. Bundgaard, (Elsevier, 1985);
b) *Methods in Enzymology*, Vol. 42, 309–396, edited by K. Widder et al. (Academic Press, 1985);
c) *A Textbook of Drug Design and Development*, edited by Krogsgaard-Larsen and H. Bundgaard, Chapter 5, "Design and Application of Prodrugs," by H. Bundgaard, 113–191 (1991);
d) *Advanced Drug Delivery Reviews*, H. Bundgaard, 8, 1–38 (1992);
e) *Journal of Pharmaceutical Sciences*, H. Bundgaard et al., 77, 285 (1988); and
f) *Chem Pharm Bull*, N. Kakeya et al., 32, 692 (1984).

It should further be understood that solvates (e.g., hydrates) of the compounds of formula I are also within the scope of the present invention. Methods of solvation are generally known in the art.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The below described processes can utilize racemates, enantiomers or diastereomers as starting materials. When diastereomeric products are prepared, they can be separated by conventional methods for example, chromatographyc or fractional crystallization.

Use and Utility

The compounds of formula 1 are useful in the treatment of arrhythmia. More specifically, the compounds of the present invention have the pharmacological properties required for the antiarrhythmic agents of Class III.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $1_{Na}$ and $1_{Ca}$ respectively) or by reducing outward repolarizing potassium ($K^+$) currents. The delayed rectifier $(I_K)K^+$ current is the main outward current involved in the overall repolarization process during the action potential plateau, whereas the transient outward $(1_{to})$ and inward rectifier $(1_{K1})K^+$ current are responsible for the rapid initial and terminal phases of repolarization, respectively. Cellular electrophysiologic studies have demonstrated that $1_K$ consists of two pharmacologically and kinetically distinct $K^+$ current subtypes, $1_{Kr}$ (rapidly activating and deactivating) and $1_{Ks}$ (slowly activating and deactivating).

Most Class III agents that are known to be in development predominantly block $1_{Kr}$. These agents have a potential liability in that they have an enhanced risk of proarrhythmia at slow heart rates. The compounds of the present invention prolong the mycocardial action potential in vitro without a significant depression of the Vmax and with the prolongation of interval in anesthetized dogs. In addition the compounds of the present invention selectively block $I_{Ks}$. The preferred compounds of the present invention are those which have selectivity of $I_{Ks}:I_{Kr}$ greater than or equal to 5.

The compounds of the present invention are effective in treating and preventing all types of arrhythmias including ventricular and atrial (supraventricular) arrhythmias. The compounds of the present invention are especially useful to control reentrant arrhythmias and prevent sudden death due to the ventricular fibrillation.

In the novel method of this invention of treating arrhythmia, a novel compound or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

The novel compounds of this invention can be administered as the sole active ingredient or in combination with other antiarrhythmic agents or other cardiovascular agents.

The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or reparations is such that a suitable dosage will be obtained.

Preferred Moieties

The preferred compounds of the present invention are those ompounds of formula I where:

X is oxygen or N—CN;

Y is a single bond or —C=C—; and $R^1$ is alkyl, cycloalkyl, (aryl)alkyl, (cycloalkyl)alkyl, or (substituted amino)alkyl.

Process of Preparation

The compounds of the instant invention may be obtained by methods exemplified by the following descriptions.

The compounds of formula 1 wherein X is O and Y is a single bond or —C≡C— (compounds of formula 1a), can be prepared as outlined in Scheme 1 below.

Scheme 1

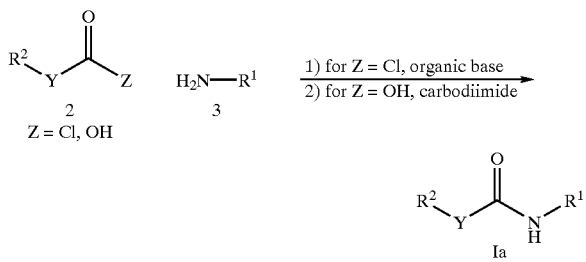

The acid chloride (Z=Cl) of formula 2 is reacted with an amine of formula 3 in the presence of a base such as triethylamine and an organic solvent such as dichloromethane, tetrahydrofuran or dimethylformamide etc. to form the compounds of formula 1a.

Alternatively, compounds of formula 1a can be prepared from an acid of formula 2 (Z=OH) and an amine of formula 3 in an organic solvent in the presence of a carbodiimide such as dicyclohexylcabodiimide or 1-(3-dimethylaminopropyl)-2-ethylcarbodiimide hydrochloride (WSC).

Compounds of formula 1 wherein X is S, can be prepared from compounds of formula 1 wherein X is O by treatment with a thionating agent such as phosphorus pentasulfide ($P_4S_{10}$) or the Lawesson's reagent.

Compounds of formula 2 and 3 are commercially available or they can be prepared by methods described in the literature.

The compounds of formula I wherein X is NCN and Y is a single bond or —C≡C— (i.e., compounds of formula Ib), can be prepared as outlined in Scheme 2.

Scheme 2

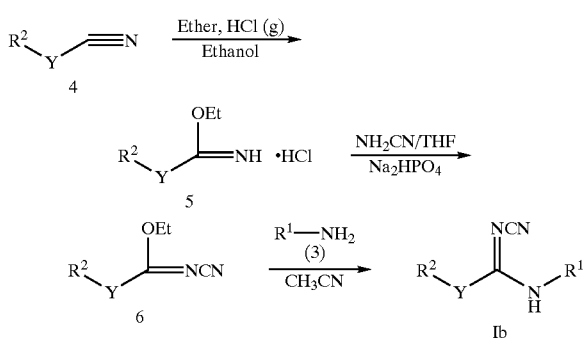

The nitrile of formula 4 is converted to the imino ether of formula 5 by treatment with hydrochloric acid in ethanol. The imino ether 5 is then reacted with cyanamide to provide a compound of formula 6 which on reaction with an amine of formula 3 provides the compounds of formula 1b. Compounds of formula 4 are commercially available or they can be prepared by methods described in the literature.

The compounds of formula 1 wherein X is NCN and Y is NH (i.e., compounds of formula 1c), can be prepared as outlined in Scheme 3.

Scheme 3

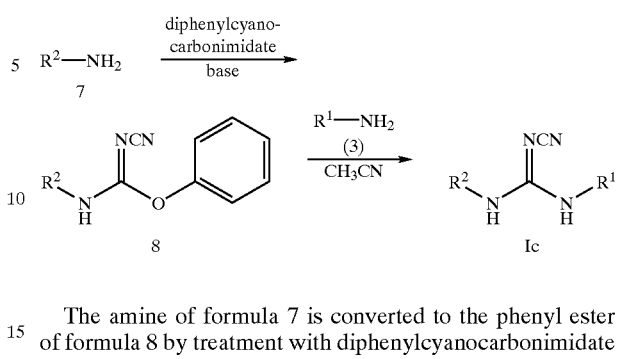

The amine of formula 7 is converted to the phenyl ester of formula 8 by treatment with diphenylcyanocarbonimidate in the presence of a base (e.g., sodium hydride, diisopropylethyl amine). The compound of formula 8 is converted to the compounds of formula 1c by treatment with an amine of formula 3 in an organic solvent. Compounds of formula 7 are commercially available or they can be prepared by methods described in the literature.

Alternatively, compounds of formula 1 wherein X is NCN and Y is NH, can be prepared by methods similar to those described in the literature such as that by Atwal et. al. *Tetrahedron Letters*, Vol. 30, pp 7313–7316 (1989) and references therein.

The compounds of formula 1 wherein X is O or S and Y is NH (i.e., compounds of formula 1d), can be prepared as outlined in Scheme 4.

Scheme 4

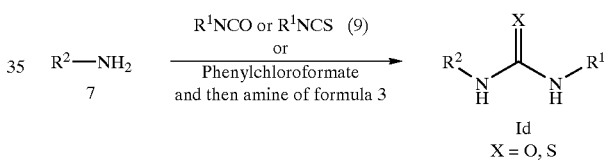

The amine of formula 7 is reacted with an isocyanate or isothiocyanate of formula 9 in an organic solvent to provide the compounds of formula 1d.

Alternatively, the compounds of formula 1 wherein X is O or S and Y is NH, can be prepared by sequential treatment of an amine of formula 7 with an arylchloroformate (e.g., phenylchloroformate) and an amine of formula 3.

Compounds of formula 1 wherein X is S, can be prepared from compounds of formula 1 wherein X is O by treatment with a standard thionating agent such as phosphorus pentasulfide ($P_4S_{10}$) or the Lawesson's reagent. Compounds of formula 9 are commercially available or they can be prepared by conventional methods described in the literature.

The compounds of formula 1 wherein $R^2$ contains an aryl or a heterocyclo substituent (formula 1e) may be prepared according to Scheme 5.

Scheme 5

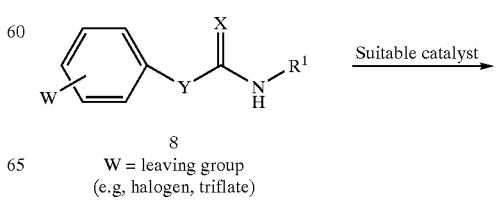

W = leaving group
(e.g. halogen, triflate)

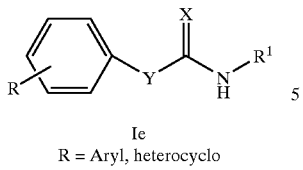

Ie
R = Aryl, heterocyclo

Compounds of formula 1e can be prepared from compounds of formula 8 wherein W is a suitable leaving group such as halogen or triflate by treatment with a heterocyclo group or an aryl ring containing a suitable reacting group such as an amino group, boronic acid and trialkyltin in the presence of a suitable catalyst (base, palladium etc.). Compounds of formula 8 are prepared by methods described in Schemes 1 to 4.

The compounds of formula 1 wherein $R^2$ contains a heterocyclic substituent (oxazole, imidazole, oxadiazole, thiadiazole etc.), can also be prepared from compounds of formula 1* wherein $R^2$ contains a suitable heterocyclo forming group such as an acid or a derivative thereof as described in Scheme 6.

Scheme 6

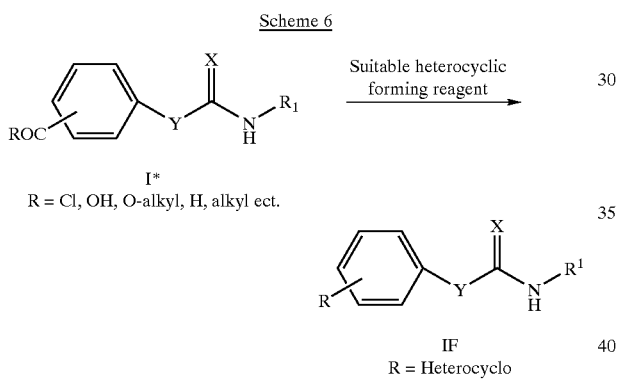

Compounds of formula 1f are prepared by treatment with a suitable heterocyclo forming reagent (amidine, hydroxyamidine etc.). This transformation can also be accomplished in a stepwise fashion by modification of methods described in the literature.

All other compounds of formula I may be prepared by modification of the procedures discussed herein as known by those having ordinary skill in the art. The intermediates used to prepare compounds of formula I are described herein or may be derived from known compounds by those having ordinary skill in the art or are commercially available.

EXAMPLE

The following examples and preparations describe the manner and process of making and using the invention and are illustrative rather than limiting. It should be understood that there may be other embodiments which fall within the spirit and scope of the invention as defined by the claims appended hereto.

Example 1

(+)-N-[(2,2-Dimethylcyclopentyl)methyl]-4-hexyloxybenzamide and (−)-N-[(2,2-Dimethylcyclopentyl)methyl]-4-hexyloxybenzamide

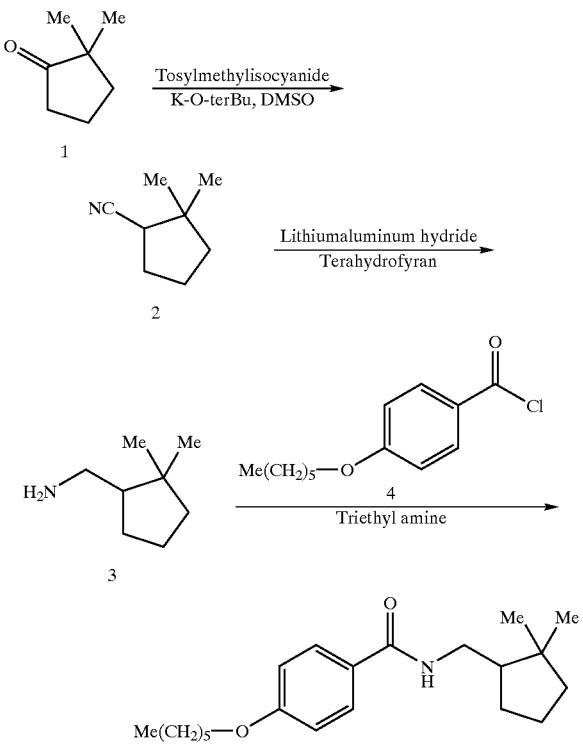

A. 2,2-Dimethylcyclopentanecarbonitrile

Tosylmethyl isocyanide (3.76 g, 19.3 mmol) was dissolved in dimethylsulfoxide (15 mL) and cooled to 0° C. Solid potassium t-butoxide (6.3 g, 59.2 mmol) was added and a thick brown precipitate formed. The reaction mixture was warmed to room temperature and 2,2-dimethylcyclopentanone (2.0 mL, 16.0 mmol) was added in anhydrous methanol (680 μL) and the reaction mixture was stirred for 30 hours. It was diluted with ethyl acetate, acidified with hydrochloric acid and extracted with hexanes. The extracts were dried over magnesium sulfate, filtered and the solvent was removed to provide a brown oil which was purified by chromatography on silica gel eluted with 0–50% dichloromethane in hexanes to yield a yellow oil (612 mg, 31%).

B. 2,2-Dimethylcyclopentanemethanamine

Compound 2 (600 mg, 4.87 mmol) was dissolved in tetrahydrofuran (10 mL) and cooled to 0° C. Lithium aluminum hydride (185 mg, 4.87 mmol) was added and the mixture was stirred for 17 hours. The reaction mixture was then quenched by addition of sodium sulfate decahydrate, filtered through celite and the celite washed with ether. To the solution was added hydrogen chloride (3 mL, 3.9 M in dioxane) and the solvent was removed. The residue was dissolved in water and lyophilized to yield a white solid (613 mg, 77%).

C. (+)-N-[(2,2-Dimethylcyclopentyl)methyl]-4-hexyloxybenzamide and (−)-N-[(2,2-Dimethyl-cyclopentyl)methyl]-4-hexyloxybenzamide:

To compound 3 (300 mg, 1.83 mmol) in dichloromethane (8 mL) was added triethylamine (766 uL, 5.50 mmol) and 4-hexyloxybenzoyl chloride (4) (430 μL, 1.92 mmol) and the reaction mixture was stirred for 24 hours at room temperature. The reaction mixture was diluted with ethyl acetate and washed with hydrochloric acid, saturated sodium bicarbonate and brine. The organic layer was dried over magnesium sulfate, filtered and the solvent was removed to yield a white solid (600 mg). Purification by preparative HPLC (Chiracel OD, 50×500 mm; 10% isopropanol, hexane; 90 mL/min) provided 99 mg of a faster moving isomer, 342 mg of mixed fraction and 65 mg of a slower moving isomer. Further purification of the faster moving isomer by flash chromatography on silica gel eluted with 10% acetone in hexanes provided (+)-N-[(2,2-dimethylcyclopentyl)methyl]-4-hexyloxybenzamide as a white solid (90 mg): mp 68–69° C.; $[\alpha]_D$ (MeOH, c 0.55)+20.7°. Analysis calculated for $C_{21}H_{33}NO_2$: C, 76.09; H, 10.03; N, 4.24. Found: C, 75.99; H, 10.11; N, 4.11.

Further purification of the slower moving isomer by flash chromatography on silica gel eluting with 10% acetone in hexane provided (−)-N-[(2,2-dimethylcyclopentyl)-methyl]-4-hexyloxybenzamide as a white solid (57 mg): mp 69–70° C.; $[\alpha]_D$ (MeOH, c 0.55)−18.50; Analysis calculated for $C_{21}H_{33}NO_2$: C, 76.09; H, 10.03; N, 4.24. Found: C, 75.95; H, 10.12; N, 4.13.

Example 1a

N-(3,3-Dimethylcyclopentyl)-4-hexyloxybenzamide (Adams' catalyst, 331 mg, 1.46 mmol) were added and the mixture was stirred under hydrogen (balloon) for 24 hours. The reaction was purged with argon and diluted with ethyl acetate. The mixture was loaded onto silica gel and purified by flash chromatography on silica gel eluted with 5% triethylamine and hexane to provide 1.24 g (84%) of a clear colorless oil.

B. 3,3-Dimethylcyclopentanamine Hydrochloride

The amine (2, 130 mg, 0.64 mmol) was dissolved in 2 mL of ethanol. Palladium (5% on charcoal, 13 mg) was added and the reaction was stirred under hydrogen (balloon) at 50° C. for 10 hours then at room temperature for 10 hours. The mixture was diluted with ether then filtered through Celite. Hydrogen chloride (3.86 M, 300 μL) was added and the solvent removed to yield 87 mg (91%) of a white solid.

C. N-(3,3-Dimethylcyclopentyl)-4-hexyloxybenzamide

The amine hydrochloride (3, 87 mg, 0.58 mmol) was dissolve in 2 mL dichloromethane. Triethylamine (244 μL, 1.75 mmol) and 4-hexyloxybenzoyl chloride (155 μL, 0.70 mmol) were added and the mixture was stirred for 4 hours at room temperature. The reaction was diluted with ethyl acetate and washed with hydrochloric acid (1.0 M, aq.), sodium bicarbonate (sat'd., aq.) and sodium chloride (sat'd., aq.). The organic layer was dried over magnesium sulfate,-

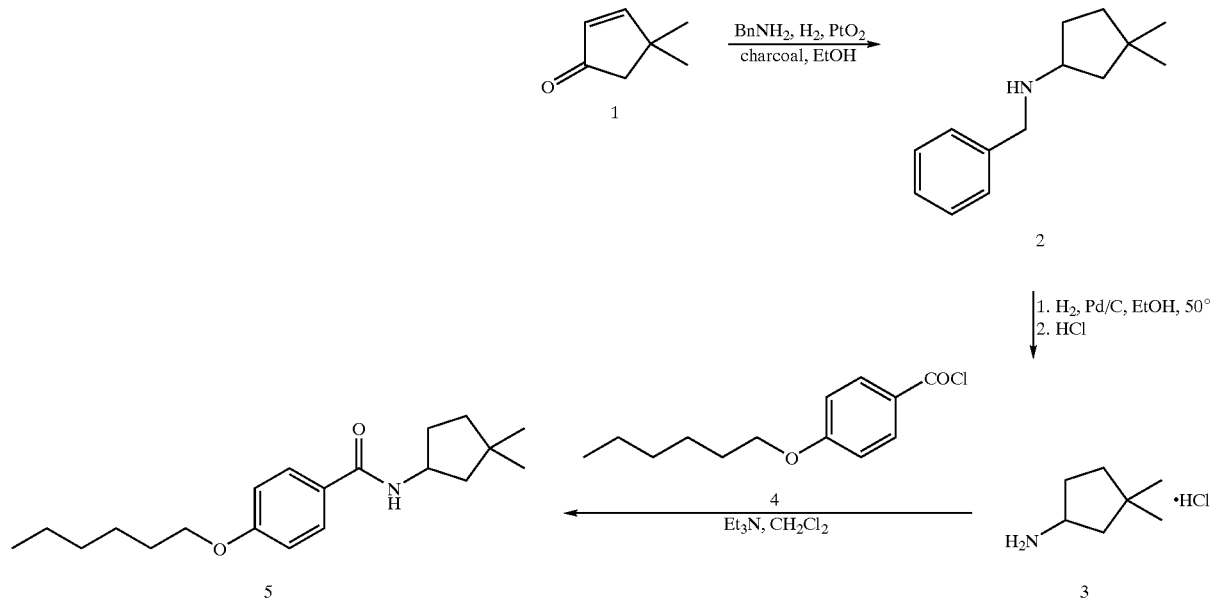

A. N-(3,3-Dimethylcyclopentyl)benzenemethanamine 4,4-Dimethyl-2-cyclopenten-1-one (804 mg, 7.30 mmol) and benzylamine (877 μL, 8.03 mmol) were dissolved in 15 mL of ethanol. Charcoal (400 mg) and platinum oxide filtered and the solvent removed. Purification by flash chromatography on silica gel eluted with 10% acetone, hexane provided 138 mg (75%) of a white solid. mp 82–83° C.; Anal calc'd for $C_{20}H_{31}NO_2$: C, 75.67; H, 9.84; N, 4.41. Found: C, 75.86; H, 10.10; N, 4.37.

Example 1c

N-(3,3-Dimethylcyclopentyl)-4-benzoylbenzamide

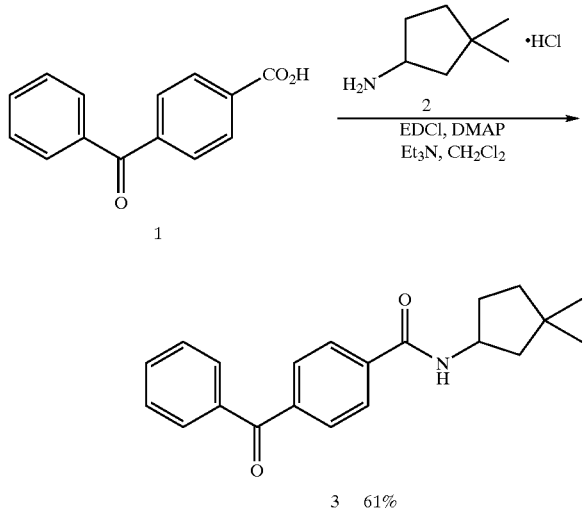

4-Benzoylbenzoic acid (0.20 mmol) and the title B compound of example 1b (0.22 mmol) were dissolved in 1 mL of THF and triethylamine (0.22 mmol) and 4-dimethylamino-pyridine (0.02 mmol) were added. 1-(3-dimethylaminopropyl)-3-ethylcarbodiimide hydrochloride (1.6 ML, 0.15 M in dichloromethane, 0.24 mmol) was added and the mixture was allowed to stand for 48 hours. Purification by preparative HPLC (YMC ODS-A S% 30×250 mm column, 50–90% methanol water with 0.10% TFA gradient over 20 minutes, 25 ml/minute flow) provided 40 mg (61%) of a white solid. $C_{21}H_{23}NO_2$: m/z=322 (M+H).

Example 1d

N-[(3,3-Dimethylcyclopentyl)methyl]-4-(hexyloxy) benzamide

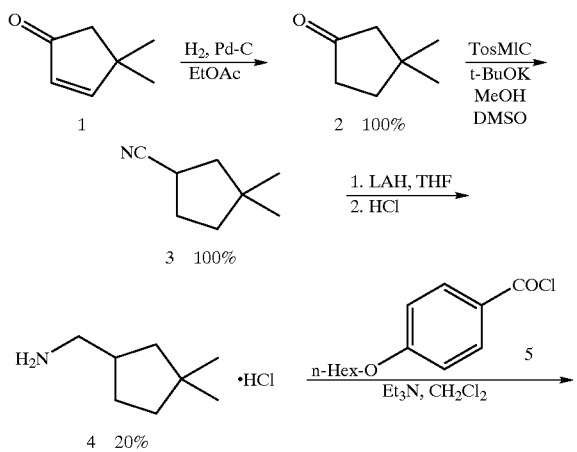

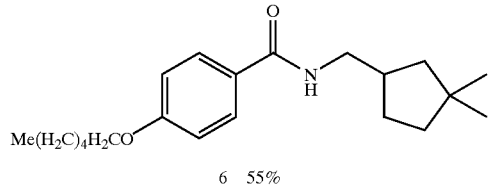

A. 3,3-Dimethylcyclopentanone 4,4-Dimethyl-2-cyclopenten-1-one (1, 1.0 g, 9.08 mmol) was dissolved in 5 mL of ethyl acetate and palladium (10% on carbon, 50 mg) was added. The mixture was stirred under a hydrogen atmosphere (balloon) for 23 hours. The reaction was then filtered through Celite and the Celite washed with ether. The solvent was removed by distillation at atmospheric pressure to provide 1.11 g (>100%) of a clear colorless oil that was used without further purification.

B. 3,3-Dimethylcyclopentanecarbonitrile

Solid potassium t-butoxide (3.57 g, 31.8 mmol) was dissolved in 10 mL of anhydrous dimethylsulfoxide. Tosylmethyl isocyanide (2.13 g, 10.9 mmol) was dissolved in 8 mL of dimethylsulfoxide and added to the potassium-t-butoxide. A thick brown precipitate formed. The ketone (2, assumed 9.08 mmol) was added in 386 μL of anhydrous methanol. The mixture was heated to 45° C. and stirred for 24 hours. The reaction was diluted with water (100 mL), acidified to pH 3, and extracted with pentane. The extracts were dried over magnesium sulfate, filtered and the solvent removed to provide a yellow oil (>100%) that was used without purification.

C. 3,3-Dimethylcyclopentanemethanamine Hydrochloride

The nitrile (3, assumed 9.08 mmol) was dissolved in 10 mL of anhydrous tetrahydrofuran and cooled to 0° C. Lithium aluminum hydride (335 mg, 9.08 mmol) was added and the mixture was stirred for 20 hours. The reaction was then quenched by addition of sodium sulfate decahydrate, filtered through celite and the celite washed with ether. Hydrogen chloride (2.5 mL, 4 M in dioxane) was added and the solvent removed to provide a brown oil. This oil was dissolved in water, filtered and lyophilized to yield 296 mg (20%) of a brown solid.

D. N-[(3,3-Dimethylcyclopentyl)methyl]-4-(hexyloxy) benzamide

The amine hydrochloride (4, 100 mg, 0.61 mmol) was dissolved in 2 mL of dichloromethane. Triethylamine (255 μL, 1.83 mmol) and 4-hexyloxybenzoyl chloride (5, 136 μL, 0.61 mmol) were added and the mixture was stirred for 6 hours at room temperature. The reaction was diluted with ethyl acetate and washed with hydrochloric acid (1.0 M, aq.), sodium bicarbonate (sat'd., aq.) and sodium chloride (sat'd., aq.). The organic layer was dried over magnesium sulfate, filtered and the solvent removed to provide 210 mg of a brown solid. Purification by flash chromatography on silica gel eluting with 5% acetone, hexane provided 111 mg (55%) of a white powder. mp 85–86° C.; Anal. calc'd for $C_{21}H_{33}NO_2$: C, 76.09; H, 10.03; N, 4.23. Found: C, 76.02; H, 10.23; N, 4.20.

Example 1e

N-[(3,3-Dimethylcyclohexyl)methyl]-4-(hexyloxy)benzamide

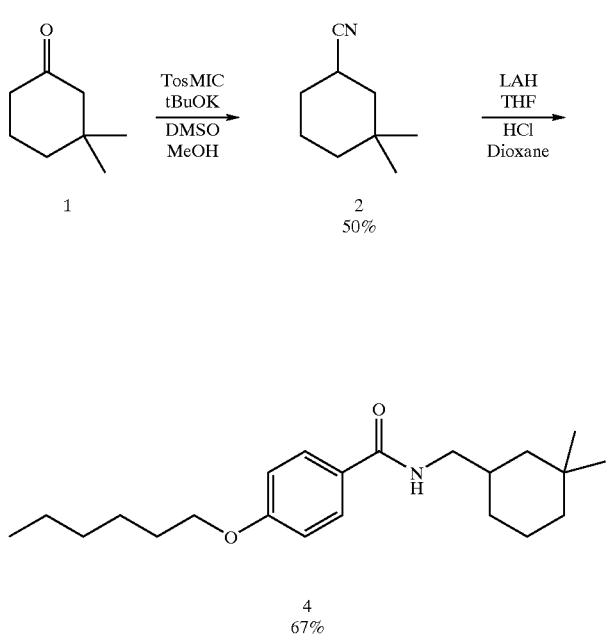

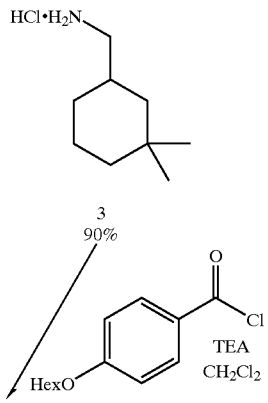

A. 3,3-Dimethylcyclohexanecarbonitrile

Tosylmethyl isocyanide (3.0 g, 15.4 mmol) was dissolved in 15 mL of anhydrous dimethylsulfoxide and the solution was cooled to 5–10° C. in an ice water bath. Potassium tert-butoxide (5.03 g, 44.8 mmol) was then added and the solution turned dark brown in color. The reaction was allowed to warm to room temperature and stirred for 1 hour. A solution of the cyclohexanone (1) (1.62 g, 12.8 mmol) in anhydrous methanol (685 μL) was added to the reaction via syringe and the reaction was stirred at room temperature under argon for 40 hours. The reaction was then diluted with 25 mL of water and placed in an ice water bath and the reaction was made acidic by the dropwise addition of aqueous HCl (6.0 M, aq.). The aqueous phase was extracted 2 times with hexane, and the organic phases were combined and dried over $MgSO_4$, filtered and concentrated to provide 2.24 g of a yellow mixture of oil and solid. The crude mixture was purified by chromatography on silica gel (eluted with 0–50% dichloromethane in hexanes) and the fractions were concentrated and monitored by IR to find 870 mg (50%) of the nitrile product (2) as a transparent oil.

B. 3,3-Dimethylcyclohexanemethanamine Hydrochloride

The nitrile (2) (410 mg, 2.99 mmol) was dissolved in 6 mL of anhydrous tetrahydrofuran and the resulting solution was cooled to 0° C. on an ice water bath. Solid lithium aluminum hydride (114 mg, 3.0 mmol) was then slowly added to the reaction in small portions. Upon full addition, the bath was removed and the reaction was stirred at room temperature under argon for 16 hours. The reaction was then cooled on an ice water bath and solid $Na_2SO_4 \cdot 10\ H_2O$ was slowly added until gas evolution ceased. The reaction was diluted in 10 mL of $Et_2O$ and several drops of water were added to produce a filterable solid. The reaction was then filtered through a pad of Celite and 1.5 mL of 4.0 M HCl in dioxane was added to the filtrate. The cloudy reaction solution was stirred for 15 minutes and then concentrated in vacuo to provide 477 mg (90%) of a white solid.

C. N-[(3,3-Dimethylcyclohexyl)methyl]-4-(hexyloxy)-benzamide

The amine (3) was dissolved in 5 mL of anhydrous dichloromethane and triethylamine (171 μL, 1.23 mmol) was added at room temperature under argon. The solution was cooled in an ice water bath and hexyloxybenzoyl chloride (134 μL, 0.61 mmol) was added via syringe and the reaction was allowed to warm to room temperature and stirred for 64 hours. The reaction was partitioned between HCl (1.0 N, aq) and dichloromethane and the organic phase was washed with $NaHCO_3$ (sat'd, aq.), dried over $MgSO_4$, filtered and concentrated to provide 224 mg of a white solid. The solid was purified by flash chromatography on silica gel eluted with 15% acetone, hexane to provide 142 mg (67%) of the desired amide. Analysis calculated for $C_{22}H_{35}NO_2$: C, 76.48; H, 10.21; N, 4.05. Found: C, 76.42; H, 10.27; N, 3.98.

Example 1f

4-(Hexyloxy)-N-[(2-methylcyclohexyl)methyl]benzamide

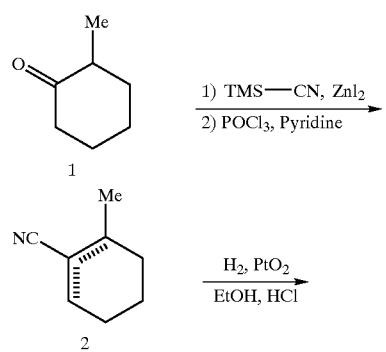

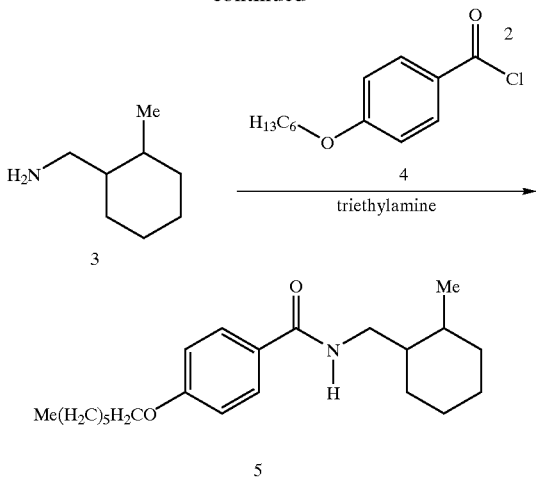

A. 6-Methyl-1-cyclohexenenitrile and 2-methyl-1-cyclohexenenitrile

Trimethylsilyl cyanide (8.0 mL, 60.0 mmol) was added dropwise over a 5 minute period to a suspension of 2-methylcyclopentanone (1) (6.1 mL, 50.0 mmol) and zinc iodide (399 mg, 1.25 mmol) in methylene chloride (25 mL). After stirring for 3 hours, a mixture of phosphorous oxychloride (11.2 mL, 120 mmol) and pyridine (60 mL) was added to the reaction. The reaction was heated at 110° C. for 23 hours and then cooled to room temperature. The reaction was carefully poured onto 250 g of crushed ice, acidified with 6 N HCl (30 mL), and extracted with ether (3×150 mL). The combined organic layers were washed with water (50 mL), saturated $NaHCO_3$ (50 mL), dried ($MgSO_4$) and concentrated by distillation. Vacuum distillation (10 mm Hg) provided 5.56 g of a mixture of 6-methyl-1-cyclohexenenitrile and 2-methyl-1-cyclohexenenitrile (bp 86–91° C.).

B. ((2-Methylcylohexyl)methyl)amine Hydrochloride

The mixture of title A compounds (2.00 g, 16.5 mmol), $PtO_2$ (120 mg), and saturated ethanolic HCl (4.5 mL) in ethanol (75 mL) was shaken under a hydrogen atmosphere (55 psi) on a Parr shaker for 3.5 hours. After purging with nitrogen, the reaction was filtered through Celite AFA. The pad was rinsed with ethanol (3×15 mL) and the combined filtrates were concentrated in vacuo. Trituration of the solid residue with ether (1×50 mL, 2×20 mL) provided 2.29 g (85%) of ((2-methylcylohexyl)methyl)amine hydrochloride as a mixture of isomers.

C. 4-(Hexyloxy)-N-[(2-methylcyclohexyl)methyl] benzamide

To a suspension of title B compound (213 mg, 1.30 mmol) in THF (6 mL) was added triethylamine 0.42 mL, 3.0 mmol). After stirring for 5 minutes, 4-hexyloxybenzoyl chloride (0.223 mL, 1.00 mmol) was added. After stirring for 4 hours, the reaction was filtered through a Celite pad. The pad was rinsed with ether (4×5 mL) and the combined filtrates were concentrated in vacuo. Purification by RP-HPLC (YMC SH-365-10 120A S-110 30×500 mm column, 40 mL/minute, 90:10 methanol/water containing 0.1% TFA)) afforded the title compound as a 1:1 mixture of cis- and trans- isomers (43 mg). MS: (ESI) (m/z) 332.

Using the procedure described for the synthesis of the title B compound of Example 1f ((2-ethylcyclohexyl)-methyl) amine hydrochloride (from 2-ethylcyclohexanone, 71% yield, isomer mixture), ((2-enylcyclohexyl)methyl)amine hydrochloride (from 2-enylcyclohexanone, 44% yield, isomer mixture), ((2-methylcyclopentyl)methyl)amine hydrochloride (from 2-methylcyclopentanone, 49% yield, isomer mixture), and ((2-ethylcyclopentyl)methyl)amine hydrochloride (from 2-ethylcyclopentanone, 42% yield, isomer mixture) were prepared.

Using methodology analogous to that described for the title compounds of Example 1, the compounds of Examples 2 to 20 were prepared.

| Example # | Structure | Characterization |
|---|---|---|
| 2 | 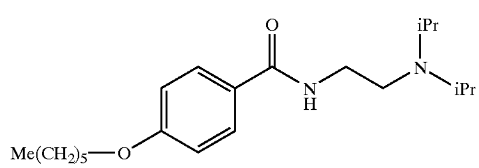 | $C_{21}H_{36}N_2O_2$·HCl: mp 131–134° C. Analysis calculated: C, 65.5; H, 9.69; N, 7.27; Cl. 9.21. Found: C, 65.6; H, 9.79; N, 7.17; Cl, 8.97. |
| 3 | 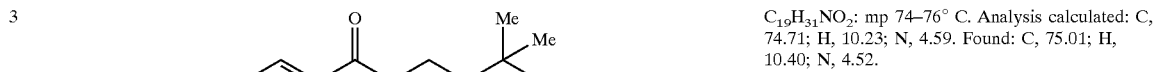 | $C_{19}H_{31}NO_2$: mp 74–76° C. Analysis calculated: C, 74.71; H, 10.23; N, 4.59. Found: C, 75.01; H, 10.40; N, 4.52. |
| 4 | 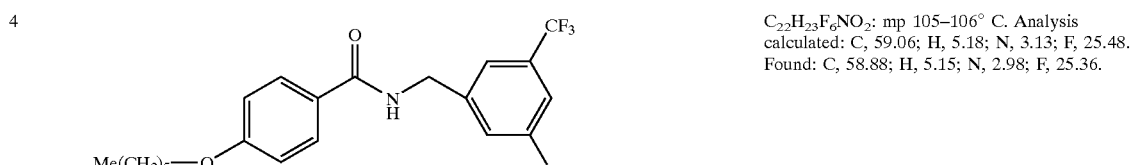 | $C_{22}H_{23}F_6NO_2$: mp 105–106° C. Analysis calculated: C, 59.06; H, 5.18; N, 3.13; F, 25.48. Found: C, 58.88; H, 5.15; N, 2.98; F, 25.36. |

-continued

| Example # | Structure | Characterization |
|---|---|---|
| 5 | (4-hexyloxybenzamide with 3,3-dimethylcyclopentyl) | $C_{20}H_{31}NO_2$: mp 82–83° C. Analysis calculated: C, 75.67; H, 9.84; N, 4.41. Found: C, 75.86; H, 10.10; N, 4.37. |
| 6 | (4-hexyloxybenzamide with tert-pentyl group) | $C_{18}H_{29}NO_2$: m/e = 291. |
| 7 | (4-hexyloxybenzamide with hydroxy-trimethylcyclohexylmethyl) | $C_{23}H_{37}NO_3$: m/e = 375. |
| 7a | (4-hexyloxybenzamide with 2-ethylcyclohexylmethyl) | $C_{22}H_{35}NO_2$ ESI (m/z) 346 Rf (silica, 25% EtOAc/hex) 0.34. |
| 7b | (4-hexyloxybenzamide with 2-phenylcyclohexylmethyl, cis) | $C_{26}H_{35}NO_2$ ESI (m/z) 394 Rf (silica, 25% EtOAc/hex) 0.27. |
| 7c | (4-hexyloxybenzamide with 2-phenylcyclohexylmethyl, trans) | $C_{26}H_{35}NO_2$ ESI (m/z) 394 Rf (silica, 25% EtOAc/hex) 0.28. |
| 7d | (4-hexyloxybenzamide with 2,3,3-trimethylpentyl) | $C_{21}H_{35}NO_2$ ESI (m/z) 334 Rf (silica, 25% EtOAc/hex) 0.39. |
| 7e | (4-hexyloxybenzamide with 3,3-dimethylpentyl) | $C_{21}H_{35}NO_2$ ESI (m/z) 334 Rf (silica, 25% EtOAc/hex) 0.41. |
| 7f | (4-hexyloxybenzamide with (2,2-dimethyl-3-(2-methylpropenyl)cyclopropyl)methyl) | $C_{23}H_{35}NO_2$: ESI (m/z) 358 mp 68.0–69.0° C. Analysis calculated: C, 77.27; H, 9.87; N, 3.92. Found: C, 77.02; H, 10.12; N, 3.74. |

-continued

| Example # | Structure | Characterization |
|---|---|---|
| 7g | (4-pentyloxyphenyl)-C(=O)-NH-CH₂-(2-methylcyclopentyl); 60:40 isomer mixture | $C_{20}H_{31}NO_2$: mp 98.0–100.0° C. Analysis calculated: C, 75.67; H, 9.84; N, 4.41. Found: C, 75.57; H, 10.02; N, 4.26. |
| 7h | (4-pentyloxyphenyl)-C(=O)-NH-CH₂-(2-ethylcyclopentyl); 50:50 trans:cis mixture | $C_{21}H_{33}NO_2 \cdot 0.14\ H_2O$: mp 93.0–95.5° C. Analysis calculated: C, 75.50; H, 10.04; N, 4.19. Found: C, 75.50; H, 10.20; N, 3.94. |
| 7i | (4-hexyloxyphenyl)-C(=O)-NH-CH₂-cyclopentyl | $C_{19}H_{29}NO_2 \cdot 0.17\ H_2O$: mp 107.0–109.5° C. Analysis calculated: C, 74.45; H, 9.65; N, 4.57. Found: C, 74.45; H, 9.89; N, 4.71. |
| 7j | (4-hexyloxyphenyl)-C(=O)-NH-CH₂-(2-phenylcyclopentyl) | $C_{25}H_{33}NO_2$: mp 87.0–88.0° C. Analysis calculated: C, 79.12; H, 8.76; N, 3.69. Found: C, 79.09; H, 8.67; N, 3.58. |
| 7k | (4-pentyloxyphenyl)-C(=O)-NH-CH₂-(2-phenylcyclopentyl) | mp 77.0–78.0° C. ESI (m/z) 380. |
| 8 | 4-biphenyl-C(=O)-NH-CH₂CH₂-C(Me)₃ | $C_{19}H_{23}NO$: mp 126–127° C. Analysis calculated: C, 81.00; H, 8.24; N, 4.98. Found: C, 81.17; H, 8.19; N, 4.93. |
| 9 | 2,3-dimethyl-1H-indole-7-C(=O)-NH-CH₂CH₂-C(Me)₃ | $C_{17}H_{24}N_2O$: m/e = 272. |

-continued
| Example # | Structure | Characterization |
|---|---|---|
| 10 | 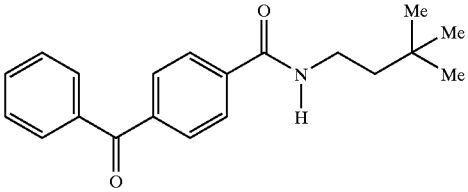 | $C_{20}H_{23}NO_2$: m/e = 309. |
| 10a | 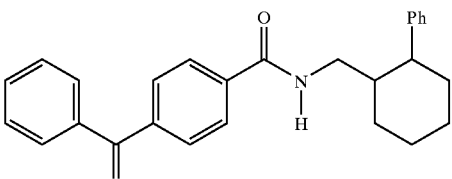<br>ca. 2:1 cis:trans mixture | ESI (m/z) 398 Rf (silica, 25% EtOAc/hex) 0.21. |
| 10b | 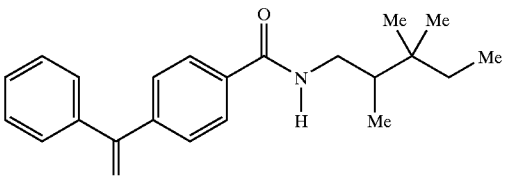 | ESI (m/z) 338 Rf (silica, 25% EtOAc/hex) 0.24. |
| 10c | 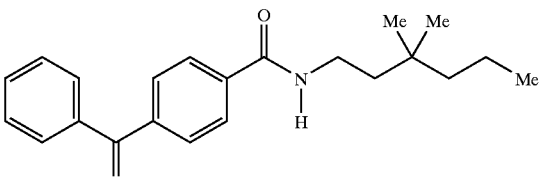 | mp 56.0–57.0° C. ESI (m/z) 358 |
| 10d | 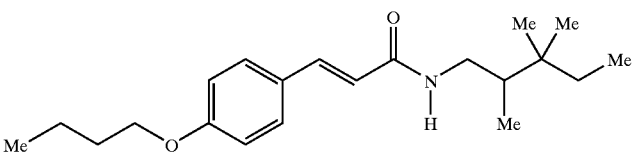 | mp 62.5–64.0° C. ESI (m/z) 332 |
| 10e | 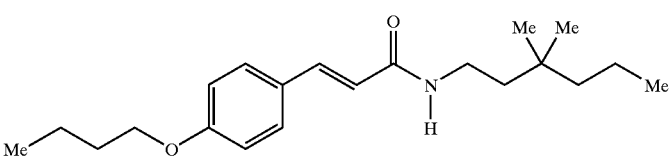 | mp 50.5–51.5° C. ESI (m/z) 332 |
| 10f | 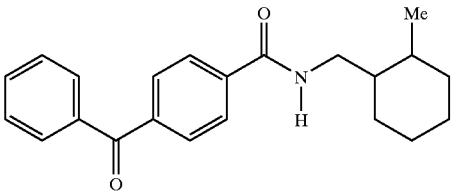<br>ca. 2:1 mixture of isomers | mp 109.5–113.0° C. ESI (m/z) 336 |

-continued

| Example # | Structure | Characterization |
|---|---|---|
| 10g | ca. 1.4:1 mixture of isomers | mp 133.0–133.5° C. ESI (m/z) 350 |
| 10h | 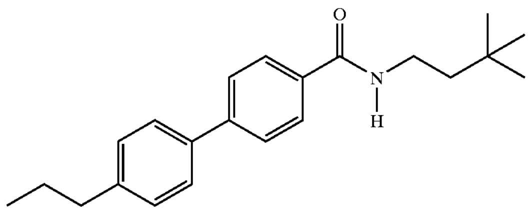 | $C_{22}H_{29}NO_2$: mp 161.0–163.0° C. Analysis calculated: C, 81.69; H, 9.04; N, 4.33. Found: C, 81.65; H, 8.91; N, 4.13. |
| 10i | 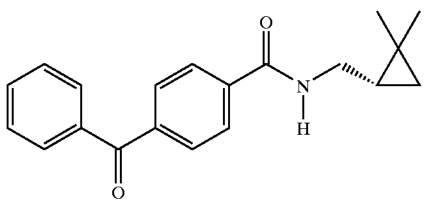 | $C_{20}H_{21}NO_2 \cdot 0.27\ H_2O$: mp 96.9–97.0° C. Analysis calculated: C, 76.94; H, 6.95; N, 4.49. Found: C, 76.94; H, 6.90; N, 4.59. |
| 10j | 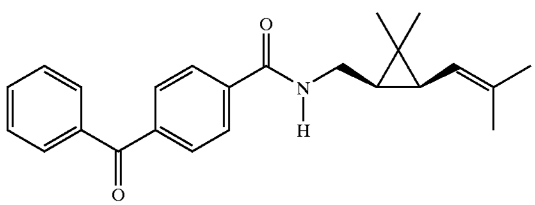 | ESI (m/z) 362 Rf (silica, 25% EtOAc/hex) 0.20. |
| 10k | 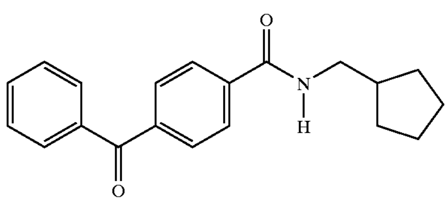 | $C_{20}H_{21}NO_2 \cdot 0.16\ H_2O$: mp 96.0–97.0° C. Analysis calculated: C, 77.40; H, 6.93; N, 4.51. Found: C, 77.40; H, 6.66; N, 4.47. |
| 10l | 60:40 isomer mixture | $C_{22}H_{25}NO_2$: mp 106.0–107.5° C. Analysis calculated: C, 78.77; H, 7.51; N, 4.18. Found. C, 78.53; H, 7.51; N, 3.89. |
| 10l' | 60:40 isomer mixture | $C_{21}H_{23}NO_2$: mp 103.5–106.0° C. Analysis calculated: C, 78.47; H, 7.21; N, 4.36. Found: C, 78.32; H, 7.20; N, 4.29. |

-continued

| Example # | Structure | Characterization |
|---|---|---|
| 10m | 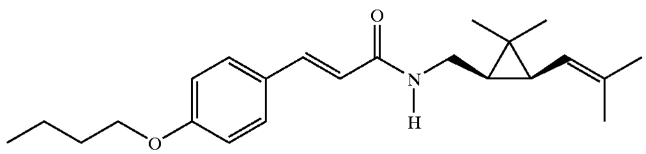 | mp 58.0–59.0° C. ESI (m/z) 356. |
| 10m' | 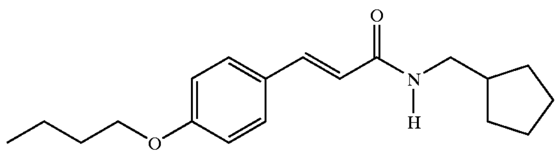 | $C_{19}H_{27}NO_2 \cdot 0.42\ H_2O$: mp 104.0–107.5° C. Analysis calculated: C, 73.86; H, 9.08; N, 4.53. Found: C, 73.86; H, 9.26; N, 4.36. |
| 10n | 60:40 mixture of isomers | $C_{20}H_{29}NO_2 \cdot 0.13\ H_2O$: mp 107.0–110.0° C. Analysis calculated: C, 75.59; H, 9.28; N, 4.41. Found: C, 75.59; H, 9.51; N, 4.79. |
| 10o | 50:50 mixture of isomers | $C_{21}H_{31}NO_2$: mp 90.0–92.5° C. Analysis calculated: C, 76.55; H, 9.48; N, 4.25. Found: C, 76.80; H, 9.73; N, 4.04. |
| 10p | 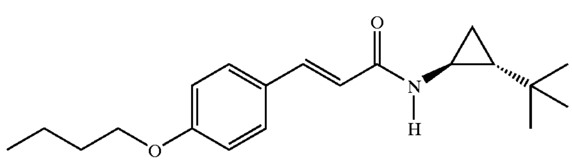 | $C_{20}H_{29}NO_2 \cdot 0.18\ H_2O$: mp 115.5–118.5° C. Analysis calculated: C, 75.38; H, 9.29; N, 4.40. Found: C, 75.38; H, 9.40; N, 4.65. |
| 10q | 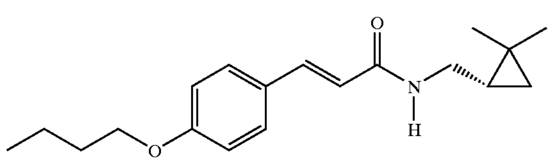 | $C_{19}H_{28}NO_2$: mp 88.5–90.0° C. Analysis calculated: C, 75.46; H, 9.33; N, 4.63. Found: C, 75.72; H, 9.19; N, 4.44. |
| 10r | 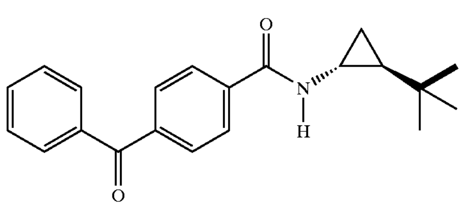 | mp 85.5–87.0° C. ESI (m/z) 322 |
| 10s | 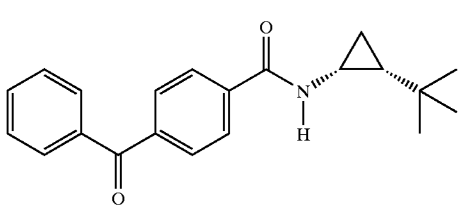 | mp 122.0–125.0° C. ESI (m/z) 322 |

-continued

| Example # | Structure | Characterization |
|---|---|---|
| 10t | 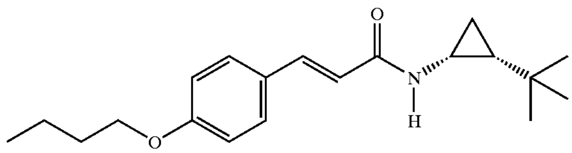 | mp 151.0–153.0° C. ESI (m/z) 316 |
| 10u | 2:1 cis:trans mixture of isomers | $C_{26}H_{25}NO_2 \cdot 0.15\ H_2O$: ESI (m/z) 384. Analysis calculated: C, 80.85; H, 6.60; N, 3.63. Found: C, 80.85; H, 6.33; N, 3.52. |
| 10v | 2:1 cis:trans mixture of isomers | $C_{25}H_{31}NO_2 \cdot 0.19\ H_2O$: ESI (m/z) 378. Analysis calculated: C, 78.83; H, 8.30; N, 3.68. Found: C, 78.83; H, 8.50; N, 3.57. |
| 10w | 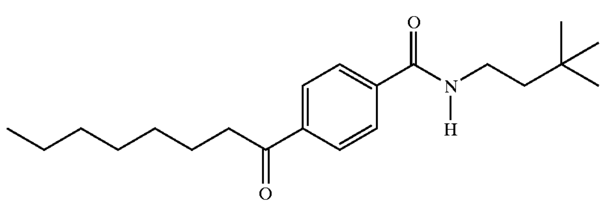 | $C_{21}H_{33}NO_2$: mp 97.0–99.0° C. Analysis calculated: C, 76.09; H, 10.03; N, 4.23. Found: C, 75.81; H, 10.23; N, 4.13. |
| 11 | 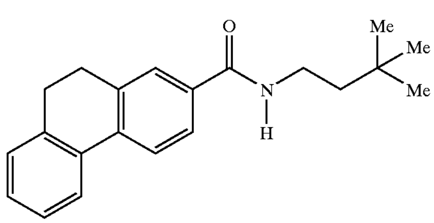 | $C_{21}H_{25}NO$: m/e = 307. |
| 12 | 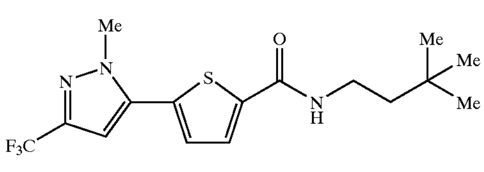 | $C_{16}H_{20}F_3N_3OS$: m/e = 359. |
| 13 | 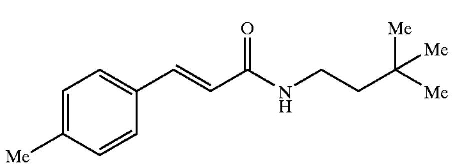 | $C_{16}H_{23}NO$: m/e = 245. |

-continued

| Example # | Structure | Characterization |
|---|---|---|
| 14 | (4-butoxyphenyl)-CH=CH-C(O)-NH-CH₂CH₂-C(Me)₃ | C₁₉H₂₉NO₂: mp 82–84° C. Analysis calculated: C, 75.21; H, 9.63; N, 4.62. Found: C, 75.34; H, 9.44; N, 4.43. |
| 14a | (4-butoxyphenyl)-CH=CH-C(O)-NH-(3,3-dimethylcyclopentyl) | C₂₀H₂₉NO₂: m/z = 316 (M + H) |
| 14b | (4-butoxyphenyl)-CH=CH-C(O)-NH-CH₂-(3,5-bis(trifluoromethyl)phenyl) | C₂₂H₂₁F₆NO₂: m/z 446 (M + H) |
| 14c | (4-butoxyphenyl)-CH=CH-C(O)-NH-CH₂CH₂-C(Me)₃ | MW m/z = 304 (M + H) |
| 14d | (4-propoxyphenyl)-CH=CH-C(O)-NH-CH₂-(2,2-dimethylcyclopentyl) | C₂₁H₃₁F₆NO₂: m/z 330 (M + H) |
| 15 | Me(CH₂)₄-NH-C(O)-(1,4-phenylene)-C(O)-NH-CH₂CH₂-C(Me)₃ | C₁₉H₃₀N₂O₂·0.25 H₂O: mp 221° C. Analysis calculated: C, 70.67; H, 9.52; N, 8.67. Found: C, 70.67; H, 9.58; N, 8.57. |
| 16 | (4-MeOOC-phenyl)-C(O)-NH-CH₂-(3,5-bis(trifluoromethyl)phenyl) | C₁₈H₁₃F₆NO₃: mp 149–150° C. Analysis calculated: C, 54.05; H, 3.35; H, 3.50. Found: C, 53.60; H, 3.07; N, 3.48. |
| 17 | (4-MeOOC-phenyl)-C(O)-NH-CH₂-(2,2-dimethylcyclopentyl) | C₁₇H₂₃NO₃: mp 80–81° C. Analysis calculated: C, 70.56; H, 8.01; N, 4.84. Found: C, 70.27; H, 8.06; N, 4.74. |

| Example # | Structure | Characterization |
|---|---|---|
| 17a | 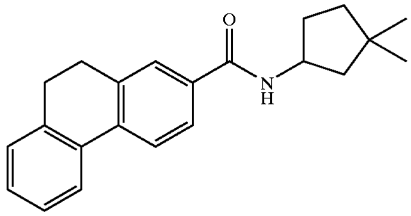 | $C_{22}H_{25}NO$: m/z = 320 (M + H) |
| 17b | 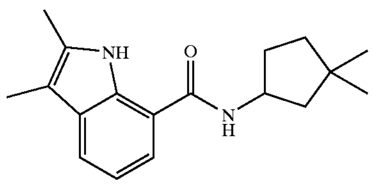 | $C_{18}H_{24}N_2O$: m/z = 285 (M + H) |
| 18 | 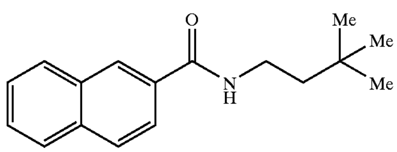 | $C_{17}H_{21}NO$: m/e = 255.18 |
| 18a | 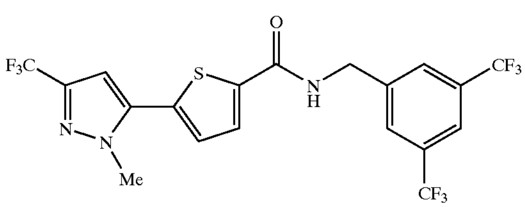 | $C_{19}H_{12}F_9N_3OS$: m/z = 501 (M + H) |
| 18b | 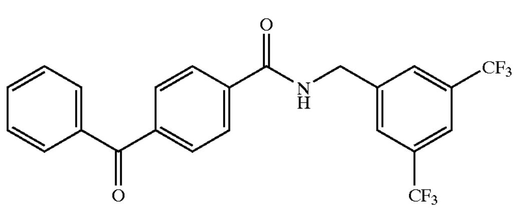 | $C_{23}H_{15}F6NO_2$: m/z = 452 (M + H) |
| 18c | 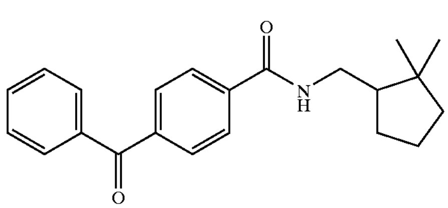 | $C_{22}H_{25}NO_2$: m/z = 336 (M + H) |
| 18d | 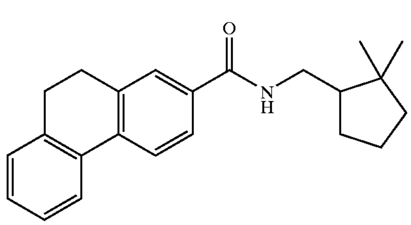 | $C_{23}H_{27}NO$: m/z = 334 (M + H) |

| Example # | Structure | Characterization |
|---|---|---|
| 18e | 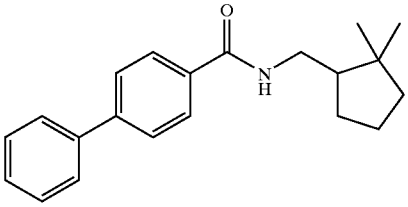 | $C_{21}H_{25}NO$: m/z = 308 (M + H) |
| 19 | 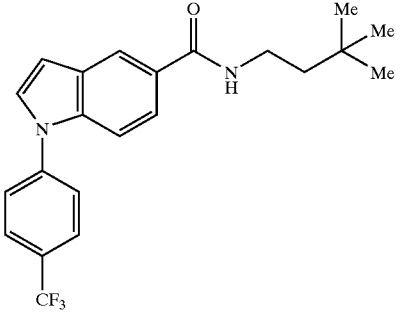 | $C_{22}H_{23}F_3N_2O$: mp 135–137° C. Analysis calculated: C, 68.02; H, 5.97; N, 7.21; F, 14.67. Found: C, 67.78; H, 5.71; N, 7.02; F, 14.67. |
| 19a | 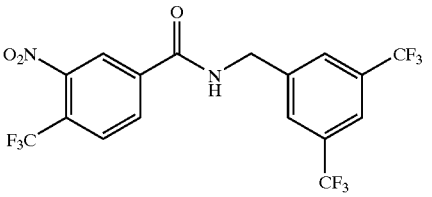 | $C_{17}H_9F_9N_2O_3$: m/z 460 |
| 19b | 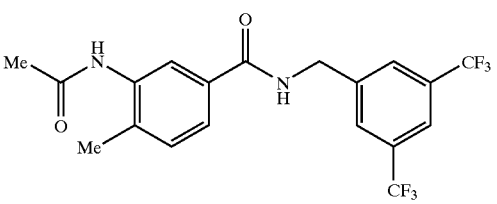 | $C_{19}H_{16}F_6N_2O_2$: m/z 418 |
| 19c | 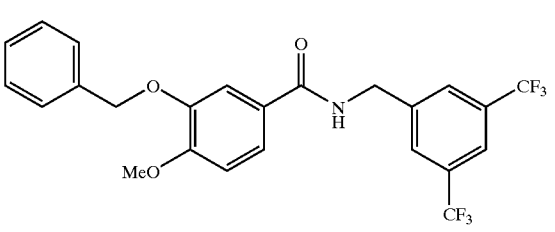 | $C_{24}H_{19}F_6NO_3$: m/z 483 |
| 20 | 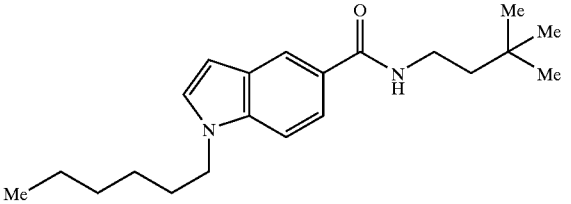 | $C_{21}H_{32}N_2O \cdot 0.32\ H_2O$: mp 86–87° C. Analysis calculated: C, 75.46; H, 9.84; N, 8.38. Found: C, 75.44; H, 9.67; N, 8.27. |
| 20a | 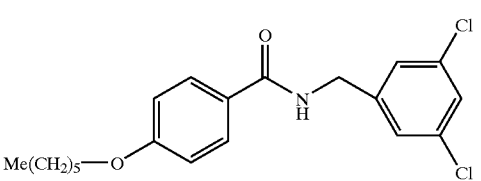 | $C_{20}H_{23}Cl_2NO_2$: mp 84–94° C. Analysis calculated: C, 63.16; H, 6.10; N, 3.68; Cl, 18.64. Found: C, 63.19; H, 5.99; N, 3.55; Cl, 18.58. |

-continued

| Example # | Structure | Characterization |
|---|---|---|
| 20b | [structure: 4-hexyloxybenzamide N-linked to 3,5-dimethoxybenzyl] | $C_{22}H_{29}NO_4$: mp 80–83° C. Analysis calculated: C, 71.13; H, 7.87; N, 3.77. Found: C, 71.12; H, 7.86; N, 3.67. |
| 20c | [structure: 4-hexyloxybenzamide N-linked to 3,5-dimethylbenzyl] | $C_{22}H_{29}NO_2$: mp 116–118° C. Analysis calculated: C, 77.84; H, 8.61; N, 4.13. Found: C, 78.05; H, 8.58; N, 4.10. |
| 20d | [structure: 4-hexyloxybenzamide N-linked to phenethyl] | $C_{22}H_{29}NO_2$: mp 109–111° C. Analysis calculated: C, 77.50; H, 8.36; N, 4.30. Found: C, 77.69; H, 8.47; N, 4.31. |
| 20e | [structure: 4-hexyloxybenzamide N-linked to 2-(3-trifluoromethylphenyl)ethyl] | $C_{22}H_{26}F_3NO_2$: mp 86–87° C. Analysis calculated: C, 67.16; H, 6.66; N, 3.56; F, 14.49. Found C, 67.11; H, 6.62, N, 3.54; F, 14.71. |
| 20f | [structure: 4-hexyloxybenzamide N-linked to 2-(3,5-bis(trifluoromethyl)phenyl)ethyl] | $C_{23}H_{25}F_6NO_2$: mp 86–87° C. Analysis calculated for 0.1 mole hexane: C, 60.30; H, 5.66; N, 2.98; F, 24.25. Found: C, 59.91; H, 5.33; N, 3.00; F, 23.88. |
| 20g | [structure: 3-cyanobenzamide N-linked to 3,5-bis(trifluoromethyl)benzyl] | $C_{17}H_{10}F_6N_2O$: m/z 372 |
| 20h | [structure: 4-chlorobenzamide N-linked to 3,5-bis(trifluoromethyl)benzyl] | $C_{16}H_{10}ClF_6NO$: m/z 381 |

-continued

| Example # | Structure | Characterization |
|---|---|---|
| 20i | 2-CF3-C6H4-C(O)-NH-CH2-[3,5-(CF3)2-C6H3] | C17H10F9NO: m/z 415 |
| 20j | 4-Me2N-C6H4-C(O)-NH-CH2-[3,5-(CF3)2-C6H3] | C18H16F6N2O: m/z 390 |
| 20k | 3-NO2-C6H4-C(O)-NH-CH2-[3,5-(CF3)2-C6H3] | C16H10F6N2O3: m/z 392 |
| 20l | 4-F3CO-C6H4-C(O)-NH-CH2-[3,5-(CF3)2-C6H3] | C17H10F9NO2: m/z 431 |
| 20m | 3-OCF3-C6H4-C(O)-NH-CH2-[3,5-(CF3)2-C6H3] | C17H10F9NO2: m/z 431 |
| 20n | 2-HexO-C6H4-C(O)-NH-CH2-[3,5-(CF3)2-C6H3] | C22H23F6NO2: m/z 447 |
| 20o | 3-OHex-C6H4-C(O)-NH-CH2-[3,5-(CF3)2-C6H3] | C22H23F6NO2: m/z 447 |

| Example # | Structure | Characterization |
|---|---|---|
| 20p | 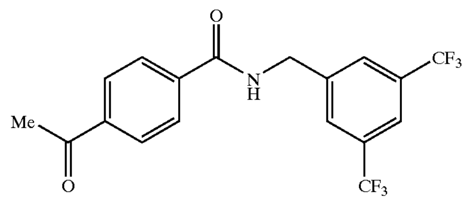 | $C_{18}H_{13}F_6NO_2$: m/z 389 |
| 20q | 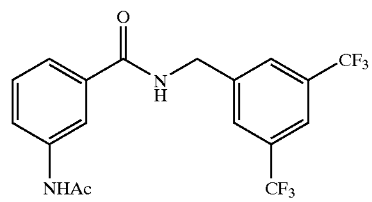 | $C_{18}H_{14}F_6N_2O_2$: m/z 404 |
| 20r | 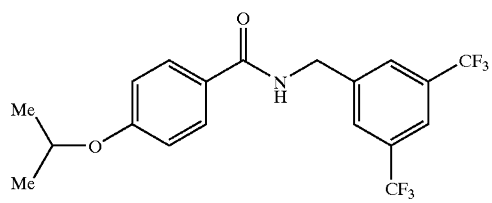 | $C_{19}H_{17}F_6NO_2$: m/z 405 |
| 20s | 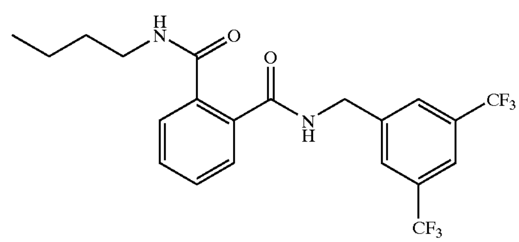 | $C_{21}H_{20}F_6N_2O_2$: m/z 446 |
| 20t | 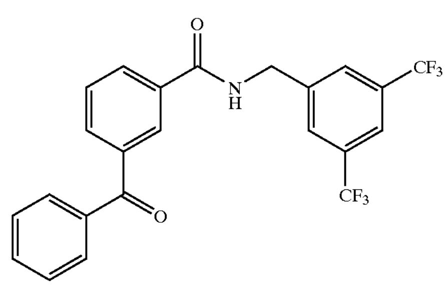 | $C_{23}H_{15}F_6NO_2$: m/z 451 |
| 20u | 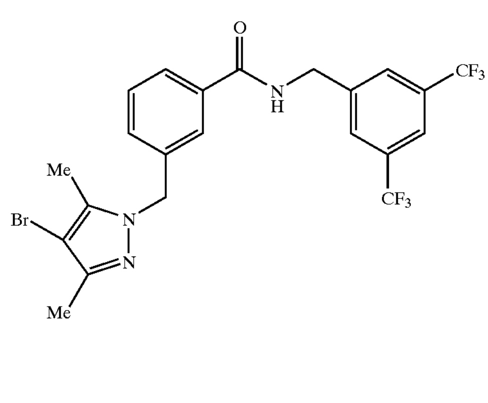 | $C_{22}H_{18}BrF_6N_3O$: m/z 534 |

| Example # | Structure | Characterization |
|---|---|---|
| 20v | 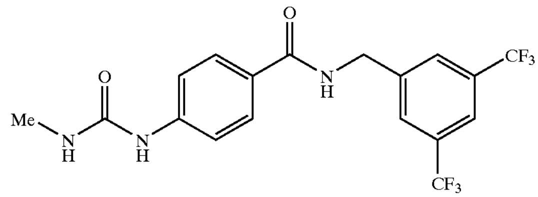 | $C_{18}H_{15}F_6N_3O_2$: m/z 419 |
| 20w | 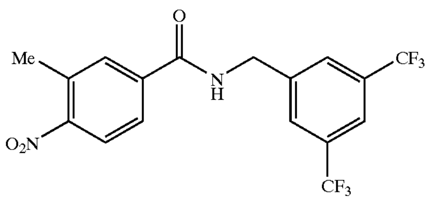 | $C_{17}H_{12}F_6N_2O_3$: m/z 406 |
| 20x | 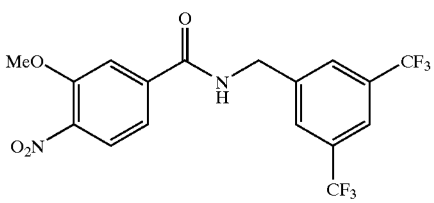 | $C_{17}H_{12}F_6N_2O_4$: m/z 422 |
| 20y | 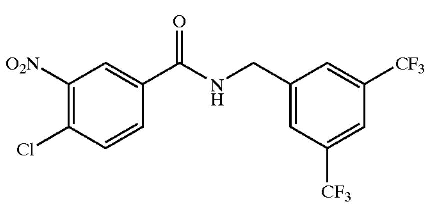 | $C_{16}H_9ClF_6N_2O_3$: m/z 426 |
| 20z | 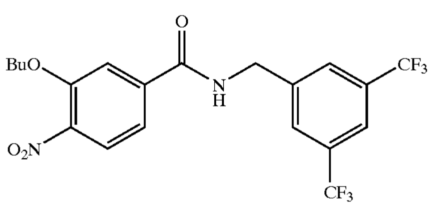 | $C_{20}H_{18}F_6N_2O_4$: m/z 464 |
Example 21
N-(3,3-Dimethylbutyl)-4-(1H-indol-1-yl)benzamide
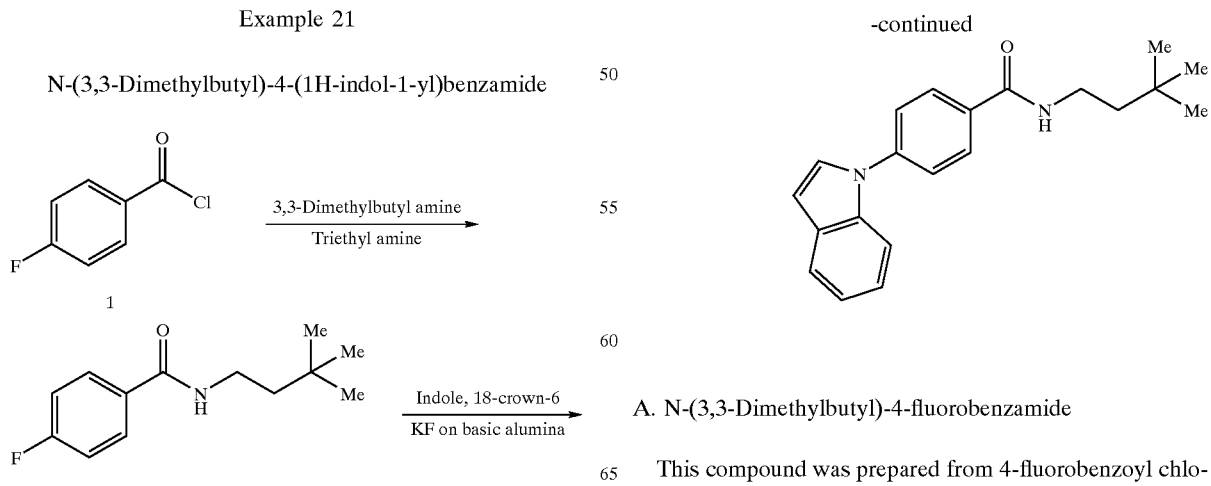
A. N-(3,3-Dimethylbutyl)-4-fluorobenzamide
This compound was prepared from 4-fluorobenzoyl chloride (1) and 3,3-dimethylbutyl amine by the same procedure as described for the title compound of Example 1, part C.

B. N-(3,3-Dimethylbutyl)-4-(1H-indol-1-yl)benzamide

Compound 2 (186 mg, 0.83 mmol) and indole (127 mg, 1.08 mmol) were dissolved in dimethylsulfoxide (8 mL). 18-Crown-6 (66 mg, 0.25 mmol) and 37% by weight KF on basic alumina were added and the reaction mixture was heated at 120° C. for 4 days. The reaction was cooled to room temperature, diluted with ethyl acetate and washed with brine. The organic layer was dried over magnesium sulfate and the solvent was removed to yield an orange oil. Purification by flash chromatography on silica gel eluting with 10% ethyl acetate in hexane provided a tan solid (180 mg, 67%): mp 51–54° C. Analysis calculated for $C_{21}H_{24}N_2O$: C, 78.72; H, 7.55; N, 8.74. Found: C, 78.59; H, 7.41; N, 8.69.

Using methodology analogous to that described for the title compound of Example 21, the compounds of Examples 22 and 23 were prepared.

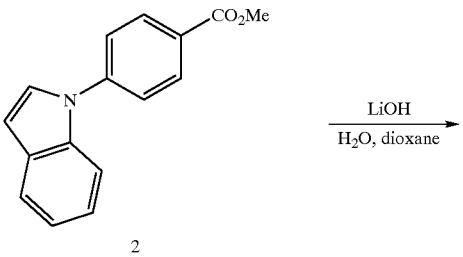

| Example # | Structure | Characterization |
|---|---|---|
| 22 | 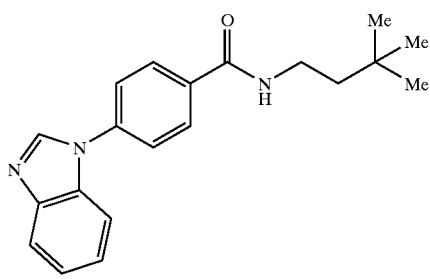 | $C_{20}H_{23}N_3O \cdot 0.8H_2O$: mp 134–135° C. Analysis calculated: C, 71.53; H, 7.38; N, 12.51. Found: C 71.42; H, 6.98; N, 12.43. |
| 23 | 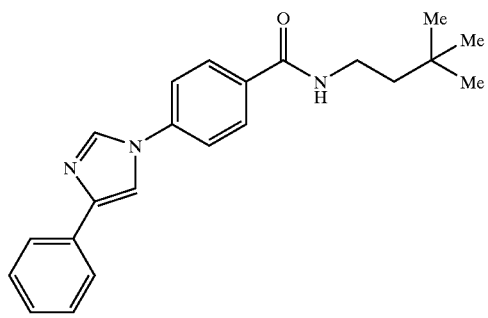 | $C_{22}H_{25}N_3O \cdot 0.55H_2O$: mp 170–171° C. Analysis calculated: C, 73.94; H, 7.36; N, 11.76. Found: C, 73.94; H, 6.97; N, 11.74. |

Example 23a

N-(3,3-Dimethylcyclopentyl)-4-(1H-indol-1-yl)benzamide

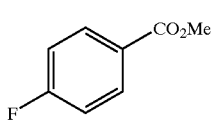 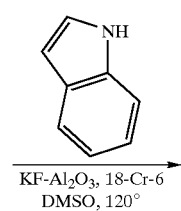

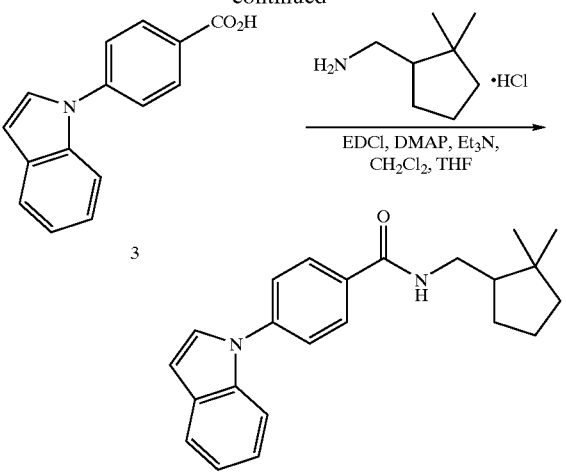

A. 4-(1H-Indol-1-yl)benzoic Acid Methyl Ester

Ethyl-4-fluorobenzoate (4 mL, 27.3 mmol) and indole (3.51 g, 30 mmol) were dissolved in 50 mL of dimethylsulfoxide (DMSO). Potassium fluoride (37% on basic alumina, 12.8 g) and 18-crown-6 (720 mg, 2.73 mmol) were added and the mixture was heated to 120° C. for 24 hours. The reaction was diluted with ethyl acetate and washed with hydrochloric acid (1.0 M, aq.), sodium bicarbonate (sat'd., aq.) and sodium chloride (sat'd., aq.). The organic layer was dried over magnesium sulfate, filtered and the solvent removed. Purification by flash chromatography on silica gel eluted with 5% ethyl acetate, hexane provided 1.45 g (20%) of a white solid B. 4-(1H-Indol-1-yl)benzoic Acid The ester (2, 1.4 g, 5.23 mmol) was dissolved in 45 mL of dioxane. Lithium hydroxide (15.8 mL, 15.8 mmol) was added and the mixture was stirred for 4 hours. The reaction was diluted with water and washed with ethyl acetate. The aqueous phase was acidified with HCl and extracted with ethyl acetate. The organic layer was dried over magnesium sulfate, filtered and the solvent removed to provide 1.04 g (83%) of a pale yellow solid. mp 222–224° C.

C. N-(3,3-Dimethylcyclopentyl)-4-(1H-indol-1-yl) benzamide

The acid (3, 0.20 mmol) and the amine compound 3 from Example 1 (0.22 mmol) were dissolved in 1 mL of THF and triethylamine (0.22 mmol) and 4-dimethylaminopyridine (0.02 mmol) were added. 1-(3-dimethylaminopropyl)-3-ethylcarbodiimide hydrochloride (1.6 mL, 0.15 M in dichloromethane, 0.24 mmol) was added and the mixture was allowed to stand for 48 hours. Purification by preparative HPLC (YMC ODS-A 5S 30×250 mm column, 50–90% methanol water with 0.10% TFA gradient over 20 minutes, 25 mL/minute flow) provided 50 mg (72%) of a white solid. $C_{23}H_{26}N_2O$: m/z=347 (M+H).

The following compounds can be prepared using methodology analogous to that described for the title compound of Example 23a above.

Example 24

4-(3-Butyl-1,2,4-oxadiazol-5-yl)-N-(3,3-dimethylbutyl)benzamide

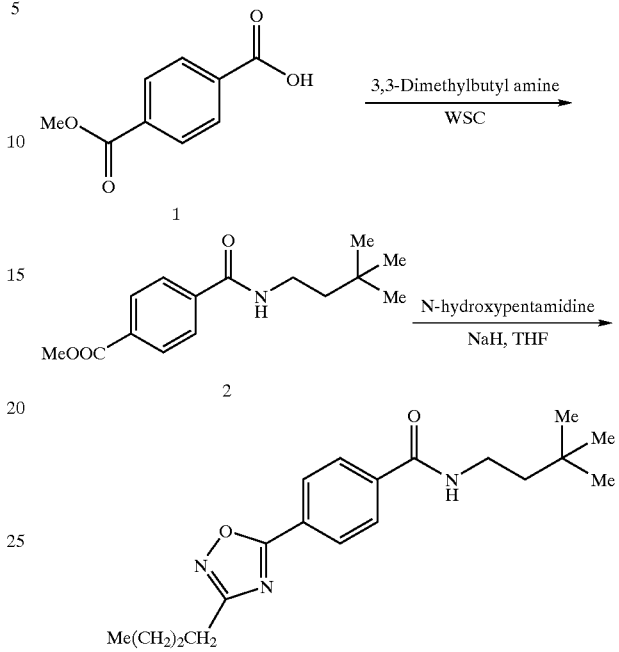

A. N-(3,3-Dimethylbutyl)-4-fluorobenzamide

A solution of mono-methylterephthalate (1) (260 mg, 1.44 mmol) in DMF (3 mL) under argon at room temperature was treated with 3,3-dimethylbutylamine (145 mg, 1.43 mmol), ethyl-3-(3-dimethylamino)propyl carbodiimide hydrochloride (420 mg, 1.41 mmol) and hydroxybenzotriazole monohydrate (192 mg, 1.42 mmol) and stirred overnight. The reaction mixture was diluted with ethyl acetate and washed with 10% citric acid, water, sodium bicarbonate, water and brine. The dried (anhydrous magnesium sulfate) organic fraction was concentrated and the residue was purified by

| Example # | Structure | Characterization |
|---|---|---|
| 23b | 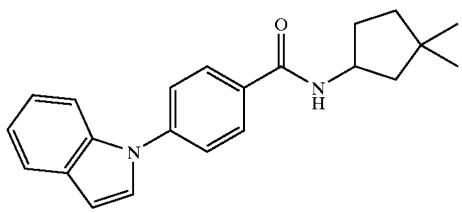 | $C_{22}H_{24}N_2O$: m/z = 333 (M + H) |
| 23c | | $C_{22}H_{31}N_3O \cdot 0.67H_2O$:<br>Analysis calculated: C, 72.29; H, 8.92; N, 11.5.<br>Found: C, 72.29; H, 9.11; N, 11.34. | flash chromatography on silica gel, eluting with ethyl acetate/hexanes (1:4) to give compound 2 (327 mg, mp 88–90° C.).

B. 4-(3-Butyl-1,2,4-oxadiazol-5-yl)-N-(3,3-dimethylbutyl)-benzamide

A solution of compound 2 (137 mg, 0.52 mmol) and N-hydroxypentamidine (75 mg, 0.65 mmol) in dimethylformamide (1.5 mL) under argon at 0–5° C. was treated with sodium hydride (45 mg, 60%/m.o., 1.14 mmol) and allowed to stir at room temperature for 4 hours. The mixture, diluted with ethyl acetate, was washed with water and brine. The organic fraction was dried (anhydrous magnesium sulfate) and concentrated in vacuo to give a solid. Flash chromatography on silica gel, eluting with ethyl acetate/hexanes (1:4) gave the title compound (140 mg, 81%): mp 95–97° C. Analysis calculated for $C_{19}H_{27}N_3O_2$: C, 69.27; H, 8.26; N, 12.75. Found: C, 69.01; H, 8.29; N, 12.50.

Using methodology analogous to that described for the title compound of Example 24, the compounds of Examples 25 to 29 were prepared.

| Example # | Structure | Characterization |
|---|---|---|
| 25 | 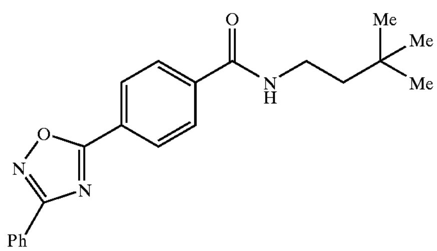 | $C_{21}H_{23}N_3O_2$: mp 169–170° C.<br>Analysis calculated: C, 72.18; H, 6.63; N, 12.03.<br>Found: C, 71.92; H, 6.63; N, 11.63. |
| 26 | 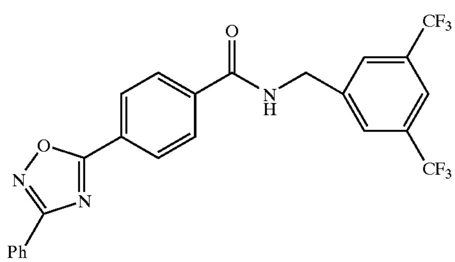 | $C_{24}H_{15}F_6N_3O_2$: mp 209–210° C.<br>Analysis calculated: C, 58.66; H, 3.08; N, 8.55; F, 23.20.<br>Found: C, 58.52; H, 3.08; N, 8.51; F, 22.85. |
| 27 | 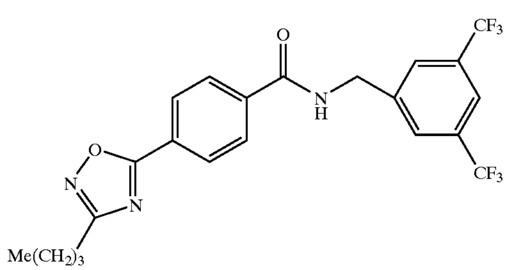 | $C_{22}H_{19}F_6N_3O_2$: mp, 156–157° C.<br>Analysis calculated: C, 56.56; H, 4.15; N, 8.99; F, 23.45.<br>Found: C, 56.23; H, 3.88; N, 8.89; F, 23.28. |
| 27a | 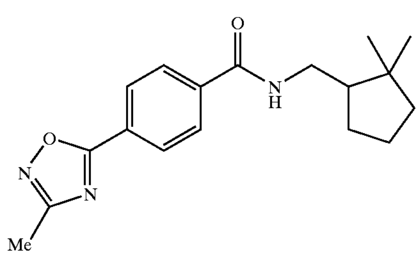 | $C_{18}H_{23}N_3O_2$: mp 155–156° C.<br>$[\alpha]_D = +22.8°$ (c = 1.02, $CHCl_3$).<br>Analysis calculated for 0.56 mole water: C, 66.83; H, 7.52; N, 12.99.<br>Found: C, 66.82; H, 7.01; N, 12.57. |
| 27b | 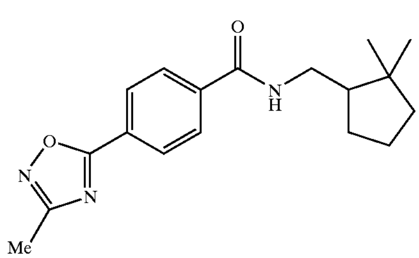 | $C_{18}H_{23}N_3O_2$: mp 155–156° C.<br>$[\alpha]_D = -22.8°$ (c = 1.00, $CHCl_3$).<br>Analysis calculated: C, 68.98; H, 7.40; N, 13.41.<br>Found: C, 68.78; H, 6.85; N, 13.10. |

-continued

| Example # | Structure | Characterization |
|---|---|---|
| 27c | 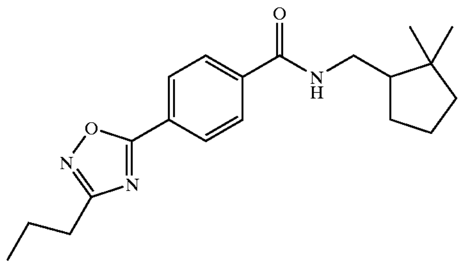 | $C_{20}H_{27}N_3O_2$: mp 88–90° C.<br>$[\alpha]_D = +21.4°$ (c = 0.49, CHCl$_3$).<br>Analysis calculated: C, 70.35; H, 7.97; N, 12.31.<br>Found: C, 70.09; H, 7.91; N, 12.17. |
| 27d | 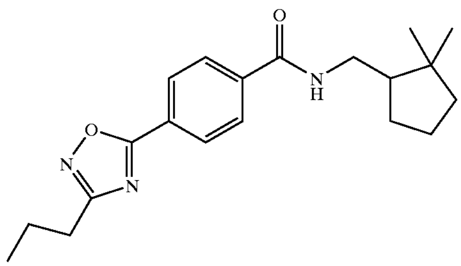 | $C_{20}H_{27}N_3O_2$: mp 88–90° C.<br>$[\alpha]_D = -21.6°$ (c = 0.50, CHCl$_3$).<br>Analysis calculated: C, 70.35; H, 7.97; N, 12.31.<br>Found: C, 70.14; H, 7.84; N, 12.09. |
| 27e | 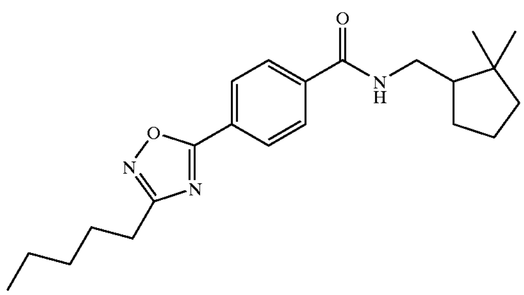 | $C_{20}H_{27}N_3O_2$: mp 94–95° C.<br>$[\alpha]_D = +18.8°$ (c = 0.32, CHCl$_3$).<br>Analysis calculated: C, 71.51; H, 8.46; N, 11.37.<br>Found: C, 71.33; H, 8.49; N, 11.29. |
| 27f | 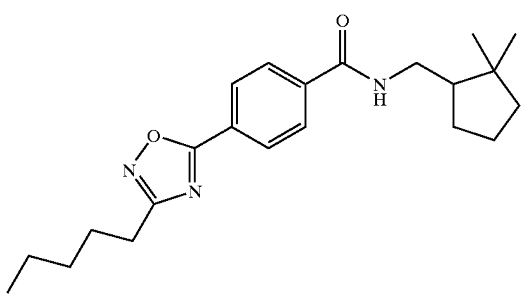 | $C_{20}H_{27}N_3O_2$: mp 94–95° C.<br>$[\alpha]_D = +19.5°$ (c = 0.41, CHCl$_3$).<br>Analysis calculated: C, 71.51; H, 8.46; N, 11.37.<br>Found: C, 71.60; H, 8.47; N, 11.20. |
| 27g | 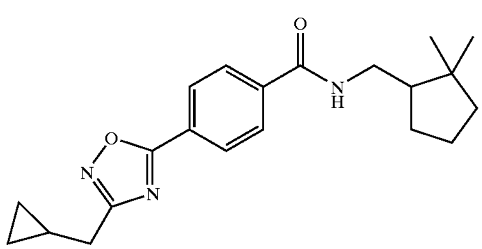 | $C_{21}H_{27}N_3O_2$: mp 116–117° C.<br>$[\alpha]_D = +16.6°$ (c = 0.35, CHCl$_3$).<br>Analysis calculated: C, 71.36; H, 7.70; N, 11.89.<br>Found: C, 71.57; H, 7.81; N, 11.76. |

| Example # | Structure | Characterization |
|---|---|---|
| 27h | 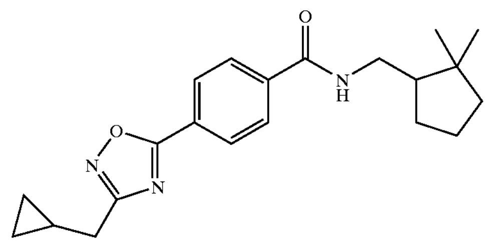 | $C_{20}H_{27}N_3O_2$: mp 94–95° C.<br>$[\alpha]_D = -17.6°$ (c = 0.33, CHCl$_3$).<br>Analysis calculated: C, 71.51; H, 8.46; N, 11.37.<br>Found: C, 71.29; H, 7.68; N, 11.78. |
| 27i | 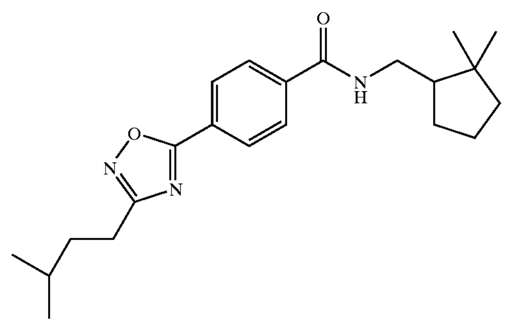 | $C_{22}H_{31}N_3O_2$: mp 92–93° C.<br>$[\alpha]_D = +18.4°$ (c = 0.25, CHCl$_3$).<br>Analysis calculated: C, 71.51; H, 8.46; N, 11.37.<br>Found: C, 71.37; H, 8.33; N, 11.14. |
| 27j | 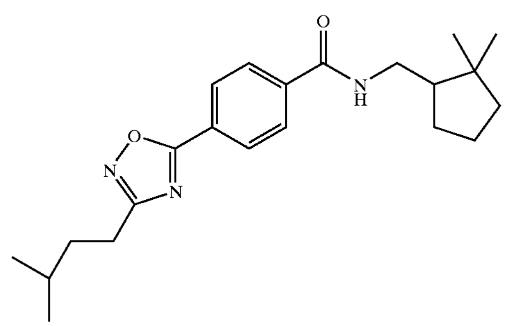 | $C_{22}H_{31}N_3O_2$: mp 94–95° C.<br>$[\alpha]_D = -17.0°$ (c = 0.20, CHCl$_3$).<br>Analysis calculated: C, 71.51; H, 8.46; N, 11.37.<br>Found: C, 71.51; H, 8.56; N, 11.30. |
| 27k | 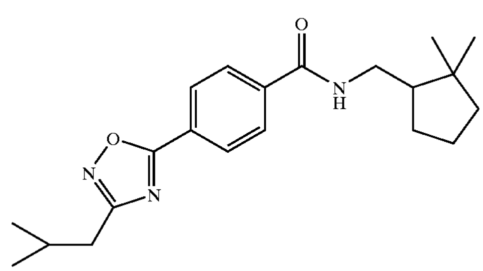 | $C_{21}H_{29}N_3O_2$: mp 114–115° C.<br>$[\alpha]_D = +18.1°$ (c = 0.43, CHCl$_3$).<br>Analysis calculated: C, 70.96; H, 8.22; N, 11.82.<br>Found: C, 70.83; H, 8.30; N, 11.63. |
| 27l | 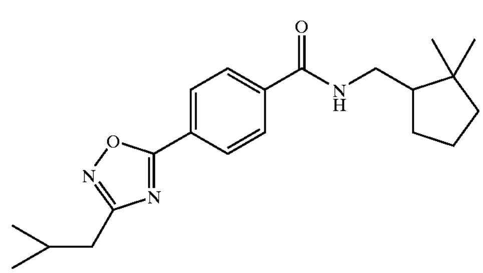 | $C_{21}H_{29}N_3O_2$: mp 116–117° C.<br>$[\alpha]_D = -18.0°$ (c = 0.20, CHCl$_3$).<br>Analysis calculated: C, 70.96; H, 8.22; N, 11.82.<br>Found: C, 70.80; H, 8.22; N, 11.70. |

| Example # | Structure | Characterization |
|---|---|---|
| 27m | 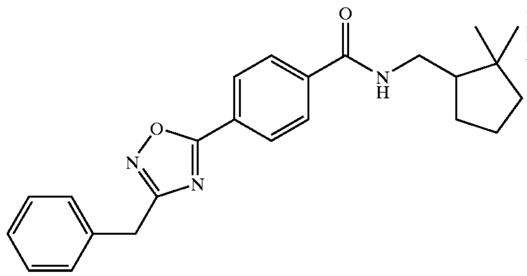 | $C_{24}H_{27}N_3O_2 \cdot 0.16H_2O \cdot 0.03$EtOAc: mp 138–139° C. $[\alpha]_D = +15.1°$ (c = 0.37, CHCl$_3$). Analysis calculated: C, 73.25; H, 7.02; N, 10.62. Found: C, 73.04; H, 6.96; N, 10.45. |
| 27n | 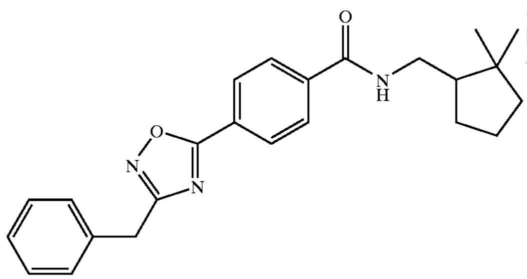 | $C_{24}H_{27}N_3O_2$: mp 139–140° C. $[\alpha]_D = -15.6°$ (c = 0.23, CHCl$_3$). Analysis calculated: C, 74.01; H, 6.99; N, 10.79. Found: C, 73.73; H, 6.77; N, 10.54. |
| 27o | 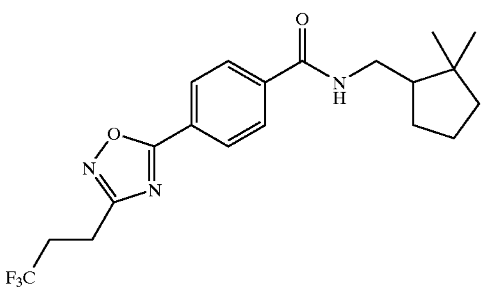 | $C_{20}H_{24}F_3N_3O_2$ $[\alpha]_D = +11.8°$ (c = 0.49, CHCl$_3$). m/s MW = 395.18 |
| 27p | 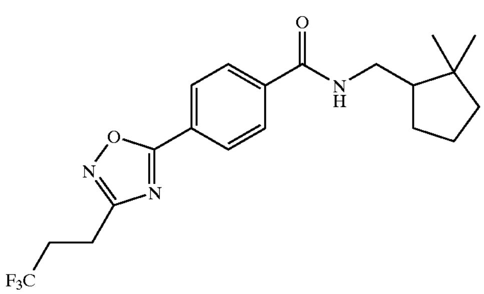 | $C_{20}H_{24}F_3N_3O_2$ $[\alpha]_D = -13.7°$ (c = 0.90, CHCl$_3$). m/s MW = 395.18 |
| 27q | 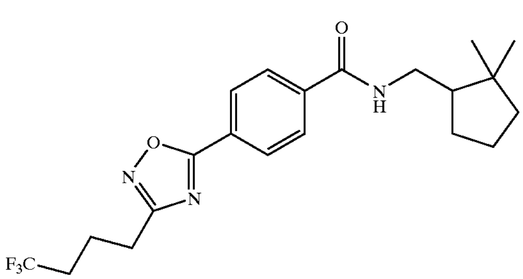 | $C_{21}H_{26}F_3N_3O_2$: mp 83–84° C. $[\alpha]_D = +15.6°$ (c = 0.23, CHCl$_3$). Analysis calculated: C, 61.60; H, 6.40; N, 10.26; F, 13.92. Found: C, ; H, ; N, ; F, . |

-continued

| Example # | Structure | Characterization |
|---|---|---|
| 27r | 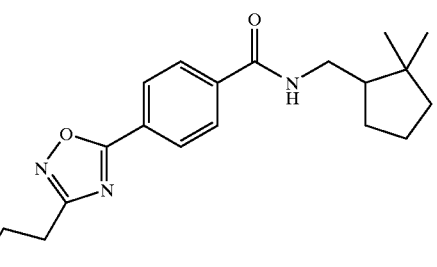 | C$_{21}$H$_{26}$F$_3$N$_3$O$_2$: mp 83–84° C.<br>[α]$_D$ = −15.0° (c = 0.36, CHCl$_3$).<br>Analysis calculated: C, 61.60; H, 6.40; N, 10.26; F, 13.92.<br>Found: C, 6.49; N, 10.19; F, 13.66. |
| 27s | 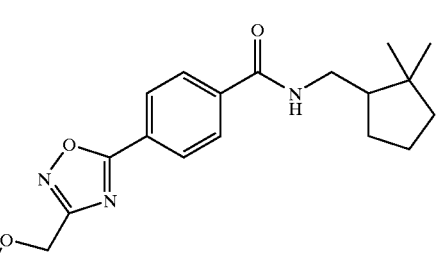 | C$_{20}$H$_{24}$F$_3$N$_3$O$_3$: mp ° C.<br>[α]$_D$ = +13.8° (c = 0.24, CHCl$_3$).<br>Analysis calculated: C, 58.39; H, 5.88; N, 10.21; F, 13.85.<br>Found: C, ; H, ; N, ; F, . |
| 27t | 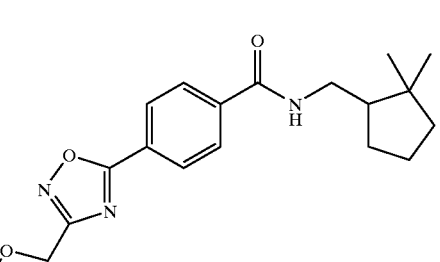 | C$_{20}$H$_{24}$F$_3$N$_3$O$_3$: mp 83–84.5° C.<br>[α]$_D$ = −17.5° (c = 0.24 CHCl$_3$).<br>Analysis calculated: C, 58.39; H, 5.88; N, 10.21; F, 13.85.<br>Found: C, 58.52; H, 5.95; N, 10.16; F, 13.34. |
| 28 | 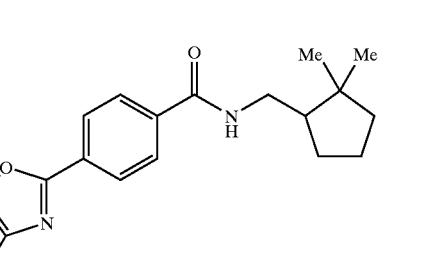 | C$_{21}$H$_{29}$N$_3$O2.0.3 hexanes: mp 74–76° C.,<br>[α]$_D$ = +17.3° (c = 0.11, CHCl$_3$).<br>Analysis calculated: C, 71.81; H, 8.78; N, 11.02.<br>Found: C, 71.85; H, 8.69; N, 11.09. |
| 29 | 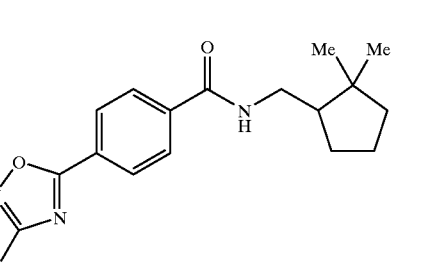 | C$_{21}$H$_{29}$N$_3$O2.0.3 hexanes: mp 74–76° C.,<br>[α]$_D$ = −20° (c = 0.12, CHCl$_3$).<br>Analysis calculated: C, 71.81; H, 8.78; N, 11.02.<br>Found: C, 71.85; H, 8.69; N, 11.09. |

Example 29a 4-(5-Butyl-1,2,4-oxadiazol-3-yl)-N-(3,3-dimethylbutyl)benzamide

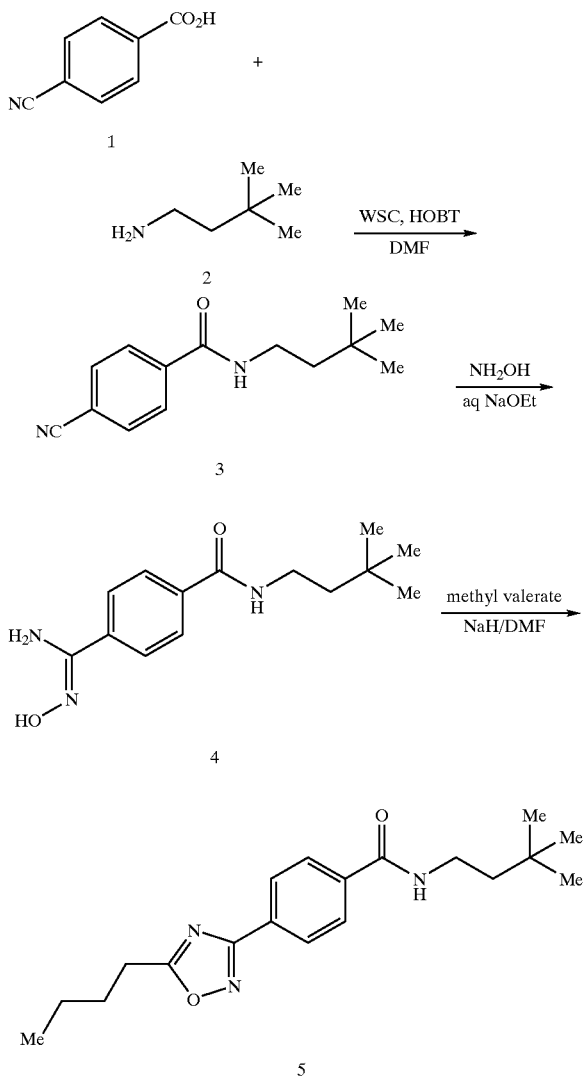

A. 4-Cyano-N-(3,3-Dimethylbutyl)benzamide

A solution of methyl 4-cyanobenzoic acid (1, 735 mg, 5.0 mmol) in 12 mL of DMF under argon at room temperature was treated 3,3-dimethylbutylamine (2, 505 mg, 5.0 mmol), ethyl-3-(3-dimethylamino)-propyl carbodiimide hydrochloride (1.5 g, 5.0 mmol) and hydroxybenzotriazole monohydrate (685 mg, 5.0 mmol) and stirred overnight. The reaction mixture was diluted with ethyl acetate and washed with 10 percent citric acid, water, dilute sodium bicarbonate, water and brine. The dried (anhydrous magnesium sulfate) organic fraction was concentrated to give 1.5 g. Flash chromatography on 150 mL of EM-60 silica gel, eluting with ethyl acetate/hexanes (1:4) gave the title compound (1.06 g, 92%), mp 154–157° C. Analysis calculated for $C_{14}H_{18}N_2O$: C, 73.01; H, 7.88; N, 12.16. Found: C, 73.00; H, 7.92; N, 12.17.

B. 4-[Amino(hydroxyimino)methyl]-N-(3,3-dimethylbutyl)benzamide

A slurry of hydroxylamine hydrochloride (100 mg, 1.4 mmole) in water (0.1 mL) at room temperature was treated with sodium ethoxide in ethanol (prepared from 33 mg sodium in 2 mL ethanol) and the title A compound and stirred for 48 hours. The mixture was diluted with a small amount of ethanol and filtered to remove solids. The filtrate was concentrated, redissolved in ethanol, cooled in ice and filtered. The filtrate was concentrated and dried under high vacuum over $P_2O_5$ to give 348 mg hydroxyamidine product 4. m/z $MH^+$ @ 264, MW=263.

C. 4-(5-Butyl-1,2,4-oxadiazol-3-yl)-N-(3,3-dimethylbutyl)-benzamide

A solution of the title B compound (200 mg, 0.76 mmol) and methyl valerate (90 mg, 0.78 mmol) in 2 mL of dimethylformamide under argon at 0–5° C. was treated with sodium hydride (33 mg, 60%/m.o., 0.82 mmol) and allowed to stir at room temperature overnight. The mixture, diluted with ethyl acetate, was washed with water and brine. The organic fraction was dried (anhydrous magnesium sulfate) and concentrated. Flash chromatography on 150 mL of EM-60 silica gel, eluting with ethyl acetate/hexanes (1:4) gave the desired compound (145 mg, 58%), mp 78–80° C. Analysis calculated for $C_{19}H_{27}N_3O_2$: C, 69.27; H, 8.26; N, 12.75. Found: C, 69.14; H, 8.37; N, 12.71.

Using the above methodology, the following compounds were prepared.

| Example # | Structure | Characterization |
|---|---|---|
| 29b | 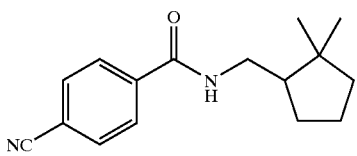 | $C_{16}H_{20}N_2O$: mp 156–158.5° C. Analysis calculated: C, 74.97; H, 7.86; N, 10.93;. Found: C, 74.87; H, 7.99; N, 10.79. |

| Example # | Structure | Characterization |
|---|---|---|
| 29c | 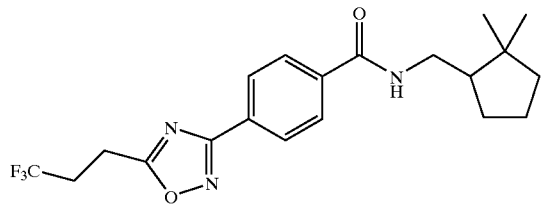 | $C_{20}H_{24}F_3N_3O_2$: mp 116–118° C.<br>$[\alpha]_D = +16.8°$ (c = 0.88 CHCl$_3$).<br>Analysis calculated: C, 60.75; H, 6.12; N, 10.63; F, 14.41.<br>Found: C, 60.57; H, 6.22; N, 10.48; F. 14.02. |
| 29d | 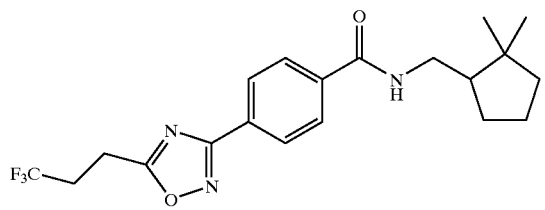 | $C_{20}H_{24}F_3N_3O_2$: mp 116–118° C.<br>$[\alpha]_D = -16.9°$ (c = 0.96 CHCl$_3$).<br>Analysis calculated: C, 60.75; H, 6.12; N, 10.63; F, 14.41.<br>Found: C, 60.87; H, 6.21; N, 10.45; F. 14.10. |
| 29e | 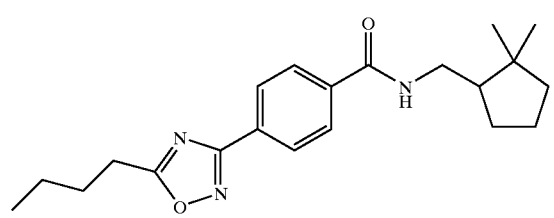 | $C_{21}H_{29}N_3O_2 \cdot 0.1H_2O$ mp 86–88° C.<br>$[\alpha]_D = +20.1°$ (c = 0.63 CHCl$_3$).<br>Analysis calculated: C, 70.60; H, 8.24; N, 11.76.<br>Found: C, 70.57; H, 8.49; N, 11.26. |
| 29f | 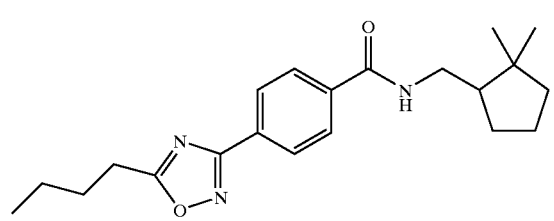 | $C_{21}H_{29}N_3O_2$: mp 86–88° C.<br>$[\alpha]_D = +18.1°$ (c = 0.63 CHCl$_3$).<br>Analysis calculated: C, 70.96; H, 8.22; N, 11.82.<br>Found: C, 70.76; H, 8.49; N, 11.57. |
| 29g | 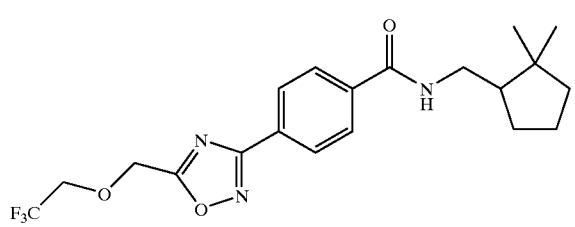 | $C_{20}H_{24}F_3N_3O_3$: mp 73–75° C.<br>$[\alpha]_D = +17.6°$ (c = 0.75 CHCl$_3$).<br>Analysis calculated: C, 58.39; H, 5.88; N, 10.21; F, 13.85.<br>Found: C, 58.51; H, 5.87; N, 10.02; F, 13.49. |
| 29h | 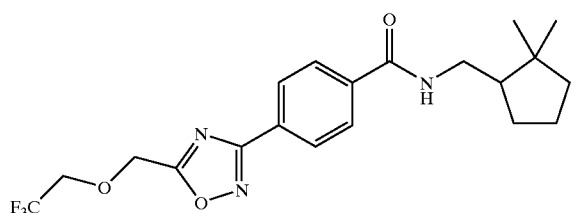 | $C_{20}H_{24}F_3N_3O_3$: mp 73–75° C.<br>$[\alpha]_D = -17.2°$ (c = 0.89 CHCl$_3$).<br>Analysis calculated: C, 58.39; H, 5.88; N, 10.21; F, 13.85.<br>Found: C, 57.98; H, 5.90; N, 9.87; F, 13.45. |

Example 29i 4-(2-Butyl-1H-imidazol-4-yl)-N-[(2,2-dimethylcyclopentyl)-methyl]benzamide

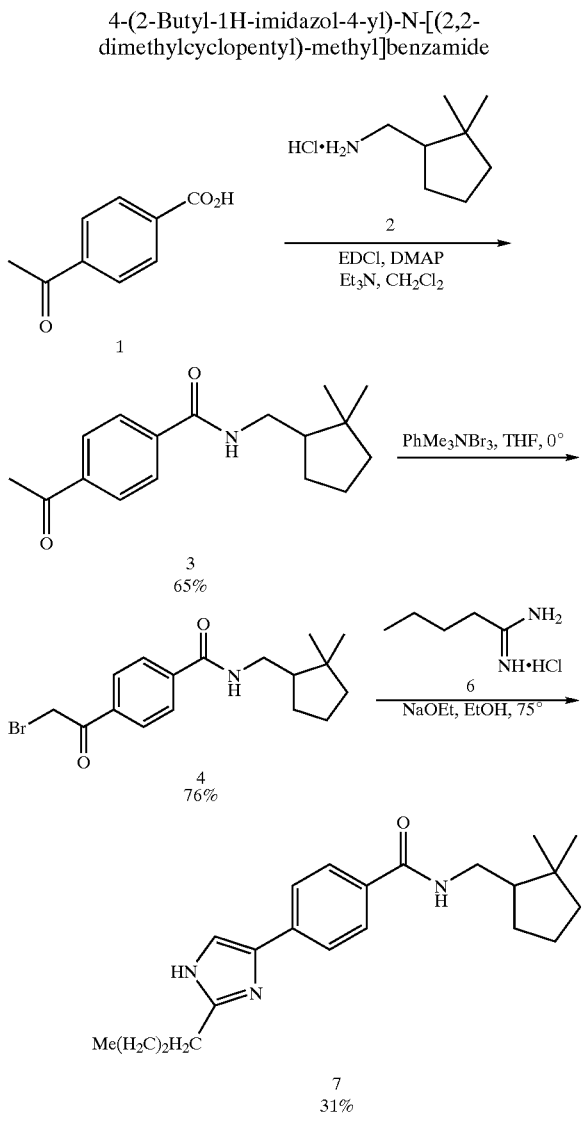

A. 4-Acetyl-N-[(2,2-dimethylcyclopentyl)methyl]benzamide

4-Acetylbenzoic acid (200 mg, 1.20 mmol) and amine 2 (from Example 1, 199 mg, 1.22 mmol) were dissolved in 5 mL of dichloromethane and triethylamine (187 μL, 1.34 mmol) and 4-dimethylaminopyridine (15 mg, 0.12 mmol) were added. 1-(3-dimethylaminopropyl)-3-ethylcarbodiimide hydrochloride (398 mg, 1.34 mmol) was added and the mixture was stirred for 18 hours. The reaction was diluted with ethyl acetate and washed with hydrochloric acid (1.0 M, aq.), sodium bicarbonate (sat'd., aq.) and sodium chloride (sat'd., aq.). The organic layer was dried over magnesium sulfate, filtered and the solvent removed to yield 216 mg (65%) of a white solid.

B. 4-(Bromoacetyl)-N-[(2,2-dimethylcyclopentyl)-methyl]benzamide

The amide 3 (160 mg, 0.585 mmol) was dissolved in 3 mL of tetrahydrofuran (THF) and cooled to 0° C. Phenyltrimethyl-ammonium tribromide (220 mg, 0.585 mmol) was dissolved in 1 mL of THF and added dropwise. The reaction was allowed to warm to room temperature and stir for 22 hours. The mixture was quenched with water and extracted with ethyl acetate. The organic layer was dried over magnesium sulfate, filtered and the solvent removed to yield 230 mg of a tan solid. Purification by flash chromatography on silica gel eluted with 30% ethyl acetate, hexane provided 157 mg (76%) of a white solid.

C. 4-(2-Butyl-1H-imidazol-4-yl)-N-[(2,2-dimethylcyclopentyl)-methyl]benzamide

A solution of n-pentamidine hydrochloride (180 mg, 1.32 mmol) was dissolved in 1 mL of ethanol and sodium ethoxide (2 M in ethanol, 0.66 mL, 1.32 mmol) was added and the mixture was heated to 75° C. The title B compound (155 mg, 0.440 mmol) was dissolved in 1.5 mL of ethanol and added in small portions over 30 minutes. The reaction was stirred for 4 hours, quenched with sodium bicarbonate and the aqueous layer was extracted with ethyl acetate. The organic extracts were dried over magnesium sulfate, filtered and the solvent removed to provide 173 mg of a brown solid. Purification by flash chromatography on silica gel eluted with 70% ethyl acetate, hexane provided 49 mg (31%) of a white solid, mp 98–105° C.; Analysis calculated for $C_{22}H_{31}N_3O \cdot 0.59 H_2O$: C, 72.57; H, 8.91; N, 11.54. Found: C, 72.56; H, 9.00; N, 11.39.

Example 29j

N-(3,3-Dimethylbutyl)-1-[4-(trifluoromethyl)phenyl]-1H-indole-5-carboxamide

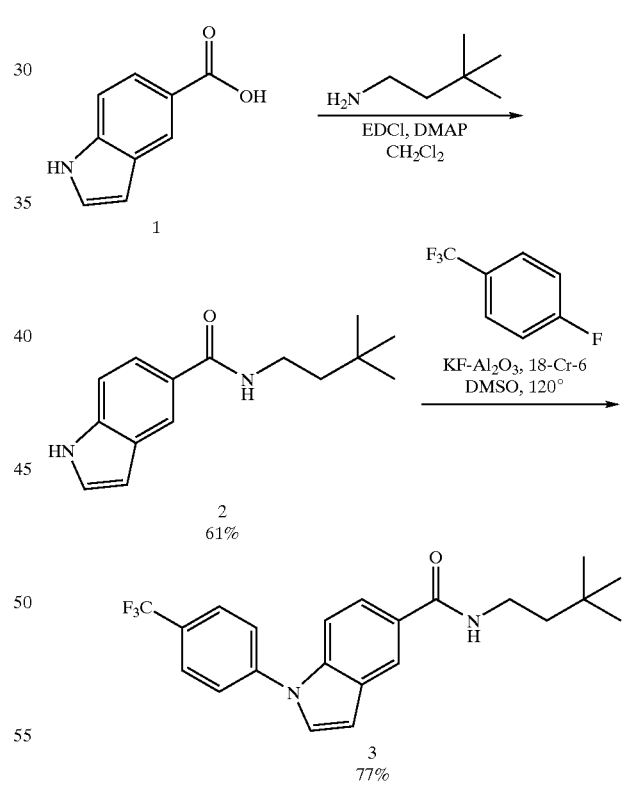

A. N-(3,3-Dimethylbutyl)-1H-indole-5-carboxamide

Indole-5-carboxylic acid (322 mg, 2.00 mmol), 3,3-dimethylbutylamine (296 μL, 2.20 mmol) and 4-dimethylaminopyridine (24 mg, 0.20. mmol) were suspended in 10 mL of dichloromethane and 5 mL of N,N-dimethylformamide. 1-(3-Dimethylaminopropyl)-3-ethylcarbodiimide hydrochloride (EDCI, 653 mg, 2.2 mmol) was added and the mixture stirred for 16 hours. The reaction was diluted with ethyl acetate and washed with hydrochloric acid (1.0 M, aq.), sodium bicarbonate and brine. The organic layer was dried over magnesium sulfate, filtered and the solvent removed to yield a white solid (448 mg). Recrystallization from hexane provided pale yellow needles which were dissolved in ether, filtered and the solvent removed to provide 300 mg (61%) of an off white solid, mp 132–133° C.; Analysis calculated for $C_{15}H_{20}N_2O \cdot 0.10\ H_2O$: C, 73.20; H, 8.27; N, 11.38. Found: C, 73.17; H, 8.25; N, 11.20.

B. N-(3,3-Dimethylbutyl)-1-[4-(trifluoromethyl)phenyl]-1H-indole-5-carboxamide

The title A compound (40 mg, 0.16 mmol) and 4-fluorobenzotrifluoride (42 μL, 0.33 mmol) were dissolved in 2 mL of dimethylsulfoxide. 18-Crown-6 (9 mg, 0.03 mmol) and 37% by weight KF on basic alumina (51 mg, 0.33 mmol) were added and the mixture was heated to 120° C. for 4 days. The reaction was cooled to room temperature, diluted with ethyl acetate and washed with sodium chloride (sat'd., aq.). The organic layer was dried over magnesium sulfate, filtered and the solvent removed to yield 57 mg of a yellow solid. Purification by flash chromatography on silica gel eluted with 15% acetone, hexane provided 49 mg (77%) of a white solid. mp 135–137° C.; Analysis calculated for $C_{22}H_{23}F_3N_2O$: C, 68.02; H, 5.97; N, 7.21; F, 14.67. Found: C, 67.78; H, 5.71; N, 7.02; F, 14.67.

Example 29k

N-(3,3-Dimethylbutyl)-1-(1-oxohexyl)-1H-indole-5-carboxamide

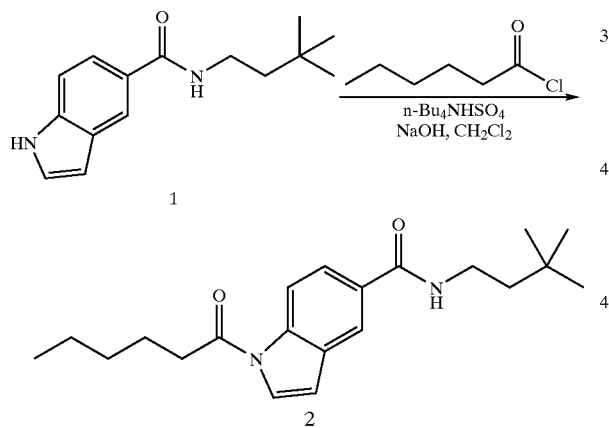

The title A compound of example 29j (44 mg, 0.18 mmol) and tetrabutylammonium hydrogen sulfate (6 mg, 0.02 mmol) were dissolved in 1 mL of dichloromethane. Powdered sodium hydroxide (18 mg, 0.45 mmol) and hexanoyl chloride (38 μL, 0.27 mmol) were added and the mixture was stirred for 2 hours. The reaction was diluted with ethyl acetate and washed with 1N hydrochloric acid, sodium bicarbonate and brine. The organic layer was dried over magnesium sulfate, filtered and the solvent removed to yield 58 mg of a white solid. Purification by flash chromatography on silica gel eluting with 20% acetone, hexane provided 52 mg (84%) of a white solid. mp 136–138° C.; Analysis calculated for $C_{21}H_{30}N_2O_2$: C, 73.65; H, 8.83; N, 8.18. Found: C, 73.53; H, 8.94; N, 8.13.

Example 29k'

4-(3-Butyl-1,2,4-oxadiazol-5-yl)-N-[(2-methylcyclohexyl)methyl]benzamide

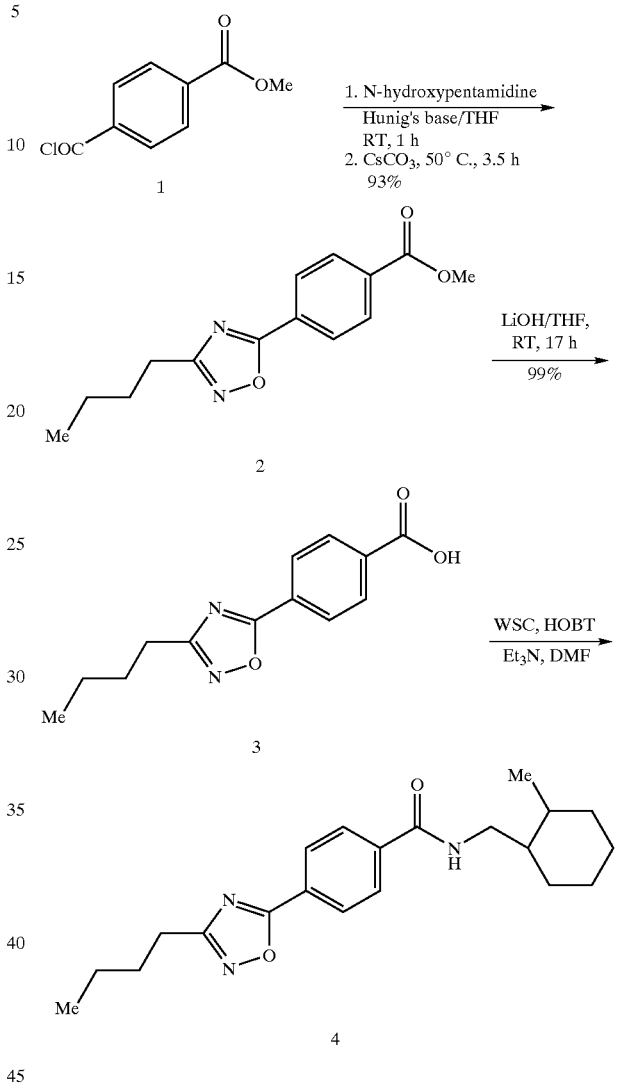

A. 4-(3-Butyl-1,2,4-oxadiazol-5-yl)benzoic Acid Methyl Ester

Diisopropylethylamine (1.1 ml, 6.0 mmol) was added to a solution of terephthalic acid, monomethyl ester chloride (1.0 g, 5.0 mmol) and N-hydroxypentamidine (0.70 g, 6.0 mmol) in THF (8 mL). After stirring at ambient temperature for 1 hour, cesium carbonate (3.6 g, 11 mmol) was added and the reaction was stirred at 50° C. After stirring at 50° C. for 3.5 hours, the reaction was transferred to a separatory funnel with $CH_2Cl_2/H_2O$. The aqueous layer was acidified with 1N HCl to pH 1 and extracted with $CH_2Cl_2$ (3×40 mL). The combined organic layers were dried ($MgSO_4$) and concentrated in vacuo. Flash chromatography (silica, 50 mm dia, 10% EtOAc/hexane) afforded 1.2 g (93%) of methyl (3-butyl-1,2,4-oxadiazol-5-yl)benzoate.

B. 4-(3-Butyl-1,2,4-oxadiazol-5-yl)benzoic Acid

Lithium hydroxide (1.0 N, 9.8 ml, 9.8 mmol) was added to a stirring solution of the title A compound (1.2 g, 4.6 mmol) in THF (45 mL). After stirring at ambient temperature for 17 hours, the reaction was evaporated in vacuo. Water was added and the solution acidified with 1 N HCl. The resulting solid was collected, washed with $H_2O$, and dried under high vacuum over P₂O₅ to afford 1.1 g (99%) of (3-butyl-1,2,4-oxadiazol-5-yl)benzoic acid.

C. 4-(3-Butyl-1,2,4-oxadiazol-5-yl)-N-[(2-methylcyclohexyl)-methyl]benzamide

A solution of ((2-methylcyclohexyl)methyl)amine hydrochloride, prepared according to Example 1f, part B (104 mg, 0.633 mmol), title B compound (130 mg, 0.528 mmol), HOBT hydrate (86 mg), triethylamine (0.15 mL, 1.1 mmol), and 1-(3-dimethylaminopropyl)-3-ethylcarbodiimide hydrochloride (WSC, 121 mg, 0.633 mmol) in DMF (5 mL) was stirred for 17 hours. The reaction was diluted with ether (25 mL); washed with 0.3 N HCl (3×7 mL), and saturated NaHCO₃ (10 mL); dried (MgSO₄) and concentrated in vacuo. Purification by HPLC provided the title compound as a 1:1 mixture of isomers: MS: (ESI) m/z 356.

Using the procedure described for example 29k, the following compounds were prepared.

| Example # | Structure | Characterization |
|---|---|---|
| 29l | ca 1:1 mixture of cis:trans | ESI (m/z) 370<br>Rf (silica, 25% EtOAc/hex) 0.25. |
| 29m | trans isomer | mp 141.5–142.0° C.<br>ESI (m/z) 418 |
| 29n | 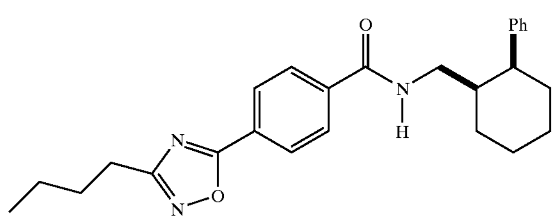 | mp 162.0–162.5° C.<br>ESI (m/z) 418 |
| 29o | 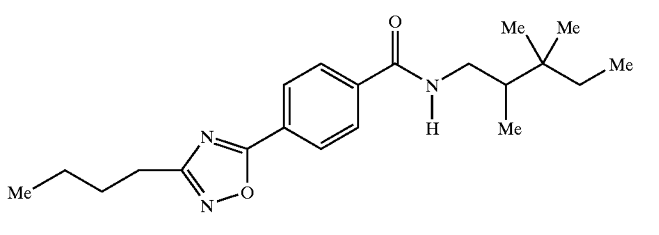 | mp 79.0–79.5° C.<br>ESI (m/z) 358 |
| 29p | 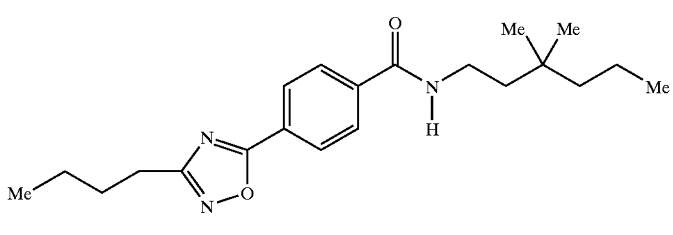 | mp 50.0–52.0° C.<br>ESI (m/z) 358 |

-continued

| Example # | Structure | Characterization |
|---|---|---|
| 29q | 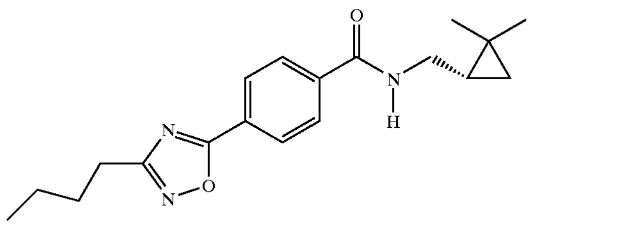 | $C_{19}H_{25}N_3O_2$: mp 98.0–99.5° C.<br>Analysis calculated: C, 69.70; H, 7.70; N, 12.83.<br>Found: C, 69.70; H, 7.88; N, 12.68. |
| 29r | 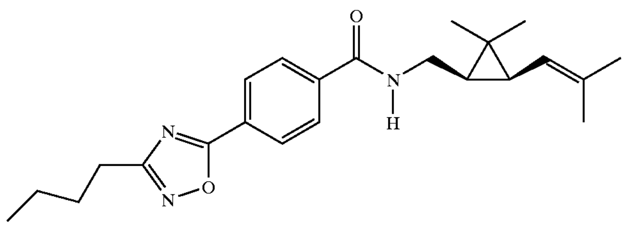 | $C_{23}H_{31}N_3O_2 \cdot 0.09H_2O$: mp 59.0–60.0° C.<br>Analysis calculated: C, 72.10; H, 8.20; N, 10.97.<br>Found: C, 72.10; H, 8.49; N, 10.84. |
| 29s | 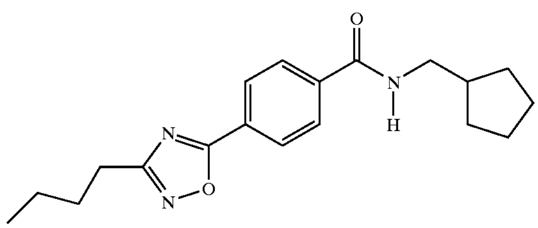 | $C_{19}H_{25}N_3O_2$: mp 127.0–128.5° C.<br>Analysis calculated: C, 69.70; H, 7.70; N, 12.83.<br>Found: C, 69.53; H, 7.93; N, 12.64. |
| 29t | 60:40 isomer mixture | $C_{20}H_{27}N_3O_2$: mp 111.0–113.0° C.<br>Analysis calculated: C, 70.35; H, 7.97; N, 12.31.<br>Found: C, 70.24; H, 8.20; N, 12.27. |
| 29u | 50:50 isomer mixture | $C_{21}H_{29}N_3O_2$: mp 121.0–124.5° C.<br>Analysis calculated: C, 70.95; H, 8.22; N, 11.82.<br>Found: C, 71.00; H, 8.40; N, 11.99. |
| 29v | 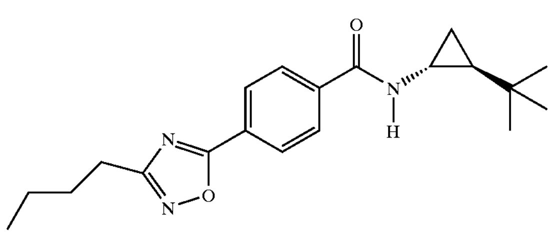 | mp 105.0–107.0° C.<br>ESI (m/z) 342 |

| Example # | Structure | Characterization |
|---|---|---|
| 29w | 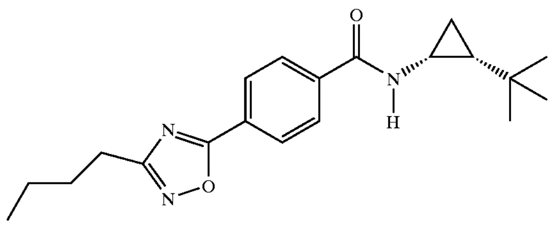 | mp 132.0–133.5° C.<br>ESI (m/z) 342 |
| 29x | 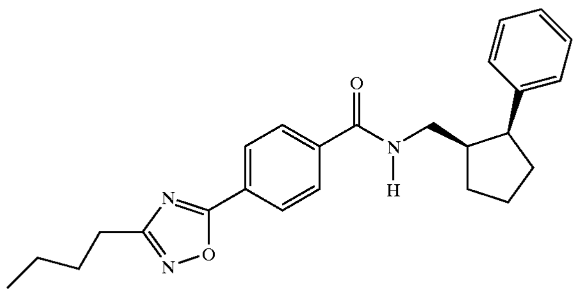 | $C_{25}H_{29}N_3O_2$: mp 112.0–115.0° C.<br>Analysis calculated: C, 74.41; H, 7.24; N, 10.41.<br>Found C, 74.38; H, 7.29; N, 10.36. |
| 29y | 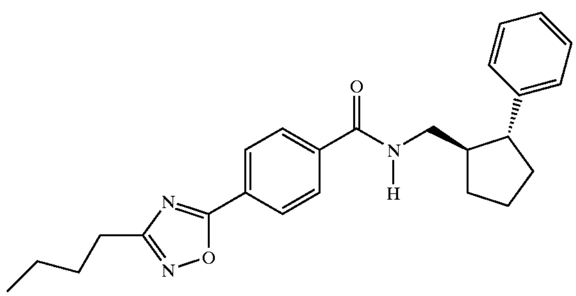 | mp 92.0–93.0° C.<br>ESI (m/z) 404 |
Example 30
N-(3,3-Dimethylbutyl)-6-(hexyloxy)-3-pyridine Carboxamide
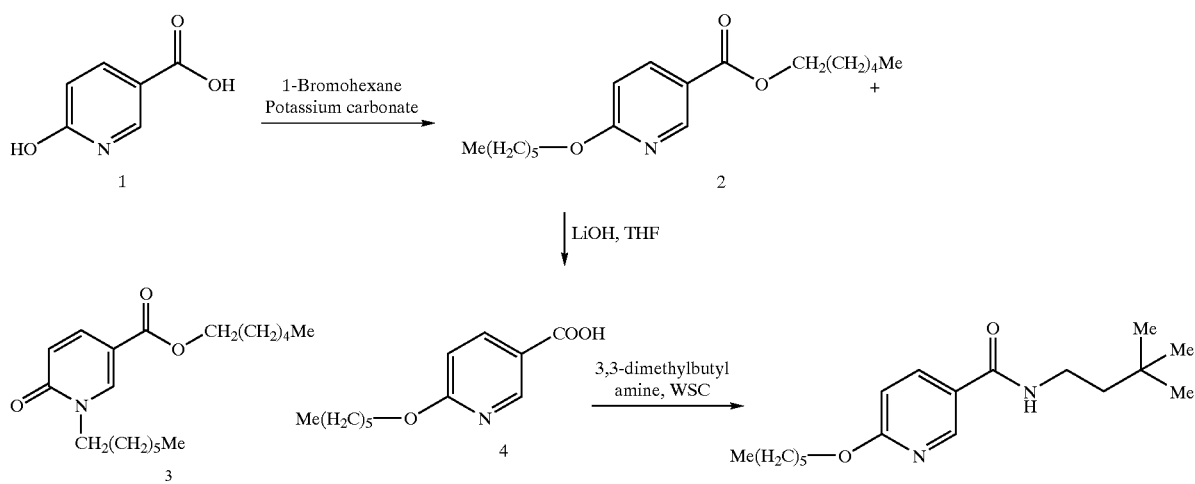

A. 6-(Hexyloxy)-3-pyridinecarboxylic Acid Hexyl Ester and 1-Heptyl-1,6-dihydro-6-oxo-3-pyridinecarboxylic Acid Hexyl Eester A stirred mixture of 6-hydroxynicotinic acid (10.0 g, 0.072 mole) in dimethylformamide (100 mL) under argon at room temperature was treated with 1-bromohexane (30 mL, 35.6 g, 0.216 mole) and powdered potassium carbonate (49.7 g, 0.36 mole) and heated at 110° C. for 3 days. The reaction mixture, diluted with ethyl acetate, was washed with water and brine, dried (anhydrous magnesium sulfate) and concentrated. Flash chromatography on silica gel and elution with ethyl acetate/hexanes (1:8) gave 2 (4.77 g, 21.5%) and 3 (14.86 g, 67.5%).

B. 6-(Hexyloxy)-3-pyridinecarboxylic Acid

A solution of compound 2 (1.0 g, 3.25 mmole) in tetrahydrofuran (15 mL) was treated with 1 N lithium hydroxide (6.5 mL) and heated at reflux for 24 hours. Solvent was removed in vacuo and the residue was partitioned between ethyl acetate and water. The aqueous fraction was acidified with 6 N hydrochloric acid and extracted with ethyl acetate (2x). The combined organic extracts were washed with water and brine, dried (anhydrous magnesium sulfate) and concentrated to give 4 (480 mg, 66%), mp 90–93° C.

C. N-(3,3-Dimethylbutyl)-6-(hexyloxy)-3-pyridine Carboxamide

A solution of compound 4 (223 mg, 1.0 mmol) in dimethylformamide (2.5 mL) under argon at room temperature was treated with 3,3-dimethylbutyl amine (111 mg, 1.1 mmol), ethyl-3-(3-dimethylamino)-propylcarbodiimide hydrochloride (327 mg, 1.1 mmol) and hydroxybenzotriazole monohydrate (148 mg, 1.1 mmol) and stirred overnight. The reaction mixture was diluted with ethyl acetate and washed with 10% citric acid, water, dilute sodium bicarbonate, water and brine, dried (anhydrous mnagnesium sulfate) and concentrated to give an oil. Flash chromatography on silica gel and elution with ethyl acetate/hexanes (1:4) gave an oil (274 mg) that slowly solidified, mp 75–76.5° C. Analysis calculated for $C_{18}H_{30}N_2O_2$: C, 70.55; N, 9.87; N, 9.14. Found: C, 70.46; H, 10.06; N, 9.02.

Example 31
N-(3,3-Dimethylbutyl)-1-hexyl-1,6-dihydro-6-oxo-3-pyridinecarboxamide

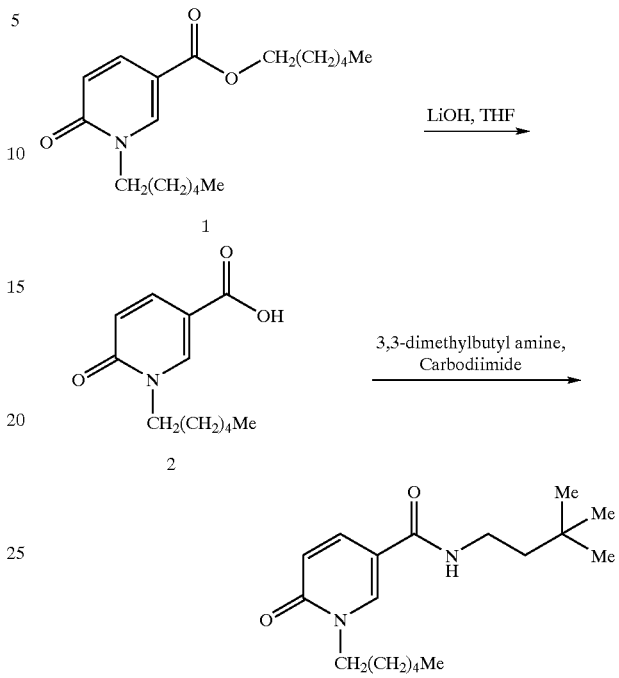

A. 1-Hexyl-1,6-dihydro-6-oxo-3-pyridinecarboxylic Acid

This compound was prepared from compound 1-Hexyl-1,6-dihydro-6-oxo-3-pyridinecarboxylic acid hexyl ester by the same procedure (lithium hydroxide, THF) as described for the preparation of compound 4 from 2 (Example 30, part B).

B. N-(3,3-Dimethylbutyl)-1-hexyl-1,6-dihydro-6-oxo-3-pyridinecarboxamide

The title compound was prepared from compound 2 by the same procedure as described for the preparation of the title compound of Example 30, part C: mp 80–83° C. Analysis calculated for $C_{18}H_{30}N_2O_2$: C, 70.55; N, 9.87; N, 9.14. Found: C, 70.41; H, 9.91; N, 9.37.

Using methodology analogous to that described for the title compounds of Examples 30 and 31, the compounds of Examples 32 and 33 were prepared.

| Example # | Structure | Characterization |
|---|---|---|
| 32 | 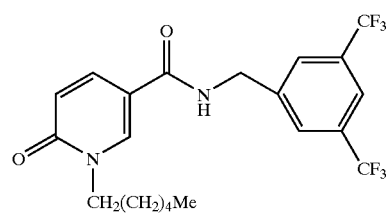 | $C_{21}H_{22}F_6N_2O_2$: m/e = 448.<br>Analysis calculated: C, 56.25; H, 4.95; N, 6.25; F, 25.42.<br>Found: C, 56.21; H, 4.80; N, 6.16; F, 25.72. |

-continued

| Example # | Structure | Characterization |
|---|---|---|
| 33 | 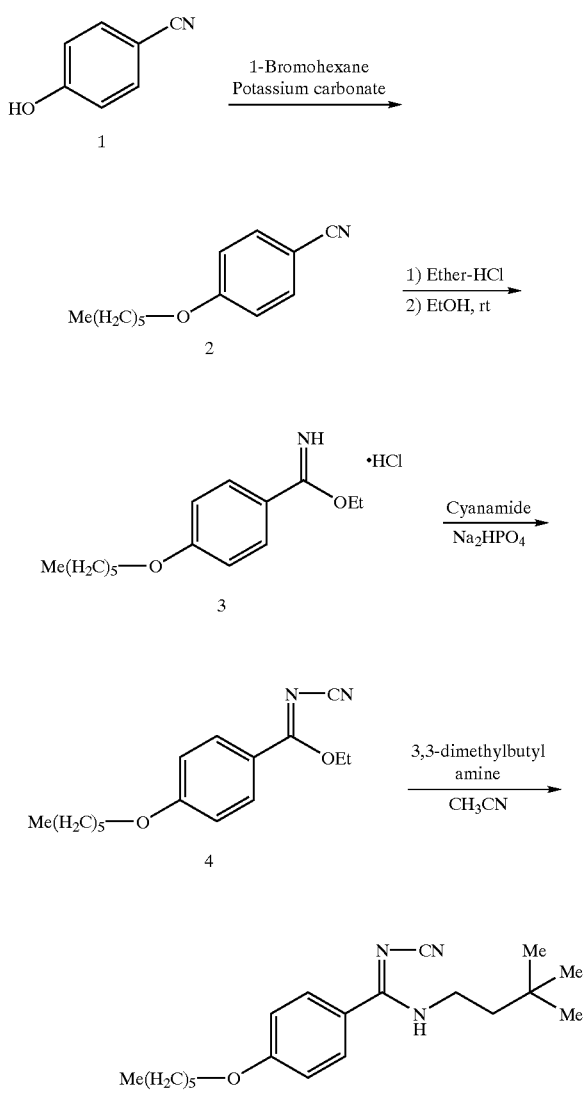 | $C_{21}H_{22}F_6N_2O_2 \cdot 0.25$ hexane: mp 92–95° C.<br>Analysis calculated: C, 57.46; H, 5.47; N, 5.96; F, 24.24.<br>Found: C, 57.46; H, 5.21; N, 6.01; F, 24.04. |

Example 34
N-Cyano-N'-(3,3-dimethylbutyl)-4-(hexyloxy)benzene-carboximidamide

A. 4-(Hexyloxy)benzonitrile

A solution of 4-cyanophenol (20 g, 168 mmol) in dimethylformamaide was treated with potassium carbonate (2 eq., 338 mmol, 47 g) and 1-bromohexane (1.1 eq., 185 mmol, 35 mL) and stirred at room temperature for 18 hours. The solid was filtered off and the solution was partitioned between ethyl acetate and 1 N HCl. The organic phase was washed with brine, dried over $MgSO_4$, filtered and the solvent was removed to give compound 2 (45 g, >100%).

B. 4-(Hexyloxy)benzenecarboximidic Acid Ethyl Ester

A solution of compound 2 (5.00 g, 24.6 mmol) in diethyl ether was cooled to 0° C. and treated slowly with excess freshly prepared cold saturated ethereal-hydrochloric acid (g). The reaction mixture was treated with ethanol (30 mL) and allowed to warm to room temperature and stirred for 18 hours. The solvent was removed to give compound 3 as an oil (4.09 g, 85%).

C. N-Cyano-4-(hexyloxy)benzenecarboximidic Acid Ethyl Ester

A solution of compound 3 (1.0 g, 4.0 mmol) in water/THF (10 mL, 1:1) was treated with sodium dihydrogenphosphate (1.13 g, 8 mmol, in 10 mL water) followed by an aqueous solution of cyanamide (202 mg, 4.8 mmol in 2 mL water). The biphasic solution was stirred vigorously for 24 hours. The solution was partitioned between ethyl acetate and saturated sodium bicarbonate solution. The organic phase was washed with brine, dried over magnesium sulfate and the solvent was removed to give compound 4 as a white solid (1.01 g, 87%).

D. N-Cyano-N'-(3,3-dimethylbutyl)-6-(hexyloxy)-benzenecarboximidamide

A solution of compound 4 (200 mg, 0.73 mmol) in acetonitrile was treated with 3,3-dimethylbutyl amine (118 µl, 0.875 mmol) and heated to 50° C. in a sand bath for 18 hours. The solution was partitioned between ethyl acetate and 10% citric acid solution. The organic phase was washed with brine, dried over magnesium sulfate and evaporated. The residue was purified by flash column chromatography on silica gel using 20% ethyl acetate in hexane to give the title product (90 mg, 38%), mp 89–90° C. Analysis calculated for $C_{20}H_{31}N_3O$: C, 72.91, H, 9.48, N, 12.75. Found: C, 72.77, H, 9.47, N, 12.66.

Using methodology analogous to that described for the title compound of Example 34, the compounds of Examples 35 and 36 were prepared.

| Example # | Structure | Characterization |
|---|---|---|
| 35 | 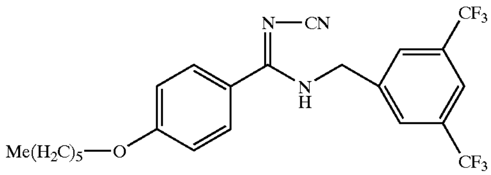 | $C_{23}H_{23}F_6N_3O$: mp 118–129° C.<br>Analysis calculated: C, 58.60; H, 4.92; N, 8.91; F, 24.18.<br>Found: C, 58.99; H, 4.67; N, 8.76; F, 23.93. |
| 36 | 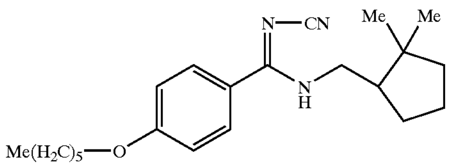 | $C_{22}H_{33}N_3O \cdot 0.03\text{EtOAc}$.<br>Analysis calculated: C, 73.18; H, 9.67; N, 12.12.<br>Found: C, 73.69; H, 9.67; N, 11.62. |
| 36a | 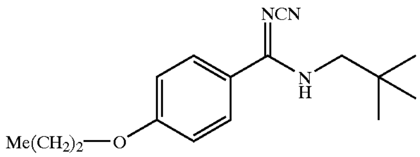 | $C_{19}H_{29}N_3O$: mp 69–71° C.<br>Analysis calculated: C, 72.34; H, 9.27; N, 13.31.<br>Found: C, 72.11; H, 9.36; N, 13.21. |
| 36b | 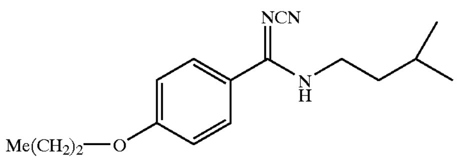 | $C_{19}H_{29}N_3O$: mp 106–107° C.<br>Analysis calculated: C, 72.34; H, 9.27; N, 13.31.<br>Found: C, 72.08; H, 9.35; N, 13.19. |
| 36c | 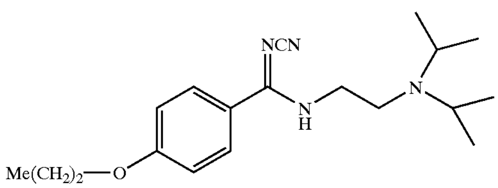 | $C_{22}H_{36}N_4O \cdot 0.17 H_2O$: mp 106–107° C.<br>Analysis calculated: C, 70.93; H, 9.75; N, 14.92.<br>Found: C, 70.35; H, 9.75; N, 14.44. |

Example 37

N-(3,3-Dimethylbutyl)-N'-[4-(hexyloxy)phenyl]urea

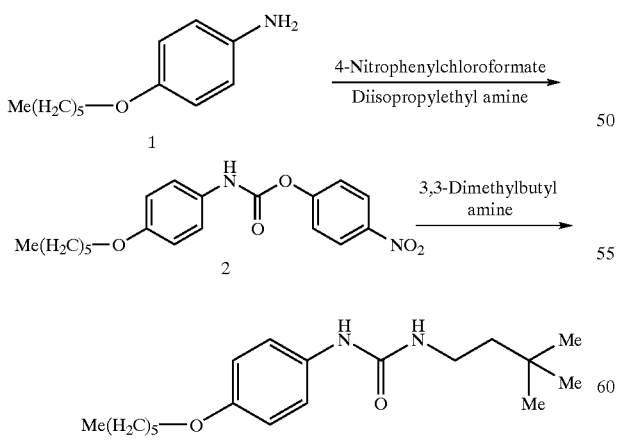

A. [4-(Hexyloxy)phenyl]carbamic Acid 4-nitrophenyl Ester

A solution of 4-hexyloxyaniline (1.00 g, 5.17 mmol) in dichloromethane (10 mL) was treated with diisopropylethylamine (1.80 mL, 10.3 mmol) followed by p-nitrophenylchloroformate (1.05 g, 5.71 mmol). The reaction mixture was stirred for 3 hours at room temperature and diluted with ethyl acetate. The ethyl acetate solution was washed with hydrochloric acid and brine. After drying over magnesium sulfate the solvent was removed to yield a brown oil. Purification by flash chromatography on silica gel eluted with 15% acetone in hexanes provided compound 2 as a tan solid (241 mg, 13%).

B. N-(3,3-Dimethylbutyl)-N'-[4-(hexyloxy)phenyl]urea

To a solution of compound 2 (90 mg, 0.25 mmol) in tetrahydrofuran (1 mL) was added 3,3-dimethylbutylamine (41 µL, 0.30 mmol). The reaction was stirred for 18 hours and then purified by flash chromatography on silica gel eluted with 5% 2-propanol in hexanes to provide the title compound as a white solid (75 mg, 94%): mp 103–104° C. Analysis calculated for $C_{19}H_{32}N_2O_2 \cdot 0.14 H_2O$: C, 70.65; H, 10.07; N, 8.67. Found: C, 70.67; H, 10.12; N, 8.52.

Using methodology analogous to that described for the title compound of Example 37, the compound of Example 38 was prepared.

| Example # | Structure | Characterization |
|---|---|---|
| 38 | ![structure] | $C_{18}H_{30}N_2O_2 \cdot 0.17H_2O$: mp 108–109° C. Analysis calculated: C, 69.85; H, 9.88; N, 9.05. Found: C, 69.84; H, 9.85; N, 8.89. |

Example 39 (BMS-207307)
N-Cyano-N'-(3,3-dimethylbutyl)-N "-[4-(hexyloxy)phenyl]-guanidine

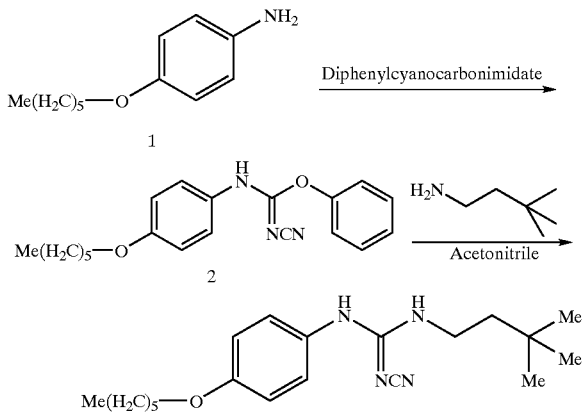

A. N-Cyano-N'-[4-(hexyloxy)phenyl]carbamimidic Acid Phenyl Ester

A solution of 4-hexyloxyaniline (1.0 g, 5.17 mmol) in tetrahydrofuran (2 mL) was added to a –25° C. solution of potassium hydride (652 mg of 35% in oil, 5.6 mmol, washed 3 times with hexane) in dry tetrahydrofuran (2 mL) and was stirred for 30 minutes. The reaction mixture was then treated with diphenylcyanocarbonimidate (1.48 g, 6.2 mmol) and stirred overnight while warming to room temperature. The reaction mixture was quenched with water and then partitioned between ethyl acetate and 10% citric acid solution. The organic phase was washed with brine, dried over $MgSO_4$, filtered and the solvent was removed. The residue was purified first by flash column chromatography on silica gel using 25% ethyl acetate/hexane as the mobile phase and the product was recrystallized from isopropyl ether/hexane/$CH_2Cl_2$ to give compound 2 as white needles (424 mg, 24%).

B. N-Cyano-N'-(3,3-dimethylbutyl)-N"-[4-(hexyloxy)phenyl]-guanidine

A solution of compound 2 (400 mg, 1.19 mmol) in acetonitrile/isopropanol (2 mL of 1:1 mixture) was treated with 3,3-dimethylbutylamine (240 μl, 1.79 mmol) and heated to 60° C. in a sand bath for 24 hours. The solution was cooled to room temperature, diluted with ethyl ether and washed with 1 N HCl. The organic phase was washed with brine, dried over $MgSO_4$ and the solvent was removed. The residue was crystallized from EtOAc to give the title compound as a colorless solid (168 mg, 41%), mp 183–184° C. Analysis calculated for $C_{20}H_{32}N_4O$: C, 69.93; H, 9.36; N, 16.26. Found: C, 69.54; H, 9.47; N, 16.05.

Using methodology analogous to that described for the title compound of Example 39, the compounds of Examples 40 to 42 were prepared.

| Example # | Structure | Characterization |
|---|---|---|
| 40 | ![structure] | $C_{19}H_{30}N_4O$: mp 119–120° C. Analysis calculated: C, 69.06; H, 9.15; N, 16.95. Found: C, 69.02; H, 9.16; N, 16.88. |
| 41 | ![structure] | $C_{22}H_{37}N_5O$: mp 88–89° C. Analysis calculated: C, 68.18; H, 9.61; N, 18.07. Found: C, 68.29; H, 9.48; N, 17.82. |
| 42 | ![structure] | $C_{19}H_{30}N_4O$: m/e = 330. |

| Example # | Structure | Characterization |
|---|---|---|
| 42a | 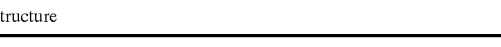 | $C_{23}H_{24}N_4F_6O.0$: mp 122–123° C.<br>Analysis calculated: C, 56.79; H, 4.97; N, 11.52; F, 23.43.<br>Found: C, 56.79; H, 4.84; N, 11.52; F, 23.10. |

Example 43

N-(3,3-Dimethylbutyl)-4-(hexyloxy)benzenecarboximidamide, Monohydrochloride

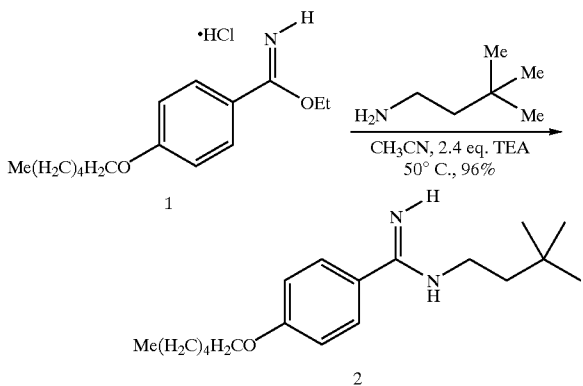

A solution of the title B compound of Example 34 (500 mg, 1.75 mmol) in acetonitrile was treated triethylamine (2.4 eq., 596 μl), followed by 3,3-dimethylbutylamine (1.5 eq., 2.6 mmol, 353 μl) and heated at 50° C. for 18 hours. The reaction mixture was partitioned between ethyl acetate and saturated sodium bicarbonate. The organic phase was washed with brine, dried over anhydrous magnesium sulfate, filtered and concentrated. The residue was purified by recrystallization from isopropyl ether/hexane to give the title compound (510 mg, 96%), mp 235–237° C. Analysis calculated for $C_{19}H_{32}N_2O.1.22$ HCl.1.12 $H_2O$: C, 61.82; H, 9.68; N, 7.59; Cl, 11.72. Found: C, 61.83; H, 9.60; N, 7.54; Cl, 12.14.

Using the above methodology, the following compounds were prepared.

| Example # | Structure | Characterization |
|---|---|---|
| 44 | 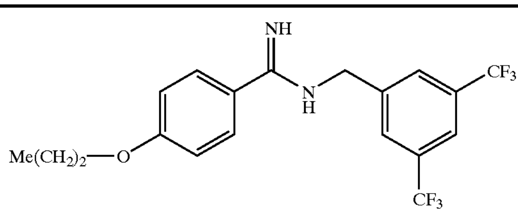 | $C_{22}H_{24}F_6N_2O.1.0HCl$: mp 168–169.5° C.<br>Analysis calculated: C, 54.72; H, 5.22; N, 5.80; F, 23.61; Cl, 7.34.<br>Found: C, 55.27; H, 5.34; N, 5.65; F, 23.37; Cl, 7.41. |

Example 45

N-[4-(Hexyloxy)phenyl]-4,4-dimethyl-3-oxopentanamide

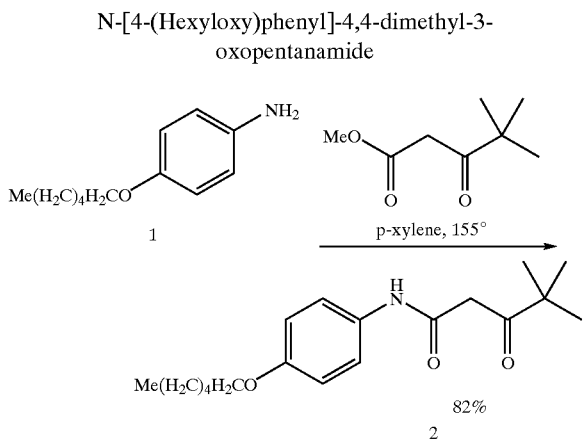

A. N-[4-(Hexyloxy)phenyl]-4,4-dimethyl-3-oxopentanamide

4-Hexyloxyaniline (1, 1.00 g, 5.17 mmol) and methyl-4,4-dimethyl-3-oxopentanoate (1.65 mL, 10.3 mmol) were suspended in 5 mL p-xylene and heated to reflux for 17 hours. The reaction was cooled to room temperature and purified by flash chromatography on silica gel eluting with 10% acetone, hexane to yield a brown solid. Recrystallization from hexane provided 1.35 g (82%) of a white solid. mp 70–72° C.; Analysis calculated for $C_{19}H_{29}NO_3$: C, 71.44; H, 9.15; N, 4.38. Found: C, 71.72; H, 9.42; N, 4.30.

Example 46

4-(2-Butyl-2H-tetrazol-5-yl)-N-[(2,2-dimethylcyclopentyl)-methyl]benzamide and 4-(1-Butyl-1H-tetrazol-5-yl)-N-[(2,2-dimethylcyclopentyl)methyl]benzamide

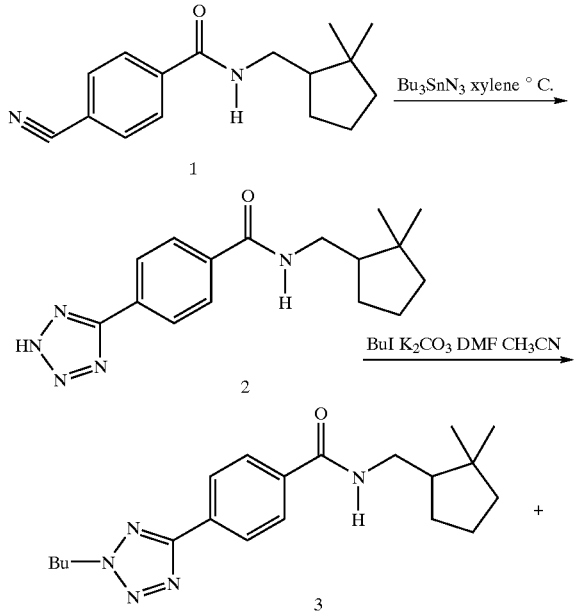

A. 4-(1H-Tetrazol-5-yl)-N-[(2,2-dimethylcyclopentyl)-methyl]benzamide

Azidotributyl stannane (5.2 g, 4.4 mL, 15.8 mmol) was added to a solution of the title compound of Example 29b (0.60 g, 2.3 mmol) in xylene (5.1 mL) and the mixture was stirred at 120° C. for 15 hours. After cooling, the reaction was diluted with $CH_2Cl_2$ (40 mL) and 1N HCl (10 mL) and stirred vigorously for 30 minutes. The solid was filtered and rinsed with alternating portions of $CH_2Cl_2$ (3×20 mL) and 1 N HCl (3×20 mL) and dried under high vacuum overnight to afford the title compound as a white solid.

B. 4-(2-Butyl-2H-tetrazol-5-yl)-N-[(2,2-dimethylcyclopentyl)-methyl]benzamide and 4-(1-Butyl-1H-tetrazol-5-yl)-N-[(2,2-dimethylcyclopentyl)methyl]benzamide A mixture of the title A compound (0.60 g, 2.0 mmol), iodobutane (0.38 g, 0.24 mL, 2.1 mmol), $K_2CO_3$ (0.40 g, 3.0 mmol), and DMF (5.0 mL) in acetonitrile (20 mL) was stirred at 55° C. After 19 hours, the reaction was transferred to a separatory funnel with EtOAc/1 N HCl. The mixture was extracted with EtOAc (2×40 mL), washed with brine, dried ($MgSO_4$) and concentrated in vacuo. Flash chromatography (silica, 50 mm, 25% EtOAc/hexane) afforded the 4-(2-butyl-2H-tetrazol-5-yl)-N-[(2,2-dimethylcyclopentyl)methyl]benzamide (0.57 g, 81%): mp 121–123° C. Analysis calculated for $C_{20}H_{29}N_5O$—C, 67.58; H, 8.22; N, 19.7; Found: C, 67.48; H, 8.46; N, 19.68.

Further elution afforded 4-(1-butyl-1H-tetrazol-5-yl)-N-[(2,2-dimethylcyclopentyl)methy]benzamide (46 mg, 6%): mp 106–109° C. Analysis calculated for $C_{20}H_{29}N_5O \cdot H_2O$: C, 65.27; H, 8.32; N, 19.03. Found: C, 65.32; H, 8.31; N, 18.63.

Example 47

(R)-N-[(2,2-Dimethylcyclopentyl)methyl]-4-(5-butyl-1,2,4-4H-triazol-3-yl)benzamide

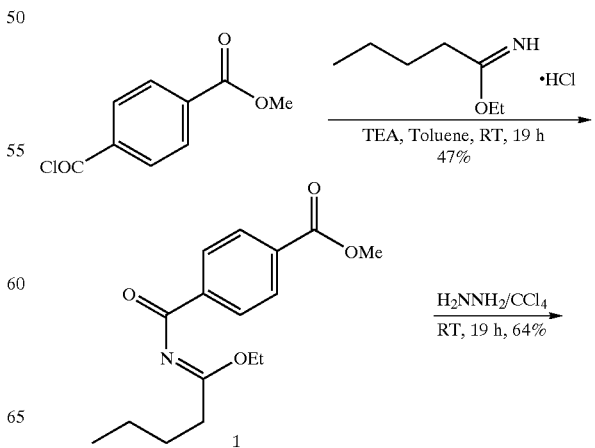

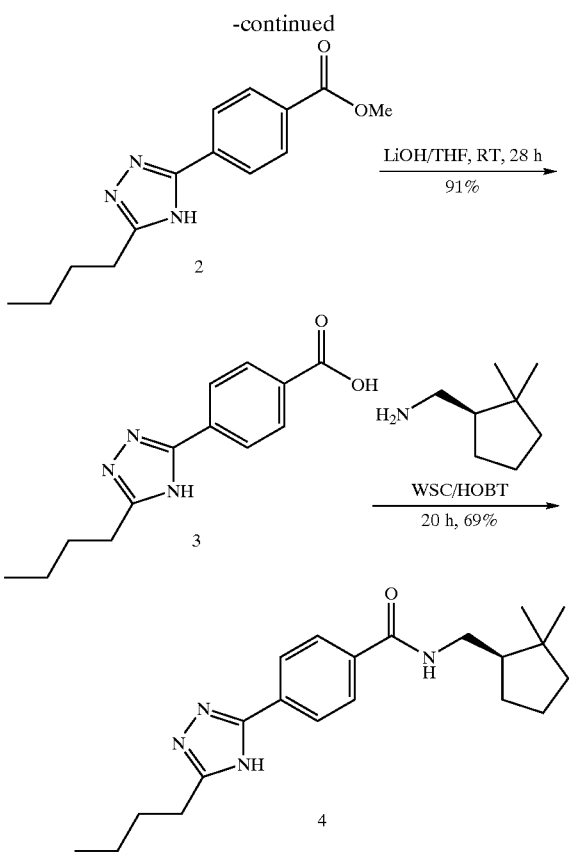

A. 4-[[(1-Ethoxypentylidene)amino]carbonyl]benzoic Acid Methyl Ester

To a solution of ethyl pentanimidate hydrochloride (9 g, 54 mmol) and triethyl amine (17 mL, 120 mmol) in toluene (110 mL) at 0° C. was added, over 20 minutes, a solution of terephthalic acid, monomethyl ester chloride (10.8 g, 54 mmol) in toluene (21 mL). After stirring at ambient temperature for 19 hours, the reaction was filtered and the solids were rinsed with toluene (200 mL). The combined filtrates were concentrated in vacuo. Flash chromatography (silica gel, $CH_2Cl_2$) of a portion of this material afforded the title compound (1.9 g, 47%).

B. 4-(5-Butyl-1H-1,2,4-triazol-3-yl)benzoic Acid Methyl Ester

Hydrazine (0.23 g, 0.22 mL, 7.0 mmol) was added to a solution of the title A compound (1.9 g, 6.4 mmol) in $CCl_4$ (32 mL). After standing at ambient temperature for 19 hours, the reaction was transferred to a separatory funnel containing $CH_2Cl_2/H_2O$. The mixture was extracted with $CH_2Cl_2$ (2×50 mL) and 10% $MeOH/CH_2Cl_2$ (3×30 mL). The combined organic layers were dried ($MgSO_4$) and concentrated in vacuo. Flash chromatography (silica gel, 50% EtOAc/hexane) gave the title compound (1.06 g, 64%).

C. 4-(5-Butyl-1,2,4-1H-triazol-3-yl)benzoic Acid

Lithium hydroxide (1 N, 8.2 mL, 8.2 mmol) was added to a solution of the title B compound (1.06 g, 4.1 mmol) in THF (45 mL). After stirring at ambient temperature for 28 hours, the reaction was evaporated in vacuo. The aqueous residue was acidified with 1 N HCl to pH 3 to 4. The resulting solid was filtered, washed with $H_2O$, and dried under high vacuum to afford the title compound (0.90 g, 91%).

D. (R)-N-[(2,2-Dimethylcyclopenyl)methyl]-4-(5-butyl-1,2,4-1H-triazol-3-yl)benzamide 1-Hydroxybenzotriazole hydrate (70 mg, 0.51 mmol) and 1-(3-dimethylaminopropyl)-3-ethylcarbodiimide hydrochloride (WSC, 156 mg, 0.51 mmol) were added to a solution of the title C compound (123 mg, 0.50 mmol) in $CH_2Cl_2$ (2.2 mL) and DMF (0.57 mL) stirring at ambient temperature. After stirring for 30 minutes, (R)-((2,2-dimethylcyclopentyl)methyl)amine, hydrochloride (82 mg, 0.50 mmol) in $CH_2Cl_2$ (0.64 mL) was added followed by triethylamine (0.070 mL, 0.50 mmol). After stirring for 20 hours, the reaction was transferred to a separatory funnel with ether/$H_2O$ and the aqueous layer acidified with 1 N HCl. The mixture was extracted with ether (2×80 mL), washed with saturated $NaHCO_3$, brine, dried ($MgSO_4$) and concentrated in vacuo. Flash chromatography (silica gel, 50% EtOAc/$CH_2Cl_2$) afforded the title compound (0.12 g, 69%): mp 182.0–184.5° C. Analysis calculated for $C_{21}H_{30}N_4O\cdot 0.27\ H_2O$: C, 70.20; H, 8.57; N, 15.59. Found: C, 70.20; H, 8.80; N, 15.43.

Using the procedure described in Example 47, the following compounds were prepared.

| Example # | Structure | Characterization |
|---|---|---|
| 48 | ![structure] | $C_{21}H_{30}N_4O\cdot 0.18H_2O$: ESI (m/z) 355. Analysis calculated: C, 70.50; H, 8.55; N, 15.66. Found: C, 70.50; H, 8.72; N, 15.44. |

Example 49

4-(3-Butyl-5-isoxazolyl)-N-[(2,2-dimethylcyclopentyl)-methyl]benzamide

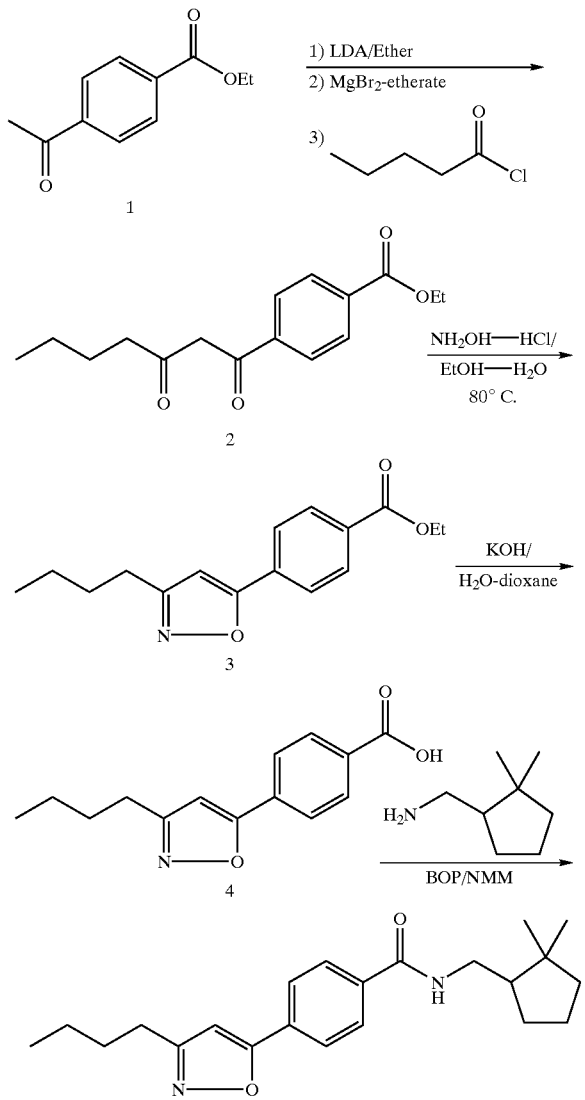

A. 4-(3-Butyl-5-isoxazolyl)benzoic Acid Ethyl Ester

A solution of ethyl 4-acetylbenzoate (2.93 g, 15.3 mmol) in 25 mL ether was added to a solution of lithium diisopropylamide (0.805 M in THF-hexane, 20.85 mL, 16.79 mmol) in 200 mL of ether at −70° C. The mixture was stirred at −78° C. for 30 minutes, magnesium bromide etherate (3.94 g, 15.26 mmol) was added and the reaction mixture was stirred for 30 minutes followed by the addition of valeryl chloride (1.47 g, 12.2 mmol) in 3 mL ether. Stirring was continued at −78° C. for an additional 30 minutes. The mixture was allowed to come to room temperature, quenched by adding saturated ammonium chloride and acidified (pH=3.0) by adding 20% sulfuric acid. The mixture was extracted with ethyl acetate, the organic layer was dried over magnesium sulfate, concentrated, and the residue subjected to flash chromatography (silica gel/hexane-ethyl acetate 95:5) to afford the title compound (1.35 g).

B. 4-(3-Butyl-5-isoxazolyl)benzoic Acid Ethyl Ester

A solution of the title A compound (150 mg, 0.54 mmol) in 1.5 mL ethanol was treated with a solution of hydroxylamine hydrochloride (41.4 mg, 0.6 mmol) in 0.15 mL of water. The mixture was heated at 80° C. in a sealed tube for 2 hours, concentrated, and the residue partitioned between water and methylene chloride. The methylene chloride layer was dried over magnesium sulfate and concentrated to afford the desired product (145 mg).

C. 4-(3-Butyl-5-isoxazolyl)benzoic Acid

A solution of the the title B compound (145 mg) in 6 mL dioxane was treated with 10% aqueous potassium hydroxide (6 mL) and the mixture was stirred at room temperature for 14 hours. The mixture was diluted with water, washed with ether, the aqueous layer was acidified with 10% sodium hydrogen sulfate and extracted with ethyl acetate. The ethyl acetate layer was dried over magnesium sulfate, concentrated to give the desired compound (88 mg) as a white solid.

D. 4-(3-Butyl-5-isoxazolyl)-N-[(2,2-dimethylcyclopentyl)-methyl]benzamide

The title C compound was sequentially treated with benzotriazol-1-yloxytris(dimethylamino)phosphonium hexafluorophosphate (BOP) (174.4 mg, 0.395 mmol), 2,2-dimethylcyclopentylmethyl amine (59 mg, 0.359 mmol; the title B compound of Example 1) and N-methylmorpholine in 3 mL DMF. The mixture was stirred at room temperature for 14 hours, diluted with water, stirred for 5 minutes and the resulting precipitate was isolated by filtration. The crude product was recrystallized from hexane to give the title compound (90 mg) as a white solid.

Example 50

4-(3-Butyl-1H-pyrazol-5-yl)-N-[(2,2-dimethylcyclopentyl)-methyl]benzamide

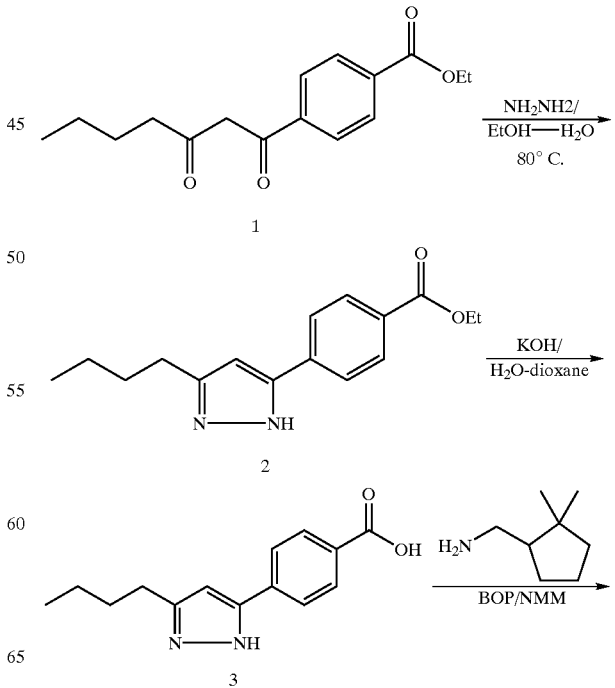

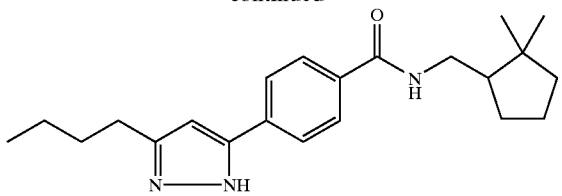

A. 4-(3-Butyl-1H-pyrazol-5-yl)benzoic Acid Ethyl Ester

This title compound was prepared from compound 1 (title A compound of Example 49) and hydrazine by a similar procedure as described for the title B compound of Example 49.

B. 4-(3-Butyl-1H-pyrazol-5-yl)-N-[(2,2-dimethylcyclopentyl)-methyl]benzamide The title A compound was converted to the desired product by a sequence of reactions as described for the preparation of the title compound of Example 49 from the title B compound of Example 49. The product was obtained as a white solid, MS: m/e=353.

Example 51

4-(5-Butyl-1,3,4-oxadiazol-2-yl)-N-[(2,2-dimethylcyclopentyl)-methyl]benzamide, Enantiomer A and Enantiomer B

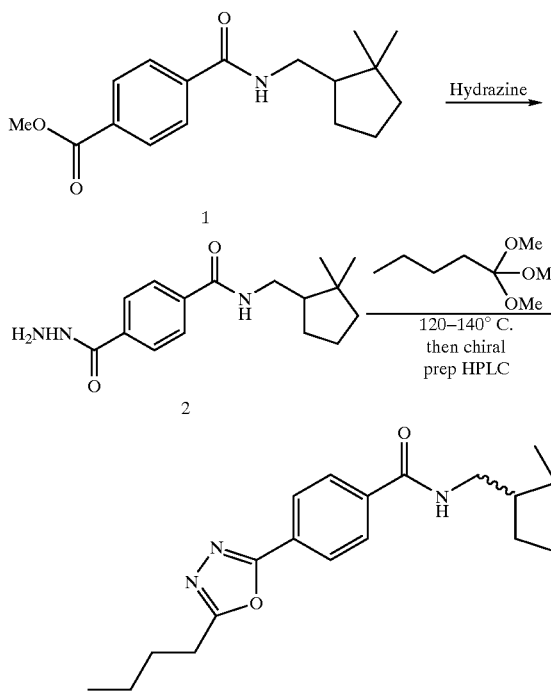

A. 4-[[[(2,2-Dimethylcyclopentyl)methyl]amino]-carbonyl]benzoic Acid Methyl Ester The title compound was prepared from monomethyl-terephthalate and 2,2-dimethylcyclopentylmethyl amine (title B compound of Example 1) in a manner as described for the title A compound of Example 24.

B. 4-[[[(2,2-Dimethylcyclopentyl)methyl]amino]-carbonyl]benzoic Acid Hydrazide The title A compound (275 mg) was treated with hydrazine monohydrate and heated at 120° C. for 2 hours. The reaction mixture was diluted with water, saturated with potassium carbonate and extracted with ethyl acetate. The organic layer was dried over magnesium sulfate and concentrated to give the title compound (270 mg) as a white solid which was used in the next reaction without isolation.

C. 4-(5-Butyl-1,3,4-oxadiazol-2-yl)-N-[(2,2-dimethylcyclopentyl)methyl]benzamide, Enantiomer A and Enantiomer B The title B compound was heated in trimethyl orthovalerate (3 mL), at 120° C. for 2 hours. The excess trimethyl orthovaerate was removed by purging with a stream of nitrogen at 140° C. The residue was heated at 140° C. for 1.5 hours, diluted with methylene chloride, washed with 10% potassium carbonate and the organic layer was dried (magnesium sulfate) and concentrated. The crude product was subjected sequentially to flash chromatography (silica gel/hexane-EtOAc 1:1) and chiral preparative HPLC (Chirapak AD column/hexane-isopropanol-triethylamine 80:20:0.2) to give the two enantiomers: (+)-enantiomer A (104 mg, $[\alpha]_D$=+22° C.=0.36, methylene chloride, m/e 355) and the (−)-enantiomer B (100 mg, $[\alpha]_D$=−19.5° C.=0.36, methylene chloride, m/e 355) as white solids.

Example 52

3-[4-(3-Butyl-1,2,4-oxadiazol-5-yl)phenyl]-N-[(2,2-dimethyl-cyclopentyl)methyl]-2-propenamide

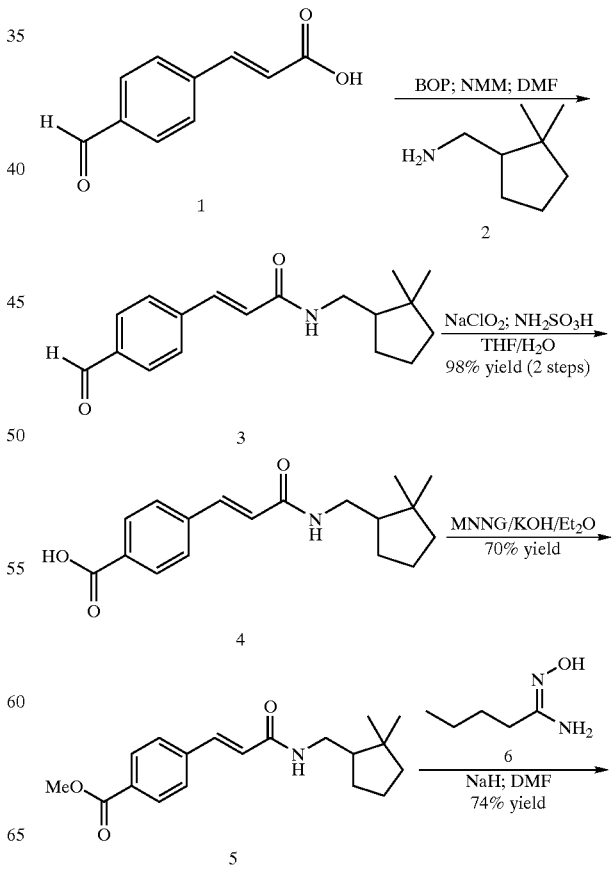

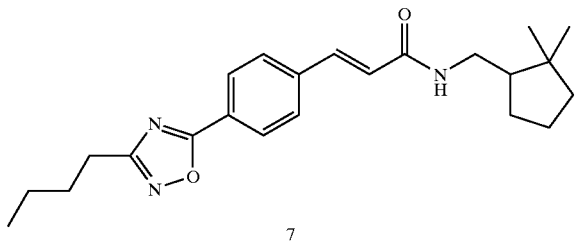

7

A. N-[(2,2-Dimethylcyclopentyl)methyl]-3-(4-formylphenyl)-2-propenamide

To a cold (0° C.) solution of 4-formylcinnamic acid (345 mg, 1.96 mmol) and 2,2-dimethylcyclopentylmethylamine, hydrochloride (321 mg, 1.96 mmol; title B compound of Example 1) in DMF (5 mL) was added benzotriazol-1-yloxytris(dimethylamino)phosphonium hexafluorophosphate (BOP) (954 mg, 2.16 mmol) and N-methylmorpholine (0.47 mL, 4.31 mmol). The cooling bath was removed and the reaction mixture was stirred at room temperature for 18 hours. The reaction mixture was diluted with dichloromethane and washed with 1 N HCl and saturated NaHCO$_3$ solution. The organic layer was dried (MgSO$_4$) and concentrated in vacuo to yield a light amber gum. MS: (ESI), (M+H)$^+$ 286.

B. 4-[3-[[(2,2-Dimethylcyclopentyl)methyl]amino]-3-oxo-1-propenyl]benzoic Acid

To stirred solution of the title A compound in THF/H$_2$O (15 mL of a 1:1 mixture) at 0° C. was added sodium chlorite (329 mg, 3.64 mmol) and sulfamic acid (353 mg, 3.64 mmol). The cooling bath was removed and the reaction was allowed to warm up to room temperature. Once the reaction was complete, the mixture was diluted with dichloromethane and washed with saturated potassium bisulfate solution. The organic layers were separated and the aqueous layer was backwashed with fresh dichloromethane (twice). The combined organic extracts were washed with freshly prepared 2% sodium bisulfite solution, dried (MgSO$_4$) and concentrated in vacuo to afford a light yellow solid (583 mg, 98%), mp 138–140° C.

C. 4-[3-[[(2,2-Dimethylcyclopentyl)methyl]amino]-3-oxo-1-propenyl]benzoic Acid Methyl Ester The freshly prepared excess diazomethane was slowly added to a cold (0° C.) solution of the title B compound (583 mg, 1.93 mmol) in diethyl ether (50 mL) until a yellow color persisted. The reaction was quenched with a few drops of glacial acetic acid until the yellow color disappeared. The reaction was then concentrated in vacuo to afford a yellow gum which was purified by flash chromatography on silica gel (10% EtAc in hexane) gave the desired product as a creamy light yellow solid. MS: (ESI) (M+H)$^+$316.

D. 3-[4-(3-Butyl-1,2,4-oxadiazol-5-yl)phenyl]-N-[(2,2-dimethylcyclopentyl)methyl]-2-propenamide To a solution of the title C compound (100 mg, 0.32 mmol) and n-butylhydroxyamidine (46 mg, 0.40 mmol) in DMF (2 mL) was added NaH (17 mg, 0.70 mmol). After stirring for 18 hours at room temperature, the reaction mixture was diluted with dichloromethane and washed with water. The combined organic extracts were dried (MgSO$_4$), and concentrated in vacuo to yield a yellow solid (90 mg, 74%), mp 144–145° C. MS (ESI): (M+H)$^+$382.

Using the procedures described above the following compounds were prepared.

| Example # | Structure | Characterization |
|---|---|---|
| 53 | 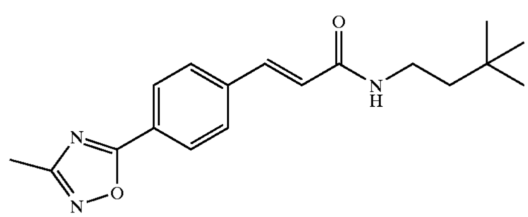 | $C_{18}H_{23}N_3O_2$: mp 185–186° C. |
| 54 | 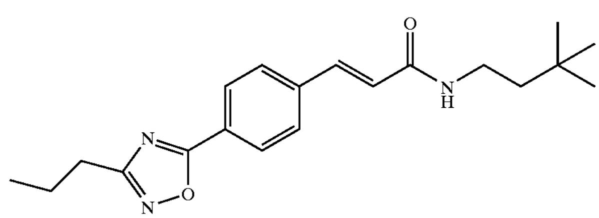 | $C_{20}H_{27}N_3O_2$: mp 162–164° C. |
| 55 | 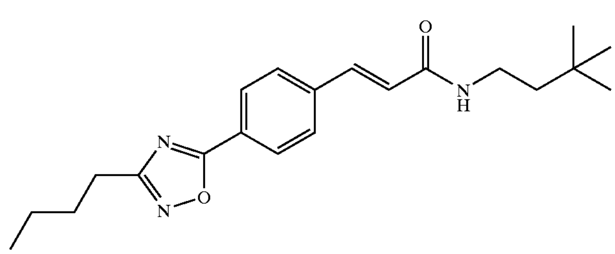 | $C_{21}H_{29}N_3O_2$: mp 164–166° C. |

-continued

| Example # | Structure | Characterization |
|---|---|---|
| 56 | 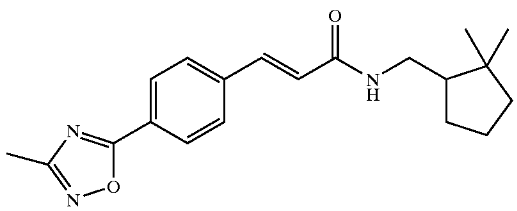 | $C_{20}H_{25}N_3O_2$: mp 160–161° C. |
| 57 | 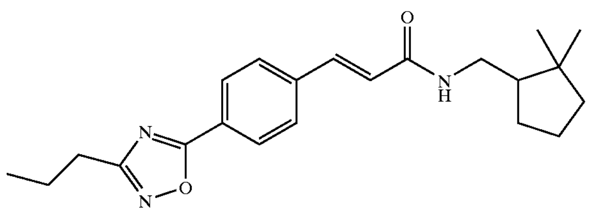 | $C_{22}H_{29}N_3O_2$: mp 147–149° C. |
| 58 | 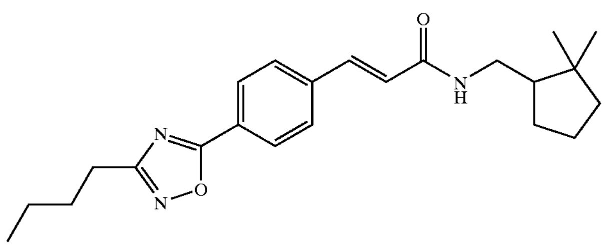 | $C_{23}H_{31}N_3O_2$: mp 146–148° C. |
| 59 | 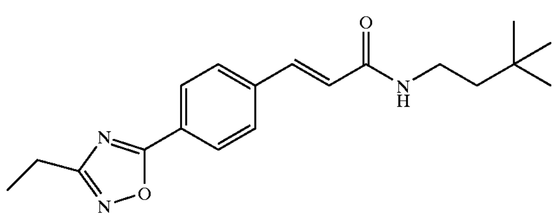 | $C_{19}H_{25}N_3O_2$: mp 162–163° C. |
| 60 | 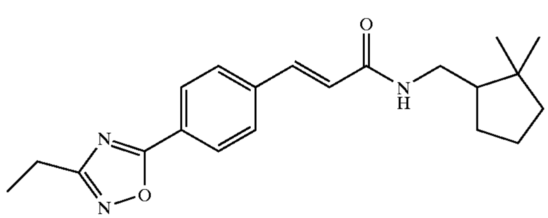 | $C_{21}H_{27}N_3O_2$: mp 145–1464° C. |
| 61 | 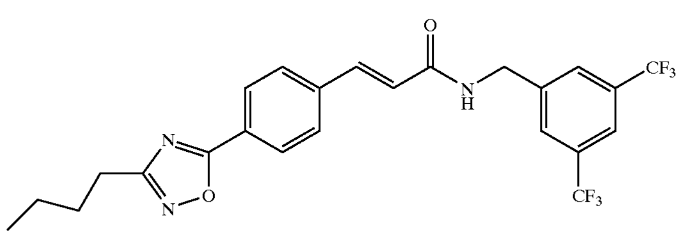 | $C_{24}H_{21}F_6N_3O_2$: mp 178–179° C. |

-continued

| Example # | Structure | Characterization |
|---|---|---|
| 62 | 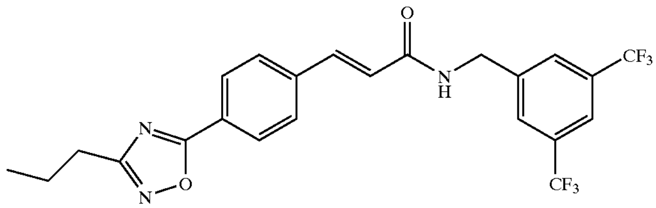 | $C_{23}H_{19}F_6N_3O_2$: mp 178–179° C. |
| 63 | 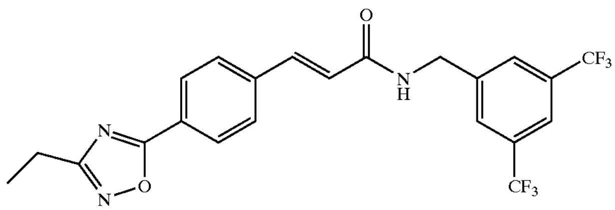 | $C_{22}H_{17}F_6N_3O_2$: MS: M + H = 468 |
| 64 | ENANTIOMER A | $C_{24}H_{33}N_3O_2$: mp 131–132° C. |
| 65 | ENANTIOMER B | $C_{24}H_{33}N_3O_2$: mp 130–131° C. |
| 66 | ENANTIOMER A | $C_{24}H_{33}N_3O_2$: mp 144–145° C. |
| 67 | ENANTIOMER B | $C_{24}H_{33}N_3O_2$: mp 140–141° C. |

Example 68

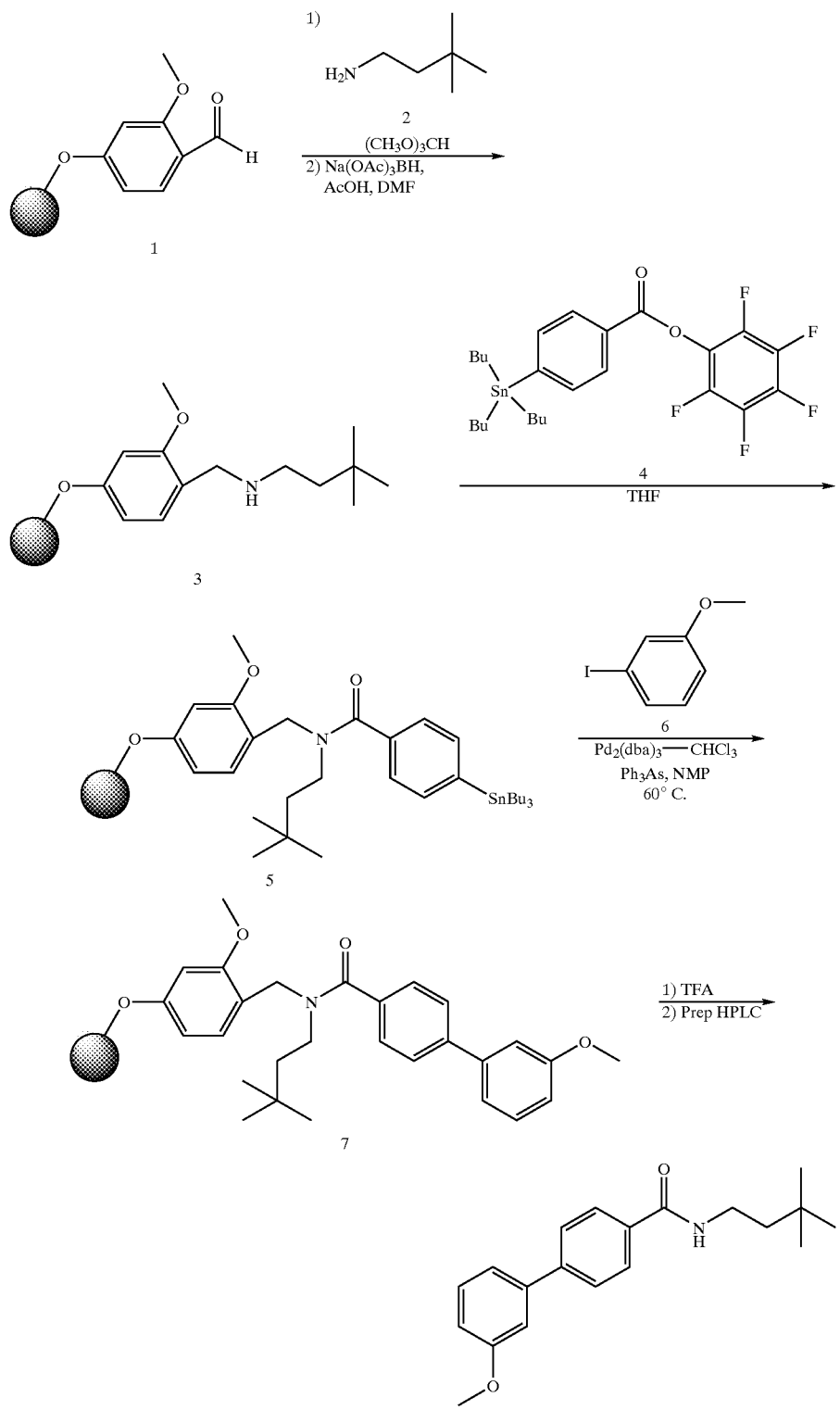

A. Resin 1

To a stirred suspension of NaH (5.25 g, 131 mmol) in 100 mL of dry DMF at 4° C. was added a solution of 4-hydroxy-2-methoxybenzaldehyde (20.0 g, 131 mmol) in 100 mL of dry DMF drop-wise via addition funnel over a period of 30 minutes. The addition funnel was washed with 30 mL of dry DMF which was added to the reaction flask. After stirring at 4° C. for one hour, the ice-water bath was removed and the reaction was allowed to warm to room temperature over the period of ½ hour. At the end of this period, tetra-n- butylammonium iodide (6.5 g, 17.6 mmol) was added followed by Merrifield resin (52.8 g, loading=1.24 mmol/g, 65.5 mmol). The reaction flask was immersed in an oil bath which was heated to 70° C. After 20 hours, the heating bath was removed and the reaction was allowed to cool to room temperature. The reaction was filtered with suction and the residual resin rinsed with water:DMF (3×200 mL), DMF (3×200 mL), THF (3×200 mL), methanol (2×200 mL). The resin was dried under (20 mm Hg) for 18 hours to yield 62.86 g of resin 1. Elemental analysis indicated less than 0.1% residual Cl.

B. Resin 2

Resin 1 (10 g, loading=1.08 mmol/g, 10.8 mmol) was weighed into a glass solid phase organic synthesis (SPOS) reaction vessel. The resin was swelled with dry DMF (50 mL) which was drained after 10 minutes. Dry DMF (60 mL) was then added followed by 3,3-dimethylbutylamine (3.0 g, 29.6 mmol). The reaction vessel was agitated on a wrist-action shaker for 10 minutes and trimethyl orthoformate (30 mL) was added. After agitating for 14 hours, the reaction was drained and 50 mL of dry DMF was added. The reaction was agitated for approximately 1 minute and drained. Dry DMF (10 mL) was added followed by sodium triacetoxyborohydride (6.35 g, 30 mmol) and acetic acid (0.60 mL, 1 mmol). After 6 hours of agitation, the reaction was drained and rinsed with DMF (3×50 mL), DMF-water (3×50 mL), DMF (3×50 mL), dichloromethane (3×50 mL), methanol (3×50 mL) and THF (3×50 mL). The resin was used in the next step without characterization.

C. Compound 4

To a stirred solution of pentafluorophenol (7.6 g, 41.3 mmol) in dry dichloromethane at 4° C. was added N,N-diisopropylethylamine (19.6 mL, 112.5 mmol) drop-wise via syringe over a period of 5 minutes. After 20 minutes, 4-iodobenzoyl chloride (10.0 g, 37.5 mmol) was added as a solid. The reaction was stirred at 4° C. for 2 hours and the ice-water bath was removed. The reaction was allowed to warm to room temperature over a half hour period. TLC analysis indicated complete consumption of starting material. The reaction was poured into 500 mL of dichloromethane which was washed with 1 N aq. HCl (3×200 mL), water (2×200 mL), sat. aq. sodium bicarbonate (3×200 mL) and brine (200 mL), dried over magnesium sulfate, filtered and stripped. The product was dried under vacuum to yield 15.35 g (37.0 mmol) of a white waxy solid. This material was dissolved in 100 mL of dry toluene and bis(tributyltin) (28 mL, 55.4 mmol) was added. The reaction mixture was degassed by bubbling with dry nitrogen for a period of 15 minutes. At the end of this period, tetrakistriphenylphosphine palladium (0) (427 mg, 0.37 mmol) was added. The reaction flask was fitted with a reflux condenser and immersed in an oil bath which was heated to 120° C. After stirring for 14 hours, the reaction was allowed to cool and filtered through a pad of silica. The solvent was removed in vacuo. The residual oil was purified by flash reverse-phase chromatography (YMC-gel, dichloromethane-acetonitrile). The tubes containing the product were pooled and concentrated to yield 16.31 g (28.3 mmol, 75.5% from 4-iodobenzoyl chloride) of 4.

D. Resin 5

Resin 3 (4.3 g, loading=0.99 mmol/g, 4.3 mmol) was transferred into a glass SPOS reaction vessel. The resin was swelled with 20 mL of dry THF. After 10 minutes the solvent was drained away and 5 mL of dry THF was added. A solution of compound 4 (4.9 g, 8.5 mmol) in 15 mL of dry THF was added via syringe. The reaction was agitated on a wrist-action shaker for 16 hours. The solvent was drained from the resin which was then washed with THF (3×40 mL), dichloromethane (3×40 mL), methanol (3×40 mL) and THF (3×40 mL). The resin was dried in vacuo at 20 mm Hg for 18 hr. The resin was used in the next step without further characterization.

E. Resin 7

Resin 5 (300 mg, 0.213 mmol) was transferred into a polypropylene reaction tube. Dry NMP (2 mL) was added followed by 3-iodoanisole (169 mg, 0.72 mmol), triphenylarsine (45 mg, 0.15 mmol) and tris(dibenzylideneacetone) dipalladium-(0)-chloroform adduct (35 mg, 0.034 mmol). The reaction was sealed and agitated at 275 rpm on an orbital shaker. The reaction was heated to 55° C. over a one hour period. After 14 hours, the reaction mixture was allowed to cool to room temperature. The solvent was drained and the resin was washed with DMF (3×5 mL), DMF-water (3×5 mL), dichloromethane (3×5 mL), THF (3×5 mL), methanol (3×5 mL), and dichloromethane (3×5 mL). The resin was suspended in dichloromethane (0.5 mL) and trifluoroacetic acid (3 mL). After 1 hour, the product was collected into a tared test-tube. The solvent was removed in vacuo. The crude product was purified by preparative HPLC using a YMC S3 ODS 20×100 mm column with a 30–100% B gradient over 10 minutes at a flow rate of 25 mL/minute (Solvent A: 90% water/10% methanol with 0.1% TFA; Solvent B 10% water/90% methanol with 0.1% TFA) to provide the title compound (3.7 mg).

Using the procedure described in Example 68, the following compounds were prepared.

| Example # | Structure | Characterization |
|---|---|---|
| 69 | 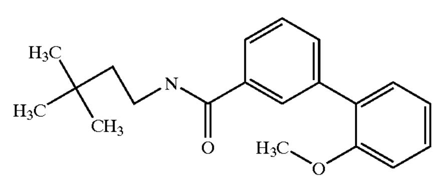 | $C_{20}H_{25}NO_2$<br>m/z 312 (M + H) |

-continued
| Example # | Structure | Characterization |
|---|---|---|
| 70 | 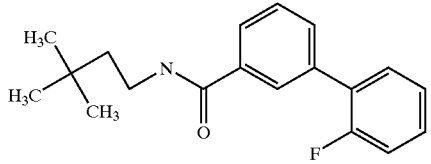 | C$_{19}$H$_{22}$FNO<br>m/z 300 (M + H) |
| 71 | 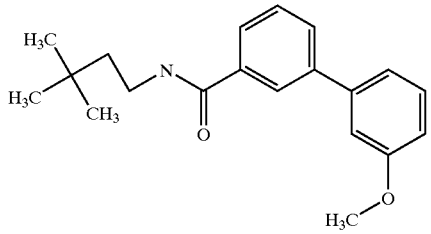 | C$_{20}$H$_{25}$NO$_2$<br>m/z 312 (M + H) |
| 72 | 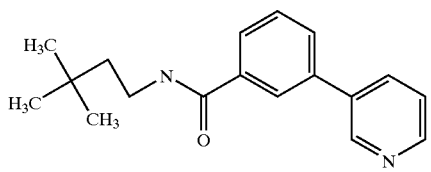 | C$_{18}$H$_{22}$N$_2$O<br>m/z 283 (M + H) |
| 73 | 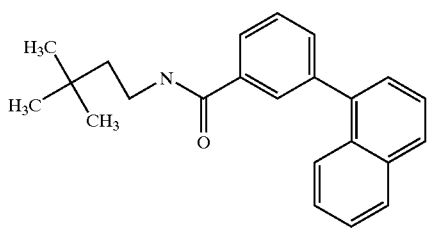 | C$_{23}$H$_{25}$NO<br>m/z 332 (M + H) |
| 74 | 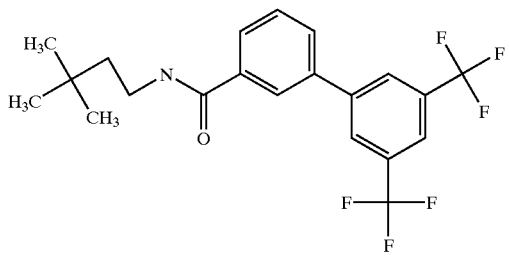 | C$_{21}$H$_{21}$F$_6$NO<br>m/z 418 (M + H) |
| 75 | 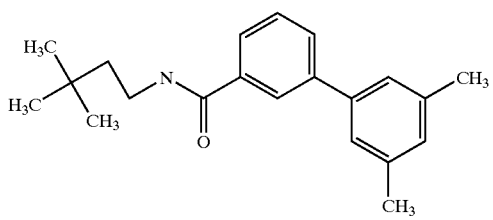 | C$_{21}$H$_{27}$NO<br>m/z 310 (M + H) |
| 76 | 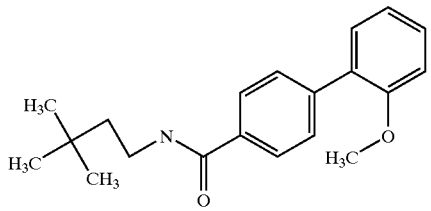 | C$_{20}$H$_{25}$NO$_2$<br>m/z 312 (M + H) |

-continued
| Example # | Structure | Characterization |
|---|---|---|
| 76a | 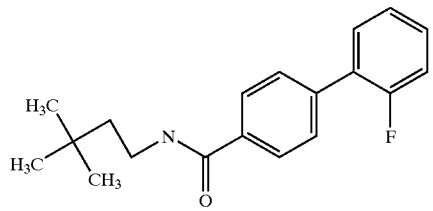 | C$_{19}$H$_{22}$FNO<br>m/z 300 (M + H) |
| 68 | 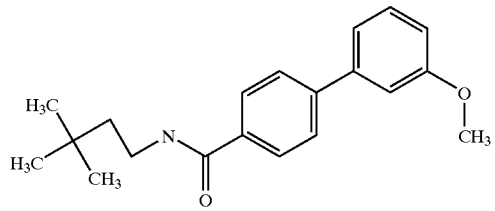 | C$_{20}$H$_{25}$NO$_2$<br>m/z 312 (M + H) |
| 77 | 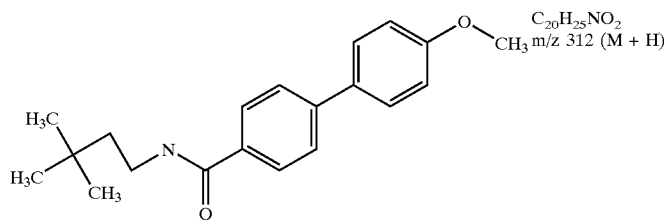 | C$_{20}$H$_{25}$NO$_2$<br>m/z 312 (M + H) |
| 78 | 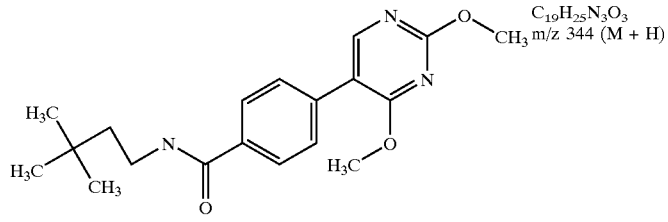 | C$_{19}$H$_{25}$N$_3$O$_3$<br>m/z 344 (M + H) |
| 79 | 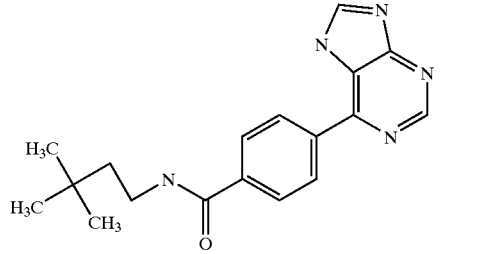 | C$_{18}$H$_{21}$N$_5$O<br>m/z 324 (M + H) |
| 80 | 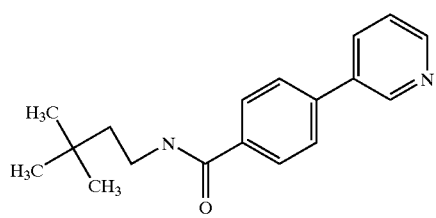 | C$_{18}$H$_{22}$N$_2$O<br>m/z 283 (M + H) |

-continued

| Example # | Structure | Characterization |
|---|---|---|
| 81 | 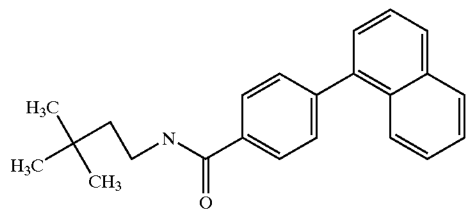 | $C_{23}H_{25}NO$<br>m/z 332 (M + H) |
| 82 | 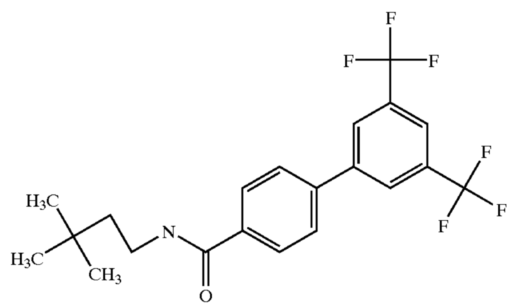 | $C_{21}H_{21}F_6NO$<br>m/z 418 (M + H) |
| 83 | 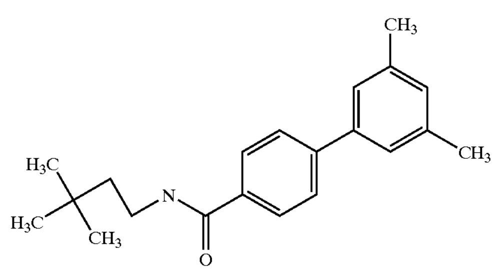 | $C_{21}H_{27}NO$<br>m/z 310 (M + H) |
| 84 | 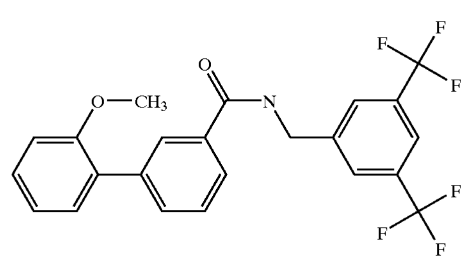 | $C_{23}H_{17}F_6NO_2$<br>m/z 452 (M − H) |
| 85 | 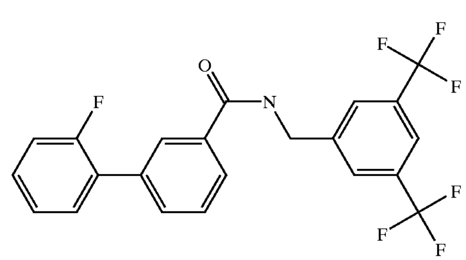 | $C_{22}H_{14}F_7NO$<br>m/z 442 (M + H) |
| 86 | 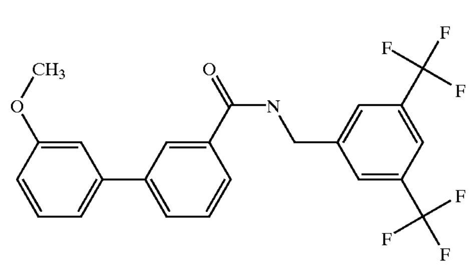 | $C_{23}H_{17}F_6NO_2$<br>m/z 454 (M + H) |

-continued
| Example # | Structure | Characterization |
|---|---|---|
| 87 | 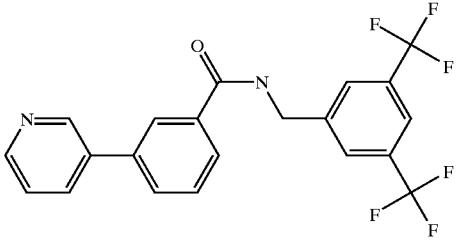 | C₂₁H₁₄F₆N₂O<br>m/z 425 (M + H) |
| 88 | 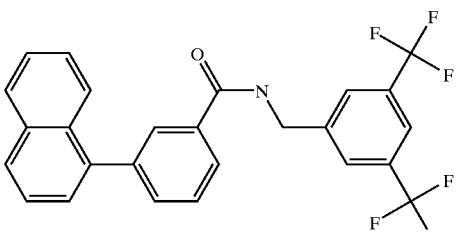 | C₂₆H₁₇F₆NO<br>m/z 474 (M + H) |
| 89 | 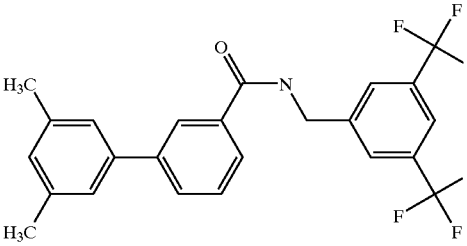 | C₂₄H₁₉F₆NO<br>m/z 452 (M + H) |
| 90 | 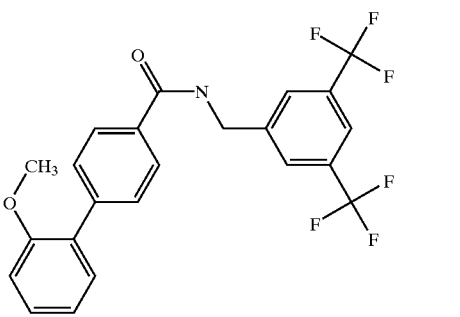 | C₂₃H₁₇F₆NO₂<br>m/z 454 (M + H) |
| 91 | 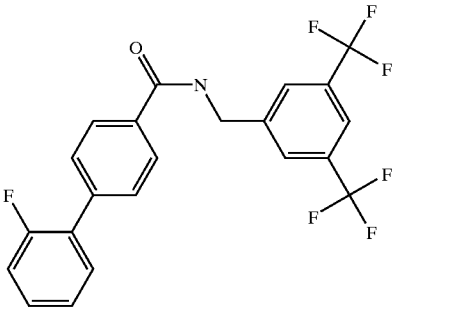 | C₂₂H₁₄F₇NO<br>m/z 442 (M + H) |

-continued

| Example # | Structure | Characterization |
|---|---|---|
| 92 | 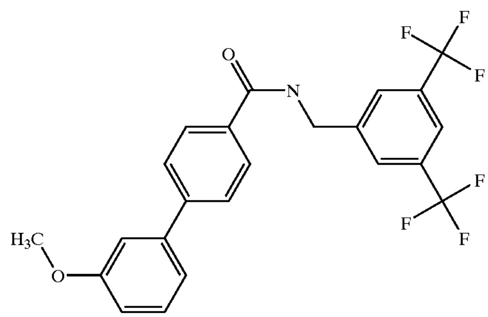 | C₂₃H₁₇F₆NO₂<br>m/z 454 (M + H) |
| 93 | 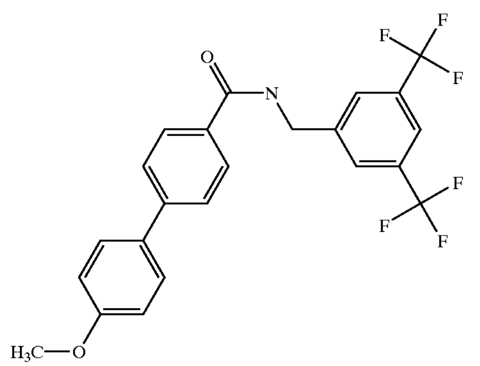 | C₂₃H₁₇F₆NO₂<br>m/z 454 (M + H) |
| 94 | 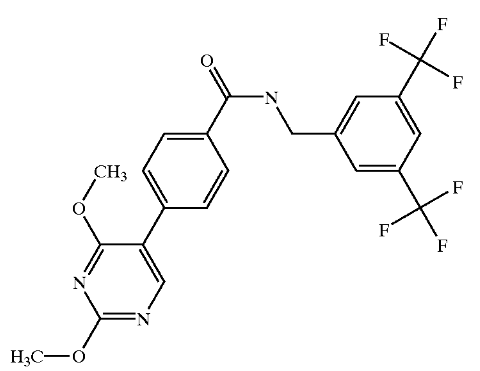 | C₂₂H₁₇F₆N₃O₃<br>m/z 486 (M + H) |
| 95 | 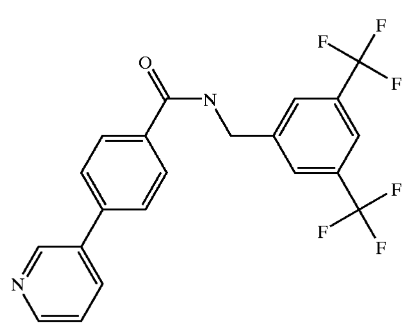 | C₂₁H₁₄F₆N₂O<br>m/z 425 (M + H) |

-continued
| Example # | Structure | Characterization |
|---|---|---|
| 96 | 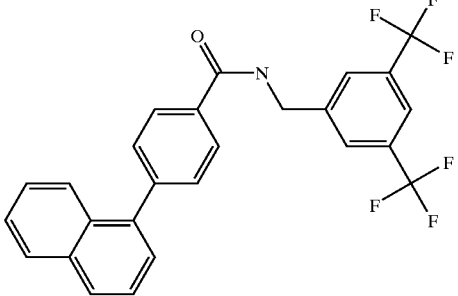 | C$_{26}$H$_{17}$F$_6$NO<br>m/z 472 (M − H) |
| 97 | 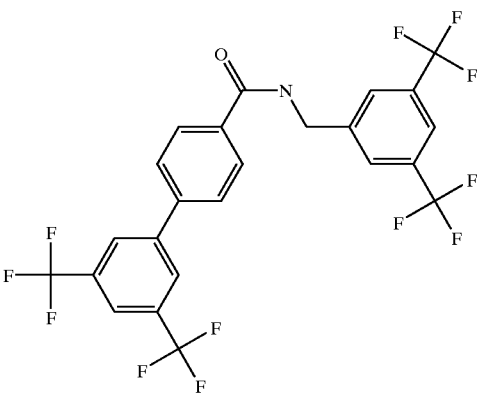 | C$_{24}$H$_{13}$F$_{12}$NO<br>m/z 558 (M − H) |
| 98 | 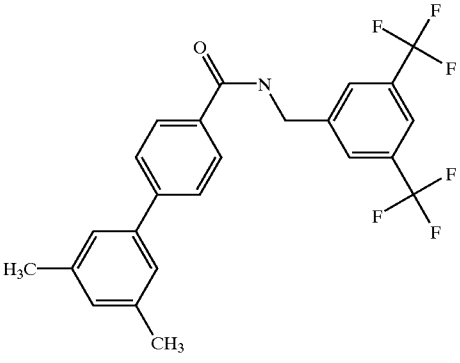 | C$_{24}$H$_{19}$F$_6$NO<br>m/z 452 (M + H) |

Example 99

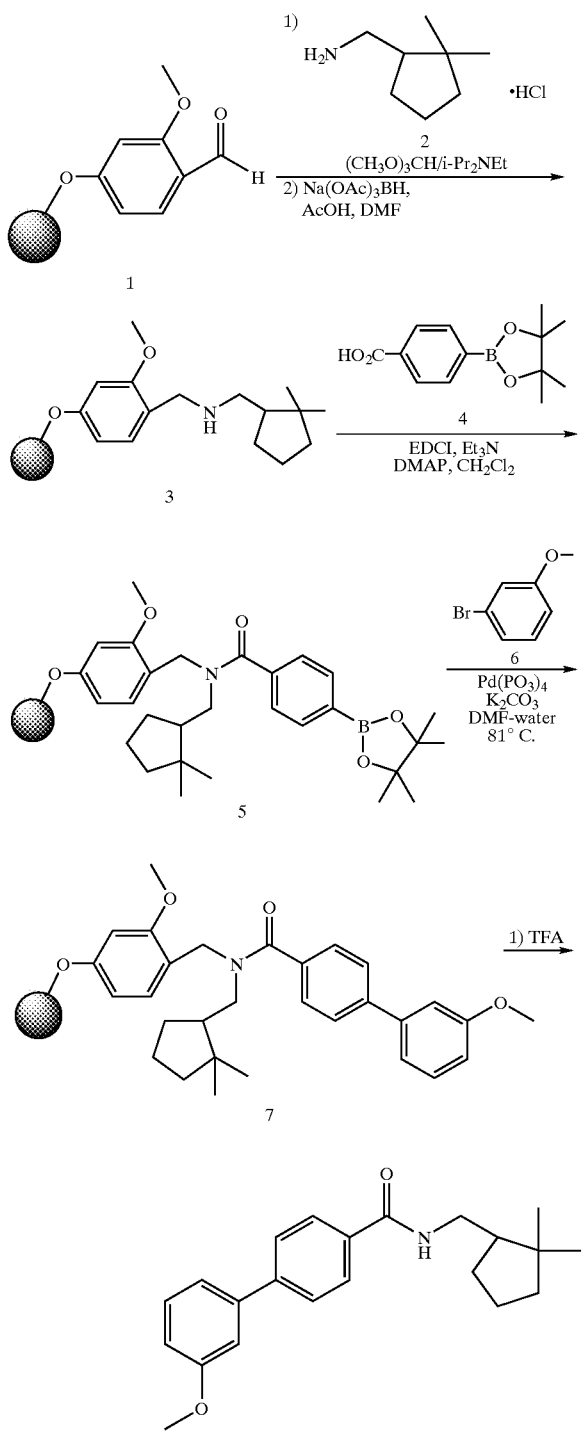

A. Resin 1

The title resin was prepared according to Example 68, part A.

B. Resin 3

5.0 g of resin 1 (loading=1.08 mmol/g, 5.4 mmol) was weighed into a glass SPOS reaction vessel. The resin was swelled with dry DMF (25 ml) which was drained after 10 min. Dry DMF (20 ml) was then added followed by amine 2 (2,2-dimethylmethylaminocyclopentane hydrochloride salt 1.33 g, 8.12 mmol) and N,N-diisopropylethylamine (4.7 ml, 27 mmol). The reaction vessel was agitated on a wrist-action shaker for 10 min. and trimethyl orthoformate (7 ml) was added. After agitating for 14 h, the reaction was drained and 20 ml of dry DMF was added. The reaction was agitated for approximately 1 min. and drained. 25 ml of dry DMF was added followed by sodium triacetoxyborohydride (3.40 g, 16.0 mmol) and acetic acid (1.0 ml, 1.6 mmol). After 6 h of agitation, the reaction was drained and rinsed with DMF (3×30 ml), DMF-water (3×30 ml), DMF (3×30 ml), dichloromethane (3×30 ml), methanol (3×30 ml) and THF (3×30 ml). The resin was used in the next step without characterization.

C. Boronate Ester 4

To a stirred mixture of 3-carboxyboronic acid (1.65 g, 10.0 mmol) in toluene (60 mL) was added pinacol (1.24 g, 10.5 mmol). The reaction flask was fitted with a Dean-Stark trap and a reflux condenser and immersed in an oil bath. The bath was heated to 160° C. After 20 hours, TLC indicated consumption of starting material. The reaction was allowed to cool. The solvent was removed in vacuo and the residue purified by flash column chromatography (silica, methanol-dichloromethane, 1:19). The appropriate fractions were collected to give the title compound (2.3 g, 93%).

D. Resin 5

Resin 3 (5.6 g, loading=0.97 mmol/g, 5.4 mmol) was transferred into a glass SPOS reaction vessel. The resin was swelled with 20 mL of dry dichloromethane. After 10 minutes the solvent was drained away and 5 mL of dry dichlormethane was added. The title 4 compound (1.75 g, 7.06 mmol) was added followed by 1-(3-dimethylaminopropyl)-3-ethylcarbodiimide hydrochloride (2.44 g, 7.01 mmol), triethylamine (3.75 ml, 26.9 mmol) and N,N-dimethylaminopyridine (50 mg, cat.). The reaction was agitated on a wrist-action shaker for 16 hour. The solvent was drained from the resin which was then washed with dichloromethane (3×40 mL), THF (3×40 mL), methanol (3×40 mL) and THF (3×40 mL).

E. Title Compound of Example 99

Resin 5 (200 mg, 0.158 mmol) was transferred into a glass reaction tube. DMF-water (9:1, 3 mL) was added followed by 3-bromoanisole (0.50 mL, 0.40 mmol), potassium carbonate (100 mg, 0.72 mmol) and tetrakis(triphenylphosphine)palladium-(0) (20 mg, 0.017 mmol). The reaction was sealed and agitated at 250 rpm on an orbital shaker. The reaction was heated to 81° C. over a one hour period. After 20 hours, the reaction was allowed to cool to room temperature. The solvent was drained and the resin was washed with DMF (3×5 mL), DMF-water (3×5 mL), DMF (3×5 mL), dichloromethane (3×5 mL), THF (3×5 mL), methanol (3×5 mL), and dichloromethane (3×5 mL). Dichloromethane (0.5 mL) was added followed by TFA (3 mL). After 1 hour, the product was collected into a tared test-tube. The solvent was removed from the cleavage product in vacuo. The product was reconstituted with 3 mL of dichloromethane and the solvent removed in vacuo to provide the title compound (24.1 mg).

Using the method described in Example 99, the following compounds were prepared.

| Example # | Structure | Characterization |
|---|---|---|
| 100 | 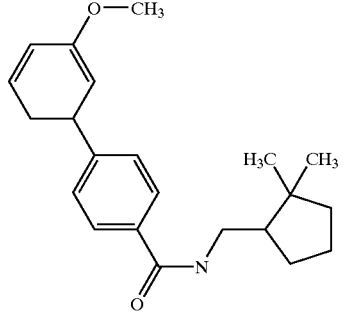 | $C_{22}H_{27}NO_2$<br>m/z 338 (M + H) |
| 101 | 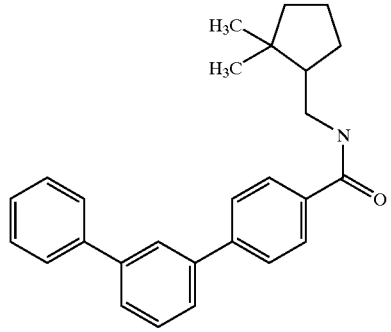 | $C_{27}H_{29}NO$<br>m/z 384 (M + H) |
| 102 | 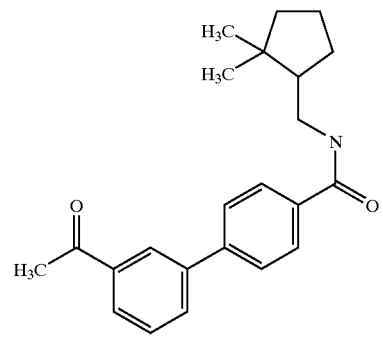 | $C_{23}H_{27}NO_2$<br>m/z 350 (M + H) |
| 103 | 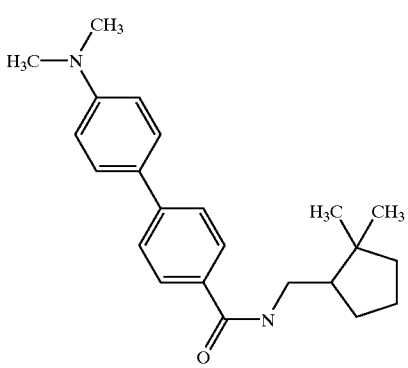 | $C_{23}H_{30}N_2O$<br>m/z 351 (M + H) |

| Example # | Structure | Characterization |
|---|---|---|
| 104 | 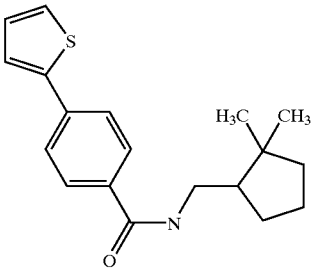 | $C_{19}H_{23}NOS$<br>m/z 314 (M + H) |
| 105 | 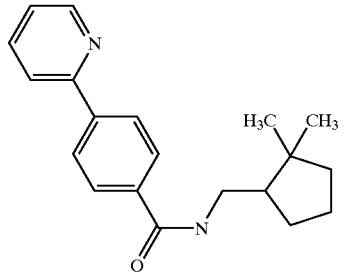 | $C_{20}H_{24}N_2O$<br>m/z 309 (M + H) |
| 106 | 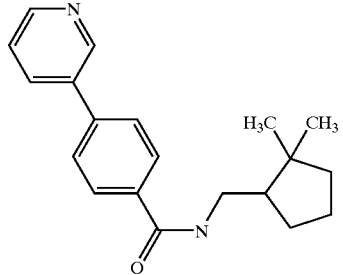 | $C_{20}H_{24}N_2O$<br>m/z 309 (M + H) |
| 107 | 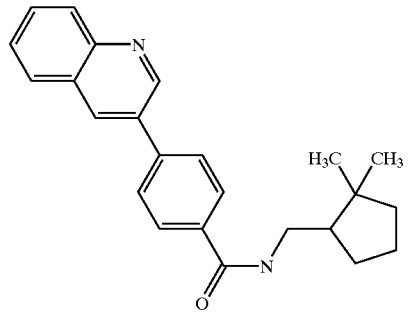 | $C_{24}H_{26}N_2O$<br>m/z 359 (M + H) |
| 108 | 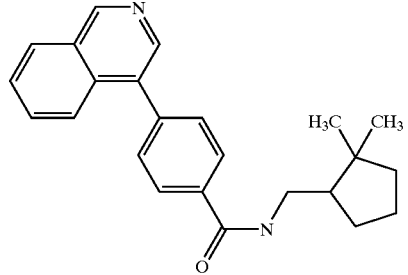 | $C_{24}H_{26}N_2O$<br>m/z 359 (M + H) |

-continued

| Example # | Structure | Characterization |
|---|---|---|
| 109 | 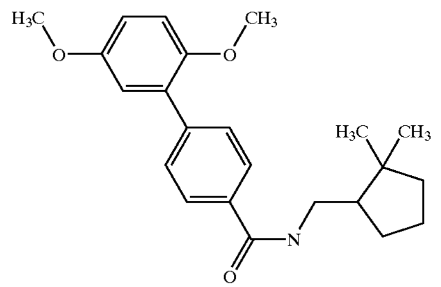 | C₂₃H₂₉NO₃<br>m/z 368 (M + H) |
| 110 | 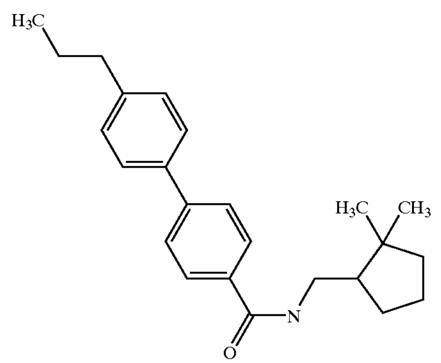 | C₂₄H₃₁NO<br>m/z 350 (M + H) |
| 111 | 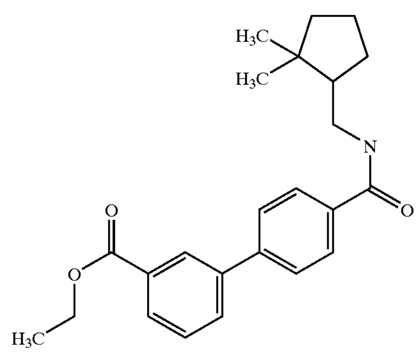 | C₂₄H₂₉NO₃<br>m/z 380 (M + H) |
| 112 | 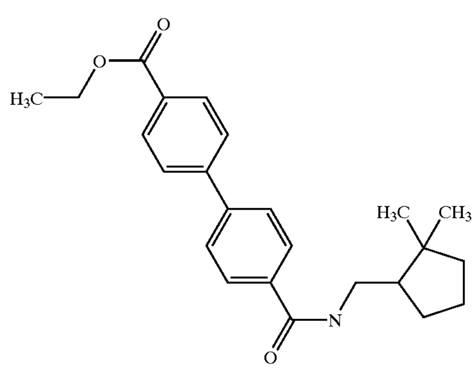 | C₂₄H₂₉NO₃<br>m/z 380 (M + H) |

-continued

| Example # | Structure | Characterization |
|---|---|---|
| 113 | 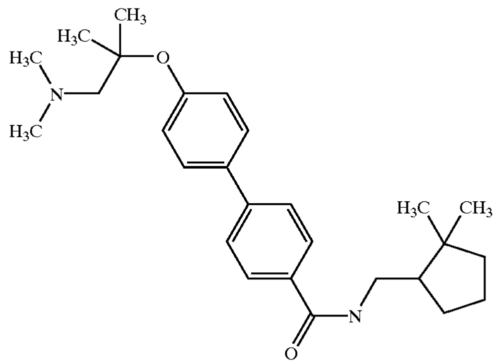 | $C_{27}H_{38}N_2O_2$<br>m/z 423 (M + H) |
| 114 | 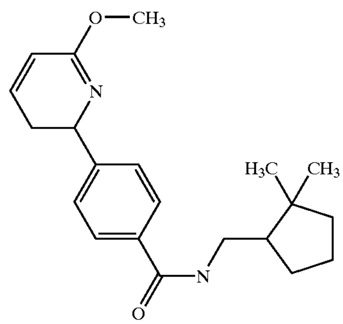 | $C_{21}H_{26}N_2O_2$<br>m/z 339 (M + H) |
| 115 | 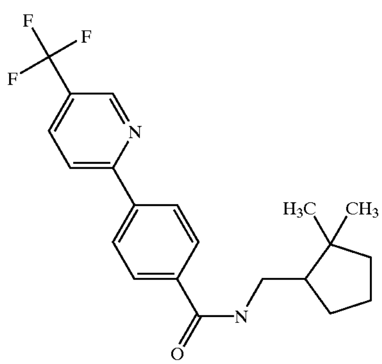 | $C_{21}H_{23}F_3N_2O$<br>m/z 377 (M + H) |
| 116 | 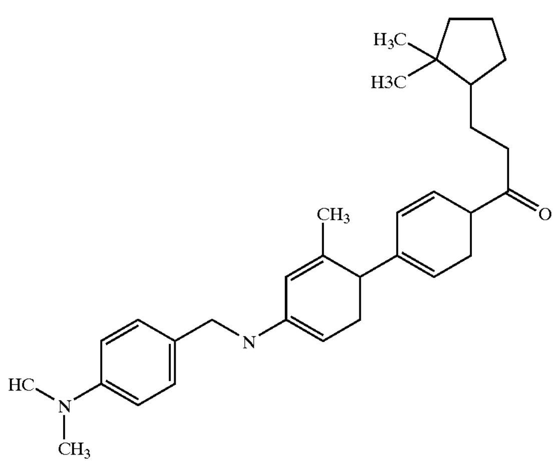 | $C_{31}H_{39}N_3O$<br>m/z 470 (M + H) |

-continued
| Example # | Structure | Characterization |
|---|---|---|
| 117 | 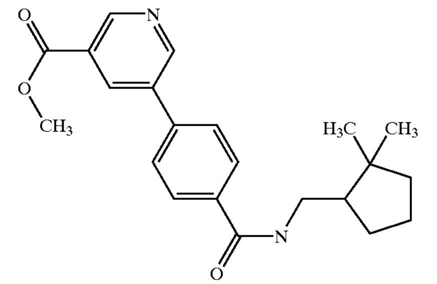 | $C_{22}H_{26}N_2O_3$<br>m/z 367 (M + H) |
| 118 | 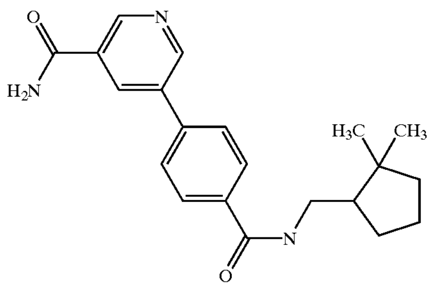 | $C_{21}H_{25}N_3O_2$<br>m/z 352 (M + H) |
Example 120
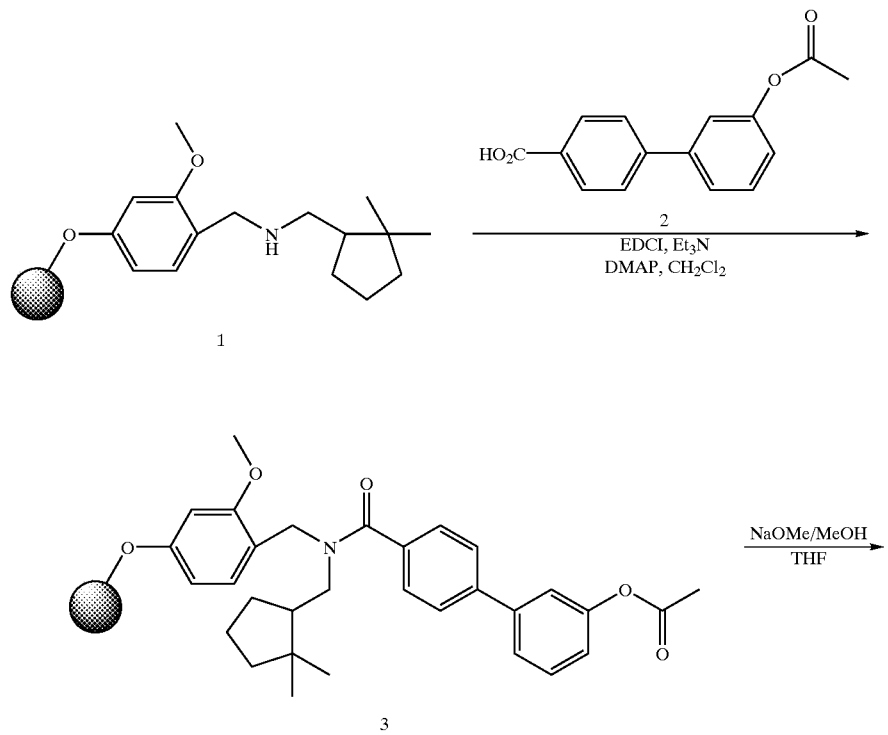

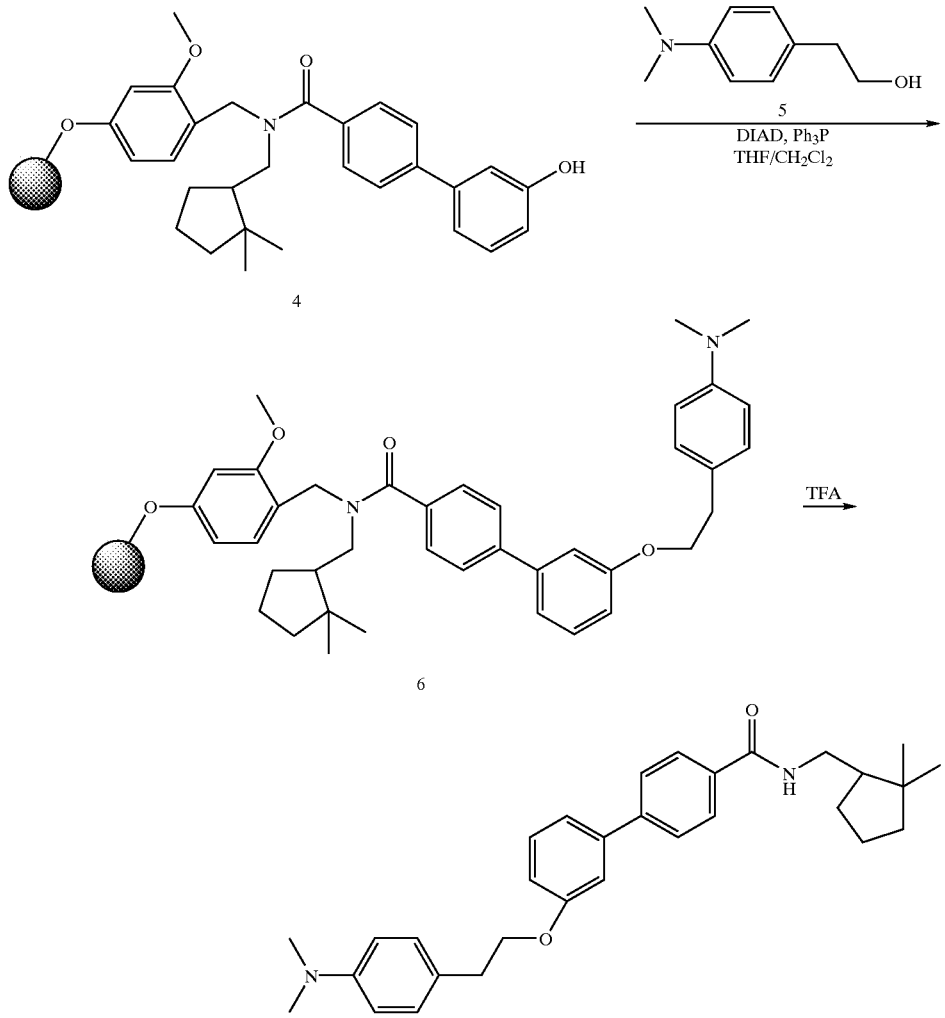

A. Compound 2

A solution of 3-methoxybenzene boronic acid (4.0 g, 26.3 mmol) and benzyl-4-bromobenzoate (7.66 g, 26.3 mmol) in toluene (50 mL) was degassed by bubbling nitrogen through for 15 minutes. A solution of potassium carbonate in water (2 M, 13.1 mL, 26.2 mmol) was added followed by the addition of tetrakis(triphenylphosphine)palladium (0) (0.66 g, 0.57 mmol). The reaction flak was fitted with a reflux condenser and immersed in an oil bath which was heated to 150° C. After stirring under reflux for 14 hours, the reaction was allowed to cool and poured into an EtOAc (500 mL)—water (200 mL) mixture. The layers were separated and the organic layer washed with brine, stirred over magnesium sulfate/charcoal for 15 minutes, filtered through Celite and concentrated in vacuo to give 7.5 g of a white solid which was dissolved in ethanol and added to a pressure flask. Palladium-hydroxide on carbon (10%, 750 mg) was added. The flask was placed on a Parr shaker and agitated under a hydrogen atmosphere (63 psi) for 4 hours. At the end of this time, nitrogen was bubbled through the reaction mixture for 15 minutes. The reaction mixture was filtered through a pad of Celite and concentrated in vacuum to afford 5.32 g of a white solid. Dry dichloromethane (100 mL) was added to the flask containing the above material. The flask was cooled to −78° C. in a dry ice—acetone bath and a solution of boron tribromide in dichloromethane (1 M, 57 mL, 57 mmol) was added via syringe over a period of 20 minutes. The reaction was stirred at −78° C. for 2 hours. At this time the dry ice-acetone bath was replaced with an ice-water bath and the reaction was allowed to warm to 4° C. over the period of 1 hour. At this time, the reaction was placed in the dry ice-acetone bath. After 10 minutes, methanol (10 mL) was added via syringe over a 2 minute period. The reaction was poured into a dichloromethane (500 mL)—water (100 mL) mixture. The layers were separated and the aqueous layer was extracted with dichloromethane (5×200 mL). The dichloromethane extracts were combined, dried over magnesium sulfate and concentrated in vacuo. The resulting material was purified by flash column chromatography (silica, 9:1—dichloromethane:methanol). The appropriate fractions were pooled and concentrated in vacuo to afford 2.99 g of a white solid. The above material was suspended in acetic anhydride and 3 drops of an acetic acid:sulfuric acid (1:1) mixture were added. The reaction flask was immersed in an oil bath which was heated to 160° C. for 1.5 hours. At the end of this time, the reaction was poured over an ice (50 g)/water (50 mL) mixture. The flask containing this mixture was heated at 55° C. with stirring for 1 hour. Over this period a white precipitate appeared in the flask. The flask was cooled in an ice-water bath for ½ hour and the precipitate was collected by vacuum filtration. This procedure yielded 3.3 g of 2.

B. Resin 3

Resin 1 (the title A resin of example 99, 5.6 g, loading= 0.97 mmol/g, 5.4 mmol) was transferred into a glass SPOS reaction vessel. The resin was swelled with 20 mL of dry dichloromethane. After 10 minutes the solvent was drained away and 25 mL of dry dichloromethane was added. Acid 2 (2.07 g, 10.5 mmol) was added followed by 1-(3-dimethylaminopropyl)-3-ethylcarbodiimide hydrochloride (2.82 g, 10.5 mmol), triethylamine (1.8 mL, 12.9 mmol) and N,N-dimethylaminopyridine (20 mg, cat.). The reaction was agitated on a wrist-action shaker for 16 hours. The solvent was drained from the resin which was then washed with dichloromethane (3×40 mL), THF (3×40 mL), methanol (3×40 mL) and THF (3×40 mL).

C. Resin 4

6.0 g of resin 3 (loading=0.78 mmol/g, 4.7 mmol) was transferred into a glass SPOS reaction vessel. The resin was swelled with 50 mL of THF and 20 mL of a solution of sodium methoxide in methanol (0.5 M, 10 mmol) was added. The reaction was agitated for 20 hours and drained. The resin was washed with THF (40 mL) which was drained. A solution of acetic acid in THF (1:9) was then added. After agitating for ½ hour, the reaction was drained and the resin was then washed with dichloromethane (3×40 mL), THF (3×40 mL), methanol (3×40 mL) and THF (3×40 mL).

D. The Title Compound of Example 120

Resin 4 (200 mg, 0.164 mmol) was transferred into a polypropylene reaction tube which was fitted into a solid-phase reactor. The resin was swelled by the addition of 2.0 mL of dichloromethane. To the resin was added 4-(dimethylamino)-phenethyl alcohol (136 mg, 0.82 mmol), 1 mL of a solution of triphenylphosphine in THF (0.82 M, 0.82 mmol) and 1 mL of a solution of diisopropyl azodicarboxylate in THF (0.82 M, 0.82 mmol). The reaction block was agitated at 275 rpm for 20 hours. At the end of this period the solvent was drained and the resin was washed with DMF (3×5 mL), DMF-water (3×5 mL), DMF (3×5 mL), dichloromethane (3×5 mL), THF (3×5 mL), methanol (3×5 mL), and dichloromethane (3×5 mL). Dichloromethane (0.5 mL) was added followed by trifluoroacetic acid (3 mL). After 1 hour, the product was collected into a tared test-tube. The solvent was removed from the cleavage product in vacuo. The product was reconstituted with 3 mL of dichloromethane and the solvent removed in vacuo to provide the title compound (30.3 mg).

Using the procedure described in example 120, the following compounds were prepared.

| Example # | Structure | Characterization |
|---|---|---|
| 121 | 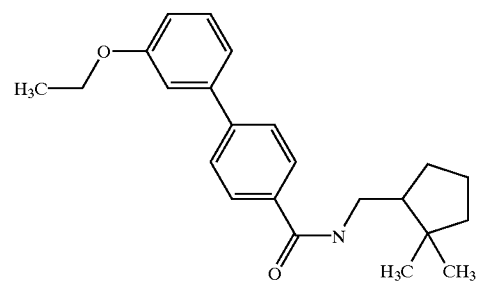 | $C_{23}H_{29}NO_2$<br>m/z 352 (M + H) |
| 122 | 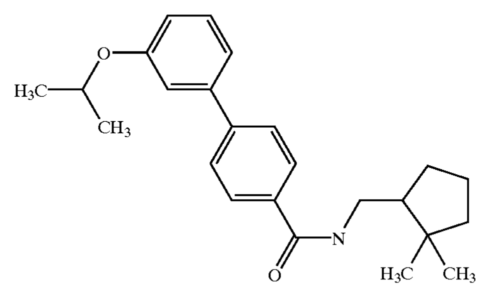 | $C_{24}H_{31}NO_2$<br>m/z 366 (M + H) |
| 123 | 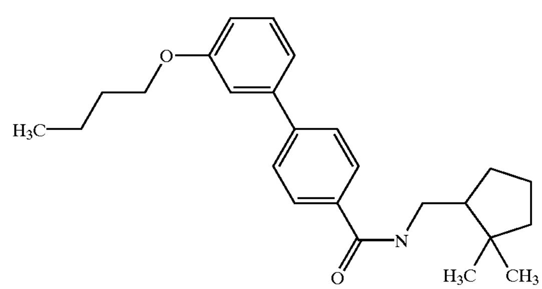 | $C_{25}H_{33}NO_2$<br>m/z 380 (M + H) |

-continued

| Example # | Structure | Characterization |
|---|---|---|
| 124 | 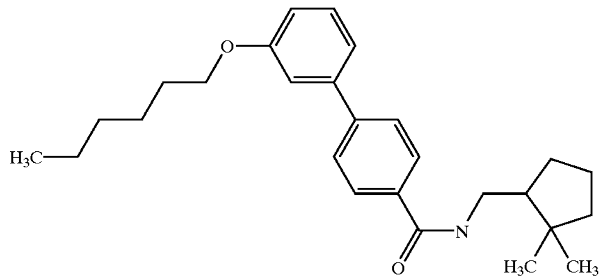 | $C_{27}H_{37}NO_2$<br>m/z 408 (M + H) |
| 125 | 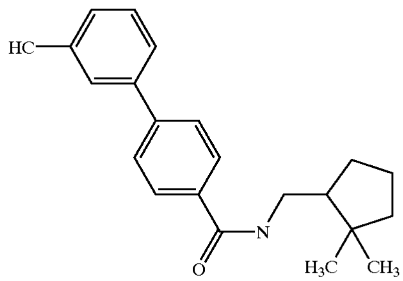 | $C_{21}H_{25}NO_2$<br>m/z 324 (M + H) |
| 126 | 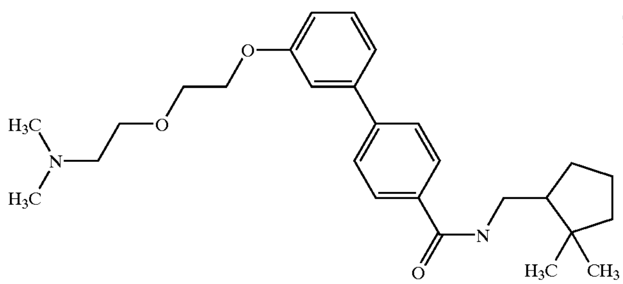 | $C_{27}H_{38}N_2O_3$<br>m/z 439 (M + H) |
| 127 | 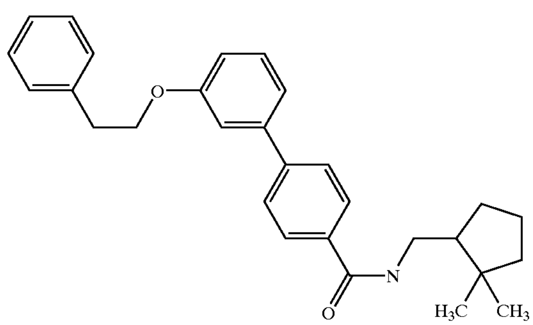 | $C_{29}H_{33}NO_2$<br>m/z 428 (M + H) |
| 120 | 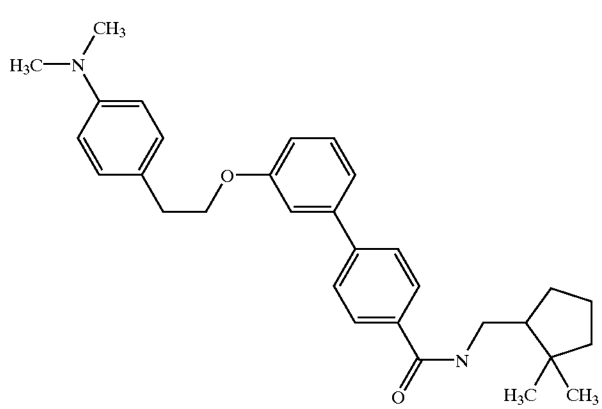 | $C_{31}H_{38}N_2O_2$<br>m/z 471 (M + H) |

-continued

| Example # | Structure | Characterization |
|---|---|---|
| 128 | 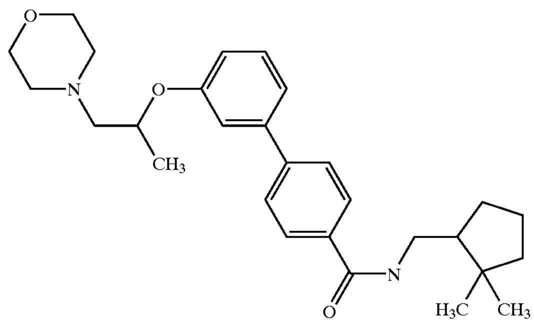 | $C_{28}H_{38}N_2O_3$<br>m/z 451 (M + H) |
| 129 | 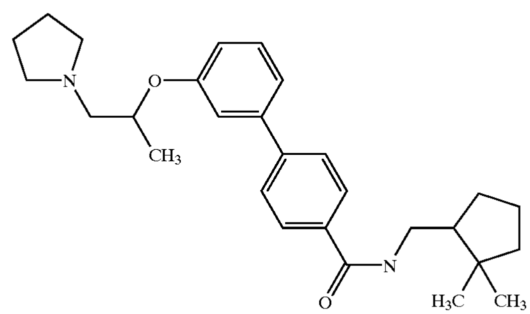 | $C_{28}H_{38}N_2O_2$<br>m/z 435 (M + H) |
| 130 | 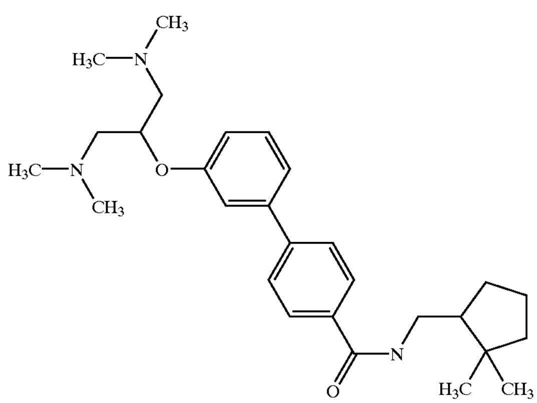 | $C_{28}H_{41}N_3O_2$<br>m/z 452 (M + H) |
| 131 | 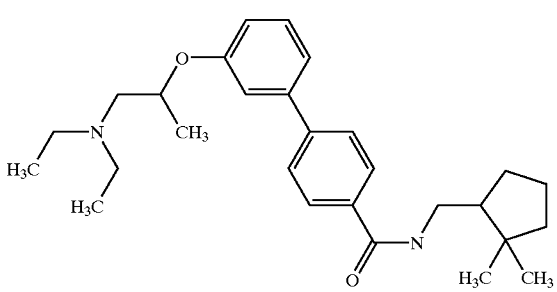 | $C_{28}H_{40}N_2O_2$<br>m/z 437 (M + H) |

| Example # | Structure | Characterization |
|---|---|---|
| 132 | 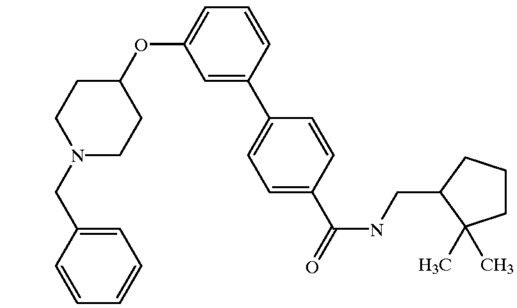 | $C_{33}H_{40}N_2O_2$<br>m/z 497 (M + H) |
| 133 | 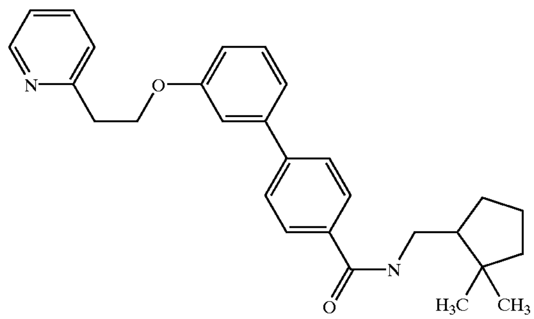 | $C_{28}H_{32}N_2O_2$<br>m/z 429 (M + H) |
| 134 | 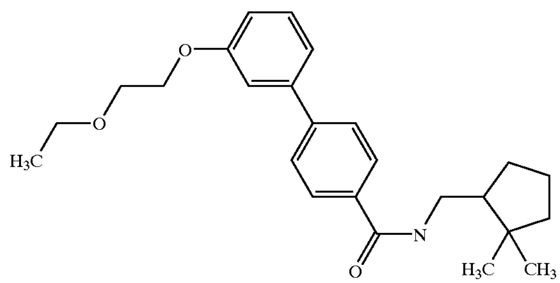 | $C_{25}H_{33}NO_3$<br>m/z 396 (M + H) |
| 135 | 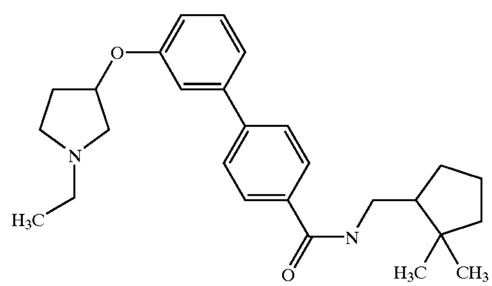 | $C_{27}H_{36}N_2O_2$<br>m/z 421 (M + H) |
| 136 | 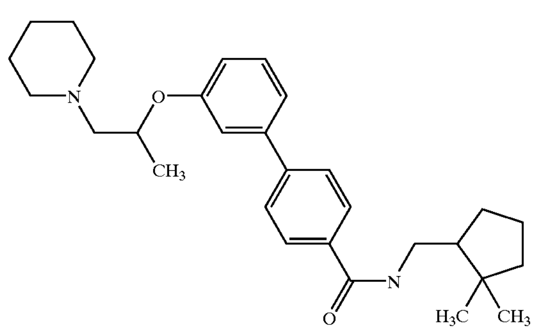 | $C_{29}H_{40}N_2O_2$<br>m/z 449 (M + H) |

-continued

| Example # | Structure | Characterization |
|---|---|---|
| 137 | 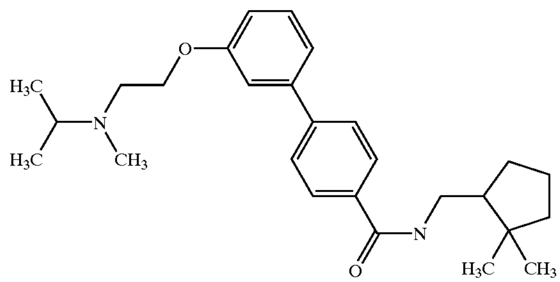 | C₂₇H₃₈N₂O₂<br>m/z 423 (M + H) |
| 138 | 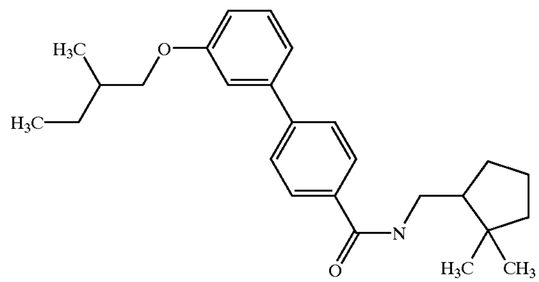 | C₂₆H₃₅NO₂<br>m/z 394 (M + H) |
| 139 | 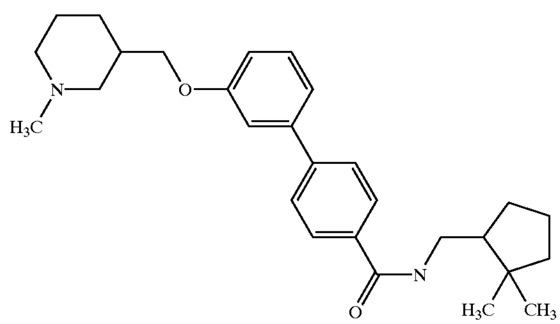 | C₂₈H₃₈N₂O₂<br>m/z 435 (M + H) |
| 140 | 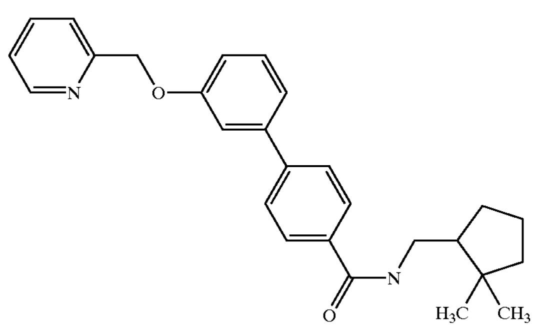 | C₂₇H₃₀N₂O₂<br>m/z 415 (M + H) |
| 141 | 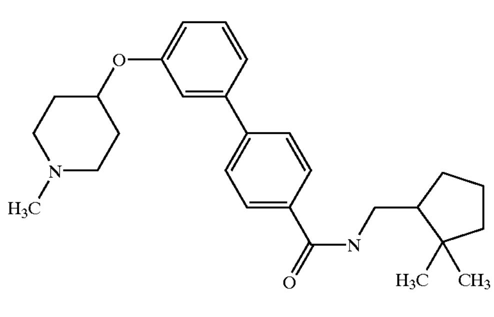 | C₂₇H₃₆N₂O₂<br>m/z 421 (M + H) |

| Example # | Structure | Characterization |
|---|---|---|
| 142 | 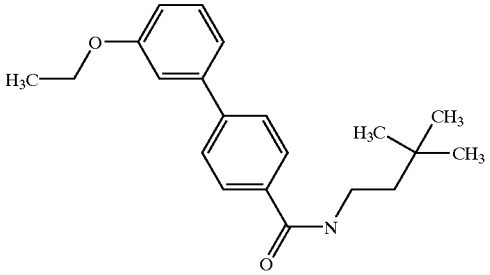 | $C_{21}H_{27}NO_2$<br>m/z 326 (M + H) |
| 143 | 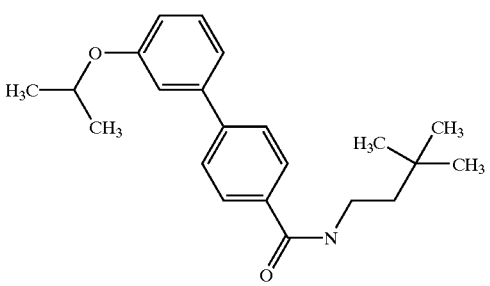 | $C_{22}H_{29}NO_2$<br>m/z 340 (M + H) |
| 144 | 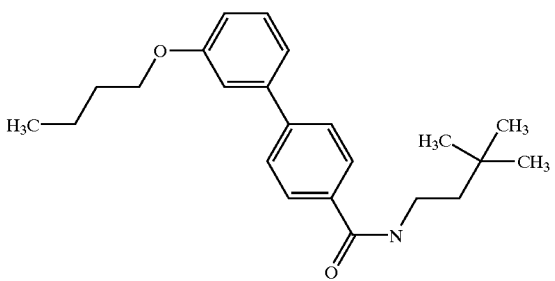 | $C_{23}H_{31}NO_2$<br>m/z 354 (M + H) |
| 145 | 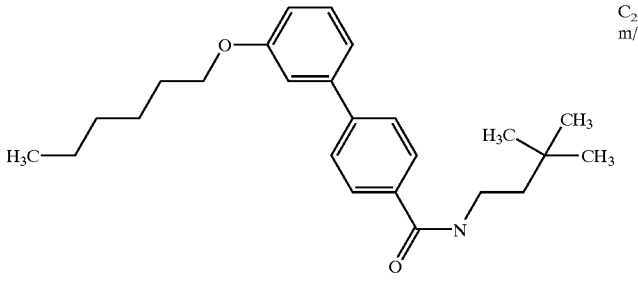 | $C_{25}H_{35}NO_2$<br>m/z 382 (M + H) |
| 146 | 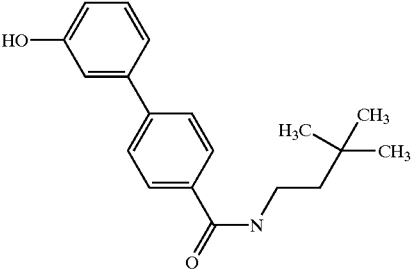 | $C_{21}H_{23}NO_2$<br>m/z 298 (M + H) |

-continued

| Example # | Structure | Characterization |
|---|---|---|
| 147 | 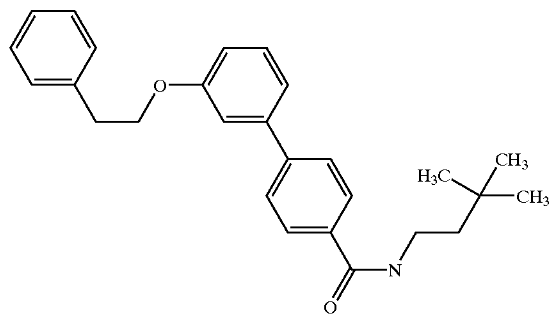 | C₂₇H₃₁NO₂<br>m/z 402 (M + H) |
| 148 | 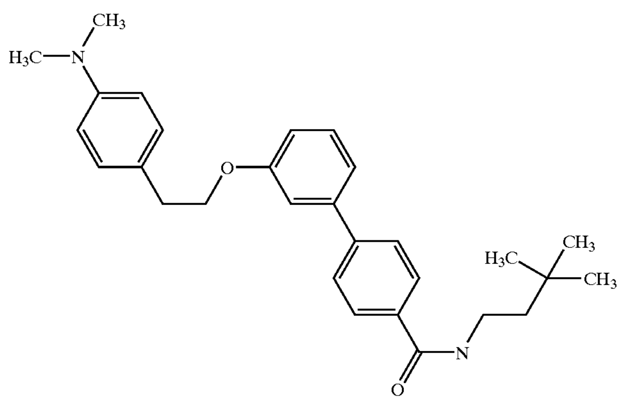 | C₂₉H₃₆N₂O₂<br>m/z 445 (M + H) |
| 149 | 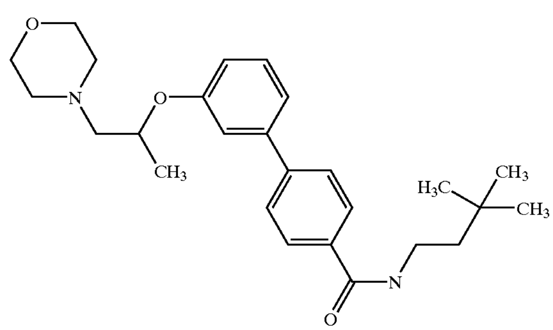 | C₂₆H₃₆N₂O₃<br>m/z 425 (M + H) |
| 150 | 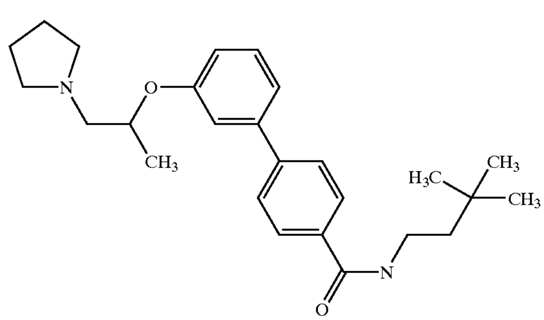 | C₂₆H₃₆N₂O₂<br>m/z 409 (M + H) |

-continued

| Example # | Structure | Characterization |
|---|---|---|
| 151 | 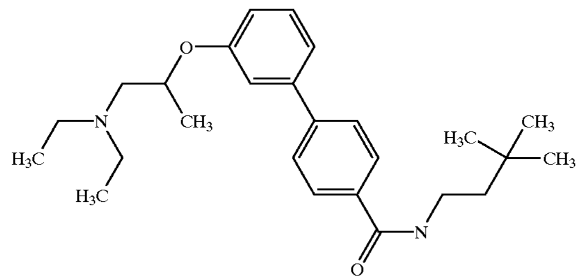 | $C_{26}H_{38}N_2O_2$<br>m/z 411 (M + H) |
| 152 | 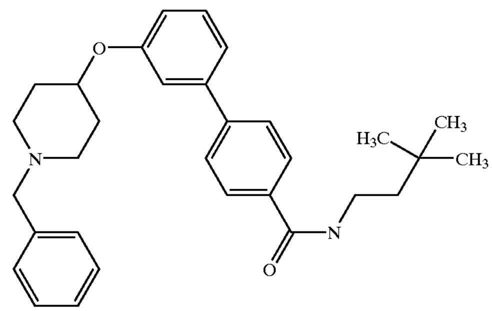 | $C_{31}H_{38}N_2O_2$<br>m/z 471 (M + H) |
| 153 | 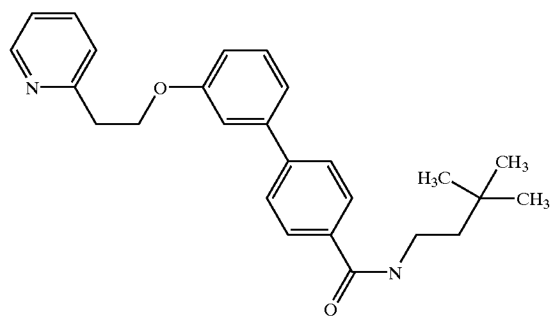 | $C_{26}H_{30}N_2O_2$<br>m/z 403 (M + H) |
| 154 | 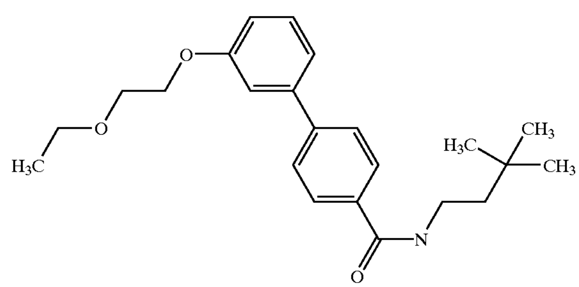 | $C_{23}H_{31}NO_3$<br>m/z 370 (M + H) |
| 155 | 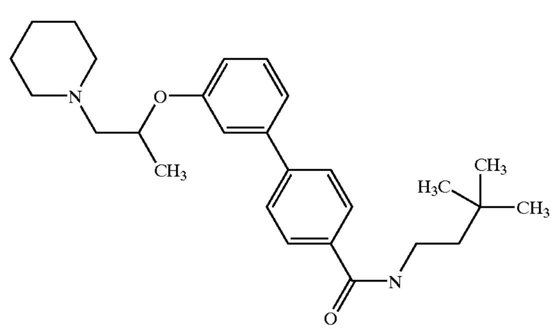 | $C_{27}H_{38}N_2O_2$<br>m/z 423 (M + H) |

What is claimed is:

1. A method of treating cardiac arrhythmia which comprises administering to a mammal in need thereof an effective amount of a compound of the formula

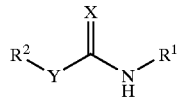

where

X is oxygen;

Y is a single bond;

$R^1$ is alkyl, alkenyl, alkynyl, aryl, cycloalkyl, (aryl)alkyl or (cycloalkyl)alkyl; and $R^2$ is aryl which cannot be substituted with OH or a phenolic ester group and must be substituted with a heterocyclo group at the 4-position which is a fully saturated or unsaturated ring of five or six atoms containing one or two oxygen and/or sulfur atoms and/or one to four nitrogen atoms provided that the total number of hetero atoms in the ring is four or less, or the heterocyclic group is a bicyclic ring wherein the five or six-membered ring containing oxygen and/or sulfur and/or nitrogen atoms as defined above is fused to a benzene ring;

with the proviso that (1) the heterocyclo group substituted on the $R^2$ aryl is exclusive of

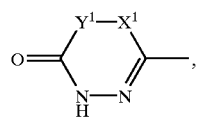

where $X^1$ is —$CR_aR_b$— and $Y^1$ is O, S or —$NR_c$— where $R_a$, $R_b$, and $R_c$, which may be the same or different, are independently H or $C_{1-4}$alkyl;

(2) $R^1$ is exclusive of aminoalkyl;

(3) where $R^1$ is cycloalkyl or (cycloalkyl)alkyl, the cycloalkyl group is unsubstituted or is substituted with alkyl or hydroxy, where the alkyl is unsubstituted or is substituted with halo, alkoxy, aryl, cycloalkyl, hydroxy, nitro, cyano, thiol or alkylthio; and (4) where $R^1$ is aryl, then the heterocyclic group substituted on the $R^2$ aryl is exclusive of

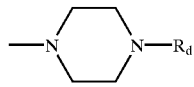

where $R_d$ is H or alkyl.

2. A compound of the formula

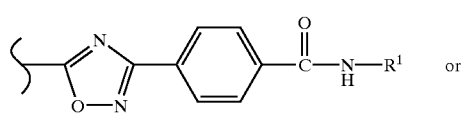

or

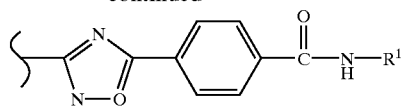

wherein the above oxadiazolyl ring is optionally substituted with alkyl, aryl, alkylthio, alkoxy, halo, nitro, keto, cyano, hydroxy, azo, oxo, thiazo, amino, substituted amino, carboxylic acid, carboxylic ester, or alkoxy further substituted with a carboxylic acid or a five- to eight-membered ring optionally containing 1 to 4 heteroatoms selected from oxygen, nitrogen and sulfur, optionally substituted by alkyl or halogen;

and $R^1$ is (cycloalkyl)alkyl, or a pharmaceutically acceptable salt thereof;

with the proviso that in the $R^1$ (cycloalkyl)alkyl, the cycloalkyl group is unsubstituted or is substituted with alkyl or hydroxy, where the alkyl is unsubstituted or is substituted with halo, alkoxy, aryl, cycloalkyl, hydroxy, nitro, cyano, thiol or alkylthio.

3. A compound which is:

N-(3,3-dimethylbutyl)-4-(1H-indol-1-yl)benzamide;

4-(3-butyl-1,2,4-oxadiazol-5-yl)-N-(3, 3-dimethylbutyl)-benzamide;

N-(3,3-dimethylcyclopentyl)-4-(1H-indol-1-yl)benzamide;

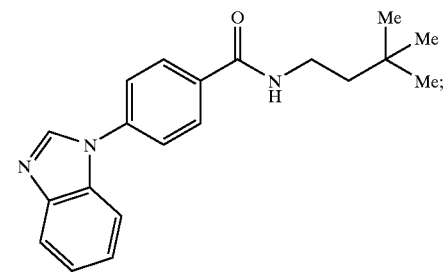

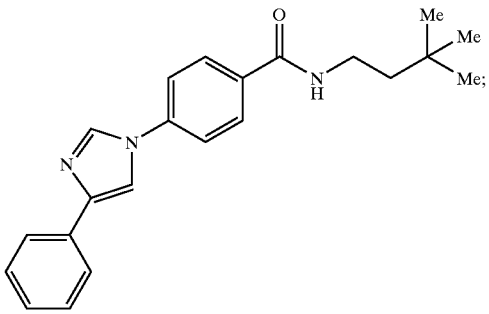

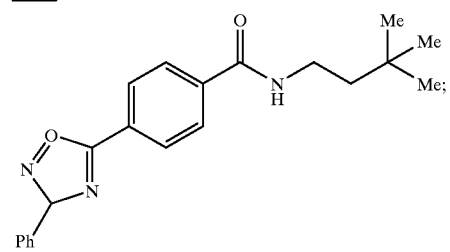

143
-continued
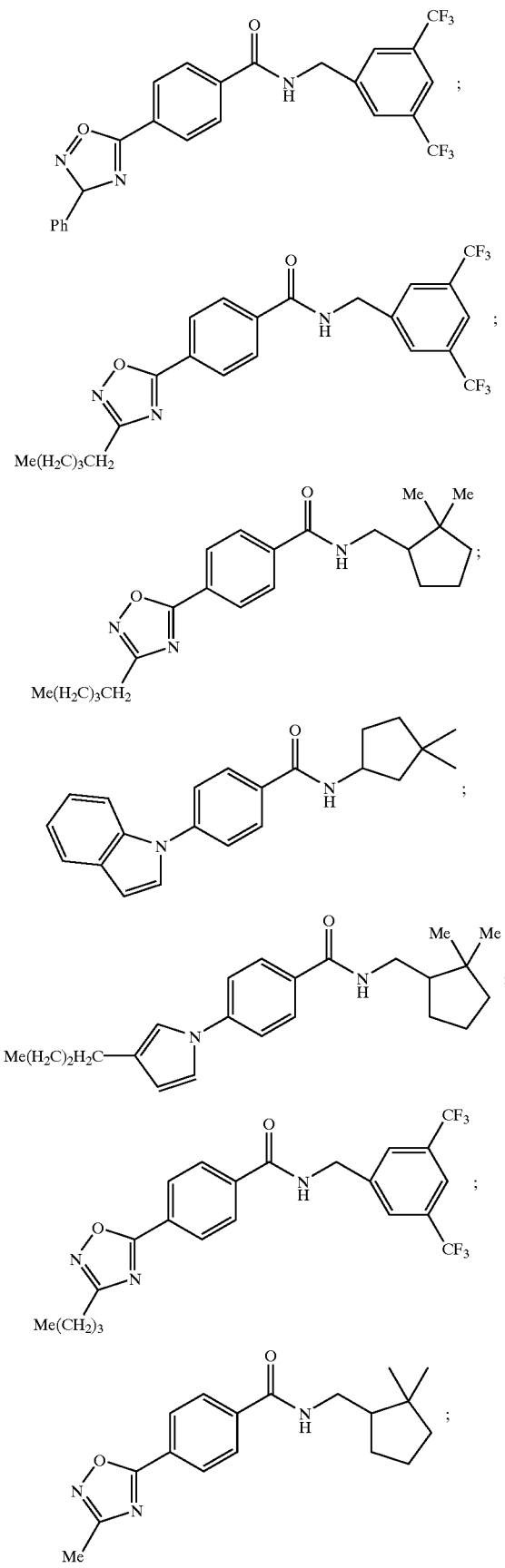
144
-continued
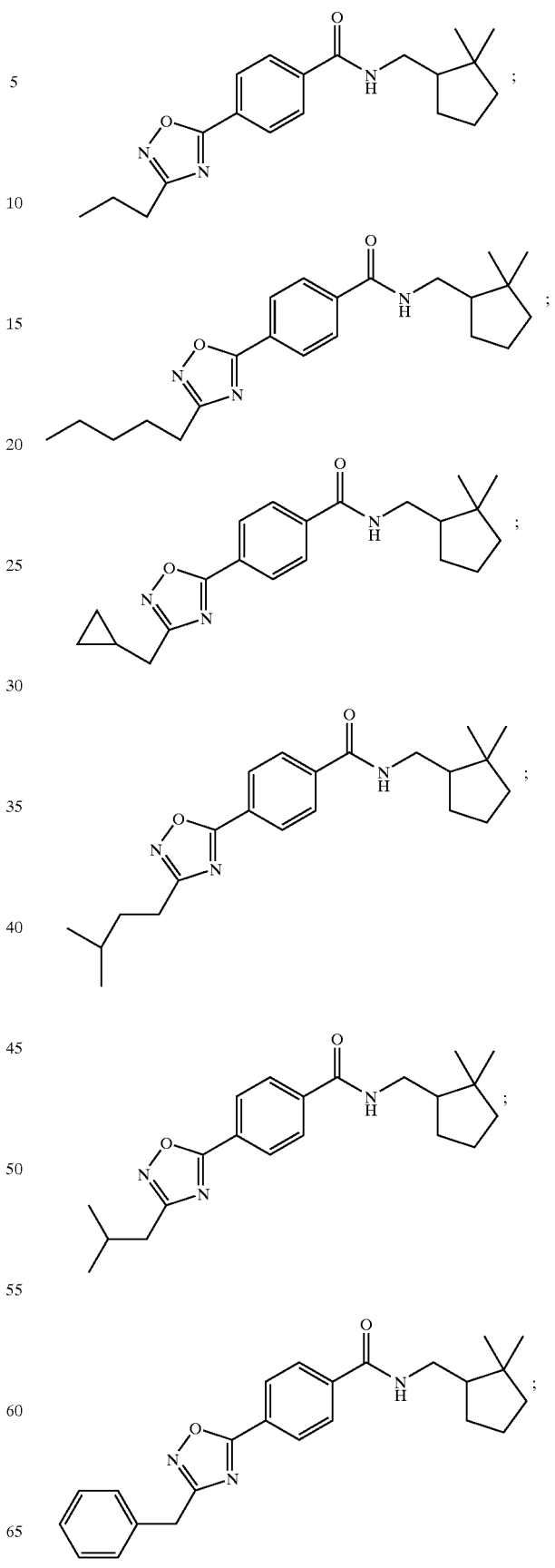

-continued
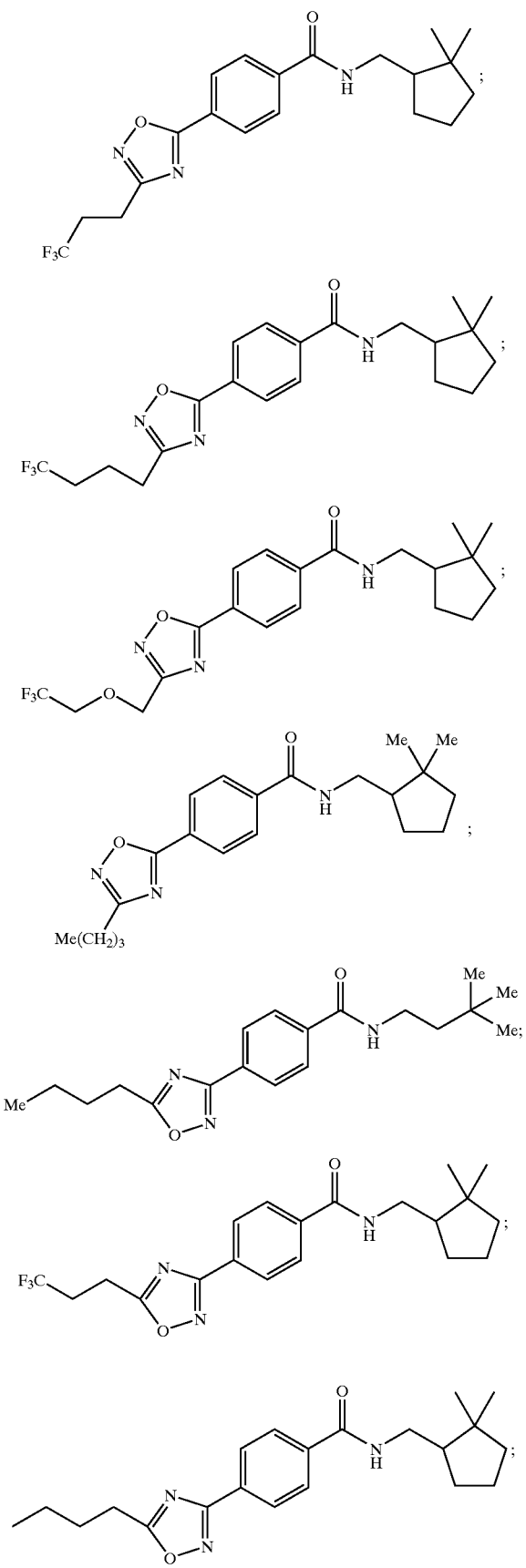
-continued
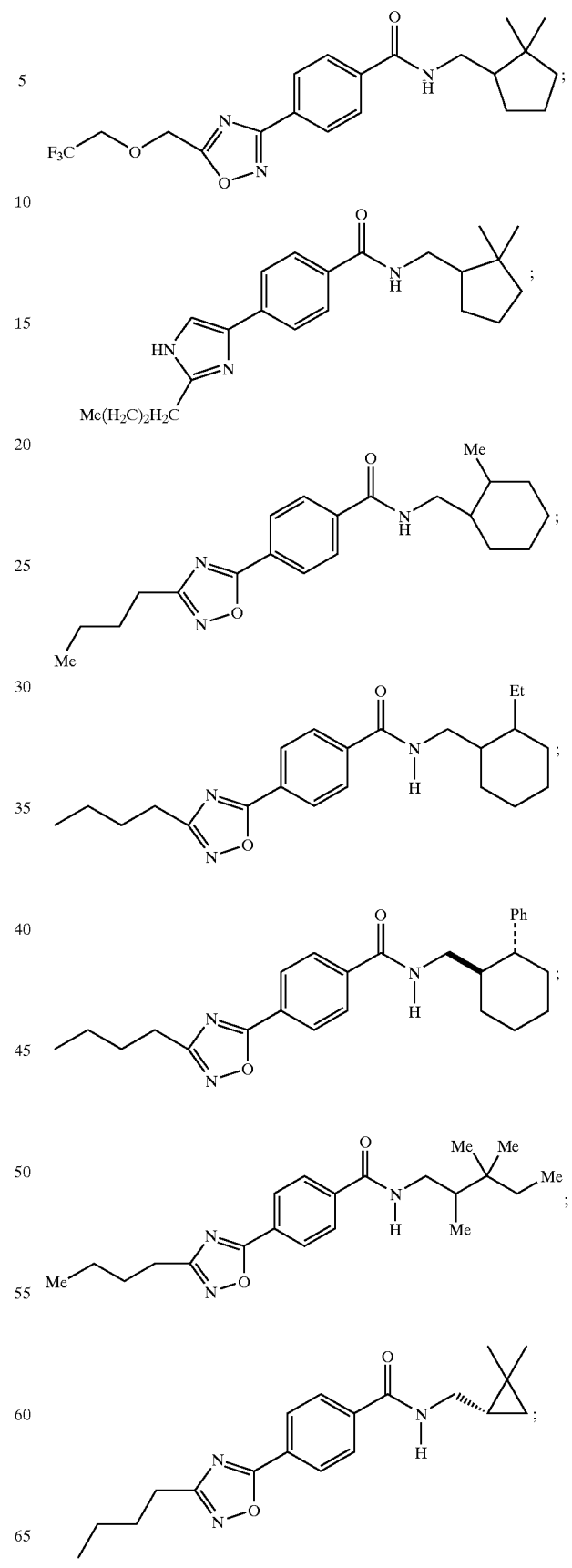

147
-continued
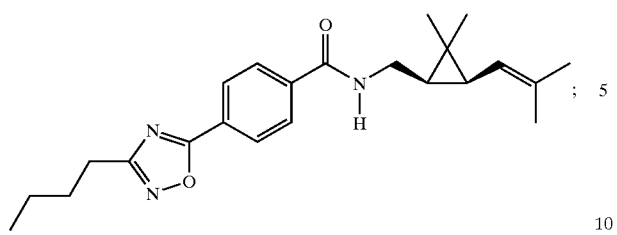
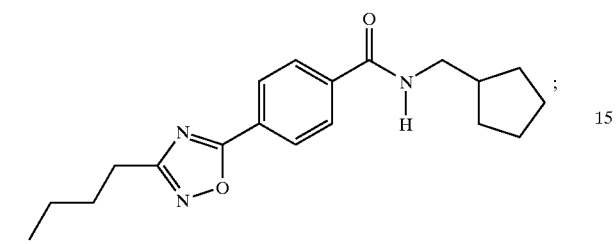
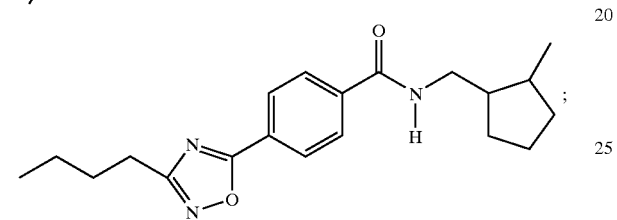
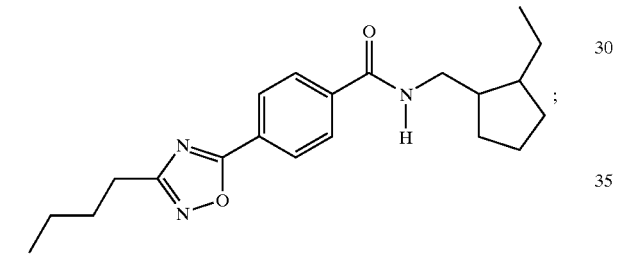
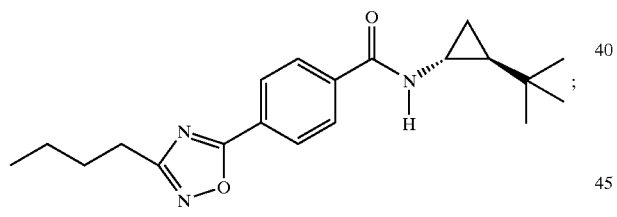
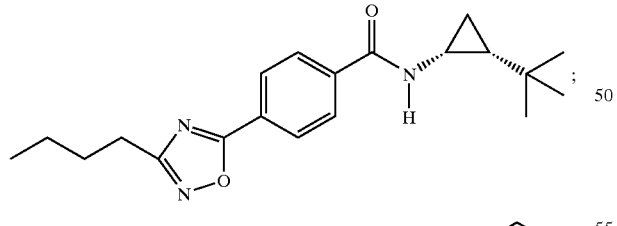
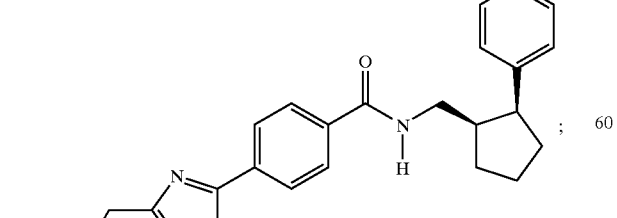
148
-continued
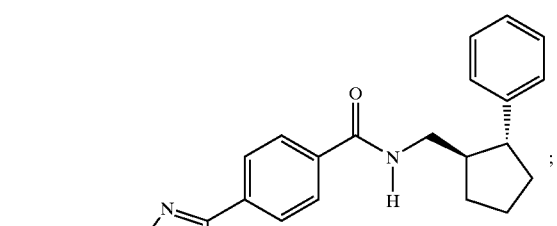
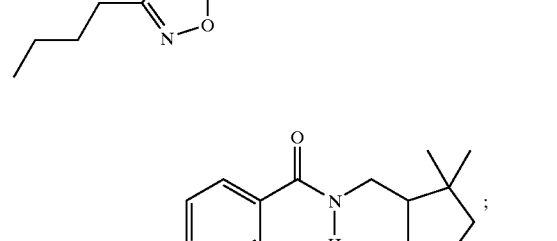
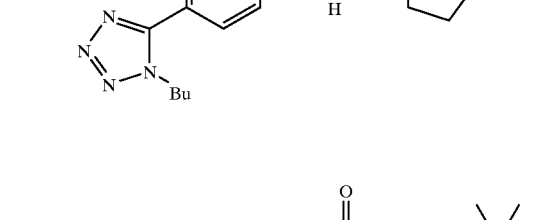
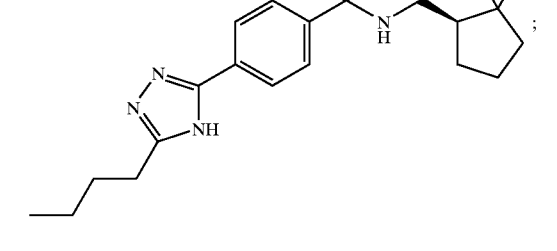
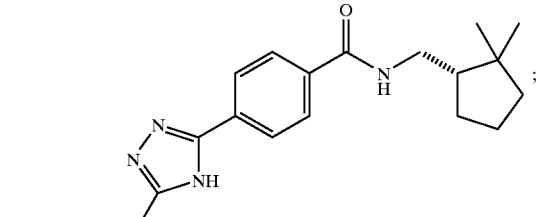
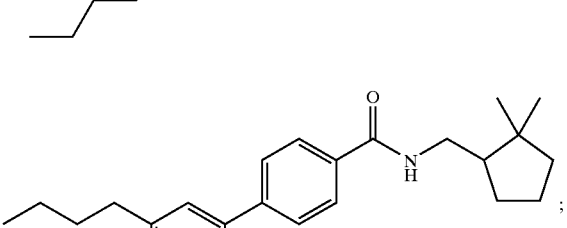
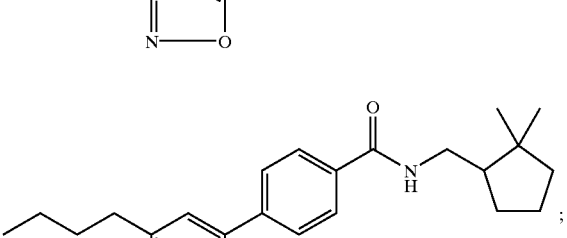

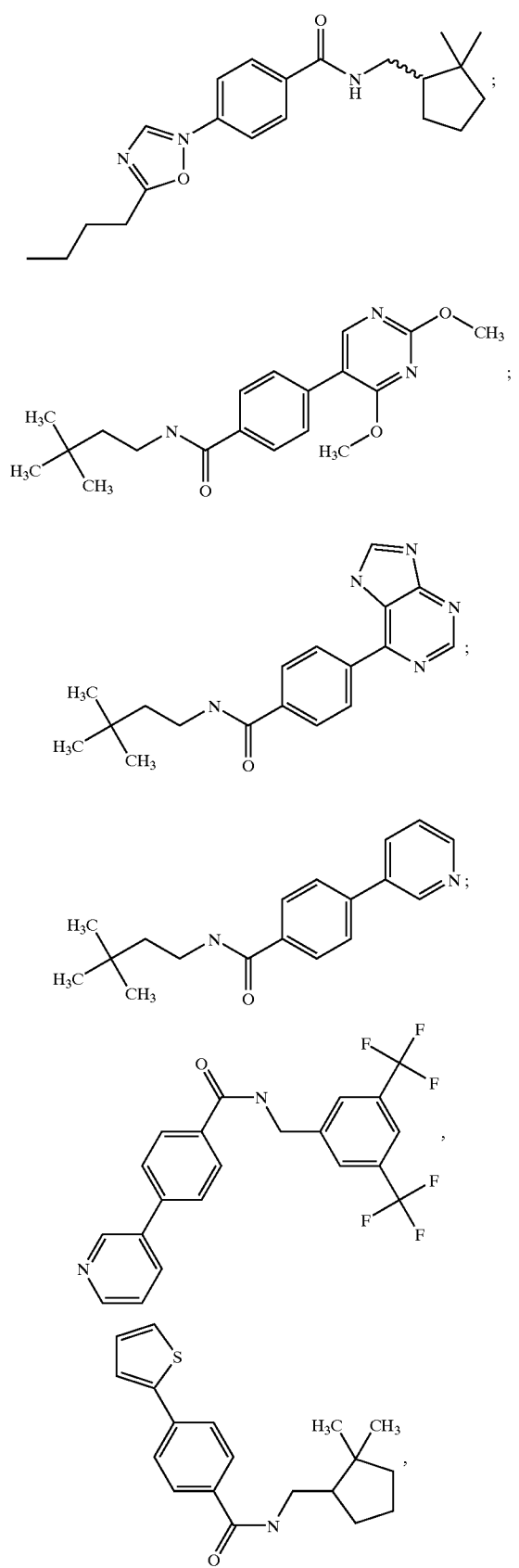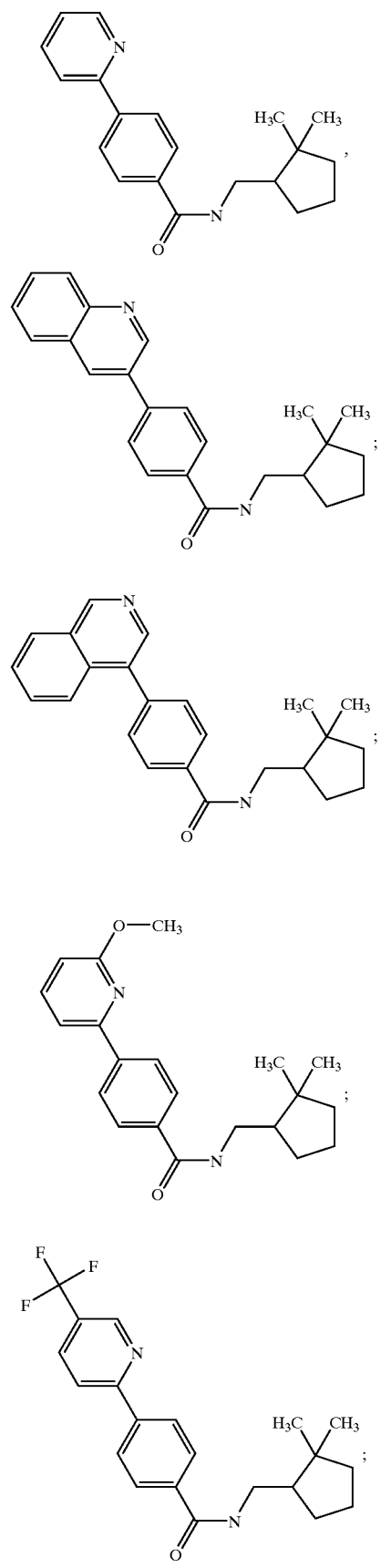

-continued
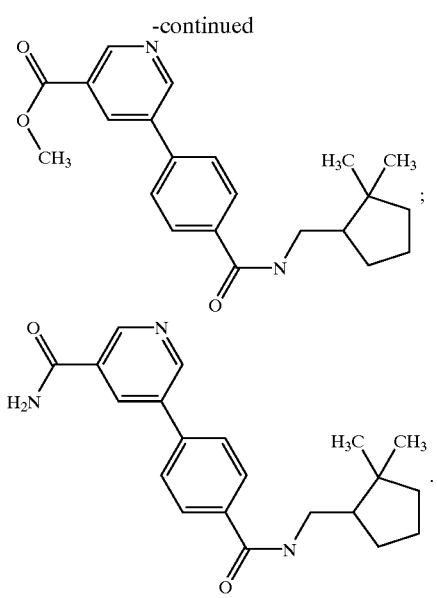
or a pharmaceutically acceptable salt thereof.
4. The compound as defined in claim 2 wherein the substituent attached to the ozadiazolyl ring is alkyl.
5. The compound as defined in claim 2 wherein $R^1$ is
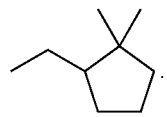
6. The compound as defined in claim 2 having the structure
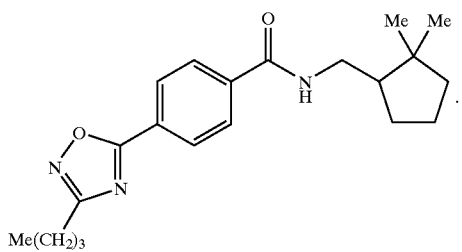
* * * * *